US008642733B2

(12) United States Patent
Moe

(10) Patent No.: US 8,642,733 B2
(45) Date of Patent: Feb. 4, 2014

(54) T-CELL STIMULATING PROTEIN B AND METHODS OF USE

(75) Inventor: Gregory R. Moe, Alameda, CA (US)

(73) Assignee: Children's Hospital & Research Center Oakland, Oakland, CA (US)

( * ) Notice: Subject to any disclaimer, the term of this patent is extended or adjusted under 35 U.S.C. 154(b) by 0 days.

(21) Appl. No.: 13/505,263

(22) PCT Filed: Nov. 4, 2010

(86) PCT No.: PCT/US2010/055505
§ 371 (c)(1),
(2), (4) Date: Jul. 17, 2012

(87) PCT Pub. No.: WO2011/057011
PCT Pub. Date: May 12, 2011

(65) Prior Publication Data
US 2012/0276120 A1    Nov. 1, 2012

Related U.S. Application Data

(60) Provisional application No. 61/259,032, filed on Nov. 6, 2009.

(51) Int. Cl.
C07K 14/00        (2006.01)
C07H 21/04        (2006.01)
A61K 38/16        (2006.01)
C12N 5/10         (2006.01)

(52) U.S. Cl.
USPC ......... 530/350; 514/21.2; 536/23.1; 435/69.1

(58) Field of Classification Search
None
See application file for complete search history.

(56) References Cited

U.S. PATENT DOCUMENTS

| 4,443,546 A | 4/1984 | Stemerman et al. |
| 6,861,507 B1 | 3/2005 | Ala'aldeen et al. |
| 2008/0025993 A1 | 1/2008 | Biemans et al. |
| 2008/0248065 A1 | 10/2008 | Granoff et al. |
| 2009/0035328 A1 | 2/2009 | Granoff |

FOREIGN PATENT DOCUMENTS

WO    WO 2006081259    8/2006

OTHER PUBLICATIONS

Lederman et al., Molecular Immunology, 1991, 28: 1171-1181.*
Colman P.M., Research in Immunology, 1994, 145: 33-36.*
Rentero et al., Chimia 2011, 65: 843-845.*
Kenny et al. (1967) "A Chemically Defined Protein-Free Liquid Medium for the Cultivation of Some Species of Neisseria" Bull World Health Organ 37(4):569-573.
Tettelin et al. "Putative tspB protein [Neisseria meningitidis MC58]" NCBI Reference GenPept NP_274748.1, dated Mar. 17, 2000.
Bille et al. (2005) "A chromosomally integrated bacteriophage in invasive meningococci" J. Exp. Med. 201(12):1905-1913.
Bille et al. (2008) "Association of a bacteriophage with meningococcal disease in young adults" PLoS One 3(12):e3885.
Borrow et al. (2001) "Serological basis for use of meningococcal serogroup C conjugate vaccines in the United Kingdom: reevaluation of correlates of protection" Infect Immun. 69(3):1568-1573.
Da Paz et al. (2003) "Polysaccharide production in batch process of Neisseria meningitidis serogroup C comparing Frantz, modified Frantz and Cartlin 6 cultivation media" Brazil. J. Micro. 34(1):27-32.
Gene ID: NGK_1481 "NGK_1481 protein TspB2 [ Neisseria gonorrhoeae NCCP11945 ]" dated Oct. 17, 2012.
Gene ID: NGK_2027 "NGK_2027 protein TspB3 [ Neisseria gonorrhoeae NCCP11945 ]" dated Oct. 17, 2012.
Gene ID: NGO1140 "NGO1140 TspB-like protein [ Neisseria gonorrhoeae FA 1090]" dated Sep. 27, 2012.
Gene ID: NGO1167 "NGO1167 TspB-like protein Neisseria gonorrhoeae FA 1090" dated Aug. 22, 2012.
Gene ID: NMA0776 "NMA0776 cell-surface protein [ Neisseria meningitidis Z2491 ]" dated Dec. 22, 2012.
Gene ID: NMA1173 "NMA1173 cell-surface protein [ Neisseria meningitidis Z2491 ]" dated Dec. 22, 2012.
Gene ID: NMA1797 "NMA1797 TspB protein [ Neisseria meningitidis Z2491 ]" dated Jan. 20, 2012.
Gene ID: NMA2005 "NMA2005 cell-surface protein [ Neisseria meningitidis Z2491 ]" dated Dec. 22, 2012.
Gene ID: NMB0480 "NMB0480 TspB-like protein [ Neisseria meningitidis MC58 ]" dated Dec. 5, 2011.
Gene ID: NMB1548 "NMB1548 tspB protein [ Neisseria meningitidis MC58 ]" dated Dec. 5, 2011.
Gene ID: NMB1628 "NMB1628 tspB protein [ Neisseria meningitidis MC58 ]" dated Dec. 5, 2011.
Gene ID: NMB1747 "NMB1747 tspB protein [ Neisseria meningitidis MC58 ]" dated Dec. 5, 2011.
Gene ID: NMC0025 "NMC0025 TspB protein [ Neisseria meningitidis FAM18 ]" dated Oct. 17, 2012.
Gene ID: NMC0283 "tspB TspB protein [ Neisseria meningitidis FAM18 ]" dated Oct. 17, 2012.
Gene ID: NMC0956 "NMC0956 cell-surface protein [ Neisseria meningitidis FAM18 ]" dated Oct. 17, 2012.
Gene ID: NMC1668 "NMC1668 cell-surface protein [ Neisseria meningitidis FAM18 ]" dated Oct. 17, 2012.
Gene ID: NMC1715 "NMC1715 TspB protein [ Neisseria meningitidis FAM18 ]" Oct. 17, 2012.
Gene ID: NMC1866 "NMC1866 TspB protein [ Neisseria meningitidis FAM18 ]" Dated Oct. 17, 2012.
Gene ID: NMCC_0151 "tspB TspB protein [ Neisseria meningitidis 053442 ]" dated Oct. 17, 2012.
Gene ID: NMCC_0919 "NMCC_0919 cell-surface protein [ Neisseria meningitidis 053442 ]" dated Oct. 17, 2012.
Giuliani et al. (2006) "A universal vaccine for serogroup B meningococcus" Proc Natl Acad Sci USA 103(29):10834-9.

(Continued)

Primary Examiner — Ilia Ouspenski
(74) Attorney, Agent, or Firm — Carol L. Francis; Bozicevic, Field & Francis LLP

(57) ABSTRACT

Polypeptides that can elicit antibodies that bind to T-cell stimulating protein B (TspB) of N. meningitidis, and methods of use, are provided.

29 Claims, 19 Drawing Sheets

(56) References Cited

OTHER PUBLICATIONS

Goldschneider et al. (1969) "Human immunity to the meningococcus. I. The role of humoral antibodies" *J. Exp. Med.* 129(6):1307-1326.

Granoff, et al. (1998) "Bactericidal monoclonal antibodies that define unique meningococcal B polysaccharide epitopes that do not cross-react with human polysialic acid" *J Immunol* 160(10):5028-5036.

Kizil et al. (1999) "Identification and characterization of TspA, a major CD4(+) T-cell- and B-cell-stimulating *Neisseria*-specific antigen" *Infect. Immun.* 67(7):3533-3541.

Moe et al. (2002) "Sequential immunization with vesicles prepared from heterologous *Neisseria meningitidis* strains elicits broadly protective serum antibodies to group B strains" *Infect Immun* 70(11): 6021-6031.

Plested & Granoff, (2008) "Vaccine-induced opsonophagocytic immunity to *Neisseria meningitidis* group B" *Clin Vaccine Immunol* 15(5): 799-804.

Robinson et al. (2005) "T-cell-stimulating protein A elicits immune responses during meningococcal carriage and human disease" *Infect. Immun.* 73(8):4684-4692.

Welsch et al. (2003) "Antibody to genome-derived neisserial antigen 2132, a *Neisseria meningitidis* candidate vaccine, confers protection against bacteremia in the absence of complement-mediated bactericidal activity" *J. Infect. Dis.* 188(11):1730-1740.

Woodridge et al. (1998) "Identification and Analysis of TspB, a Petent T-Cell and B-Cell Stimulating *Neisseria*-Specific Antigen" *11th International Pathogenic Neisseria Conference* Nice, France, p. 197.

\* cited by examiner

Figure 2
A
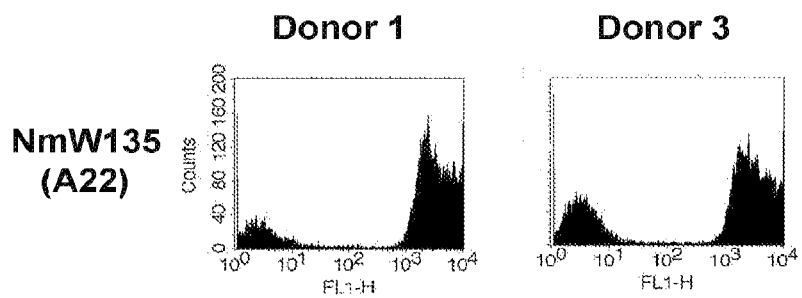
B
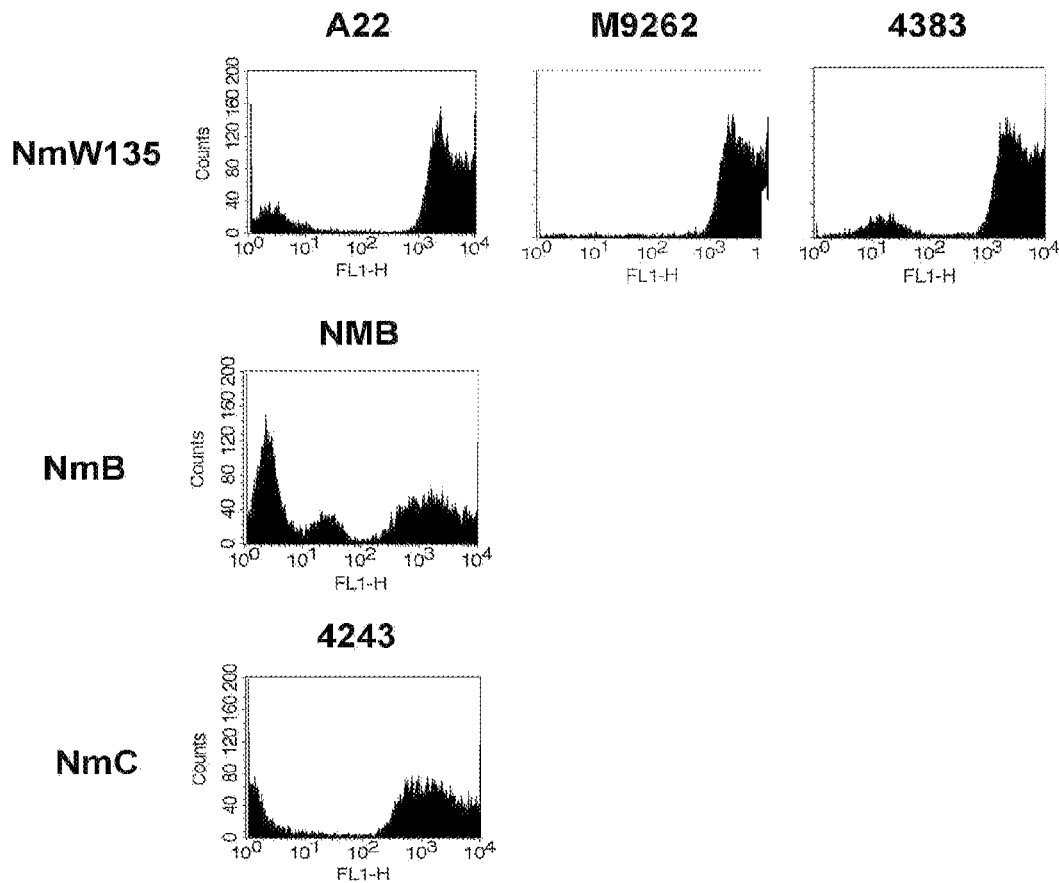

Figure 4

```
Match to: A81922 Score: 64 Expect: 0.0026
Taxonomy: Neisseria meningitidis
Probable cell-surface protein NMA0776 - strain Z2491 serogroup A)
Nominal mass (Mr): 56499
Number of mass values searched: 14
Number of values matched: 9
Sequence coverage: 28%

1    MELKLKRLIL ILMLGMFSVN SYAERFKYPI GNSDVRLDID HTKSVVTDFR
51   VDGQRFSGRI IEPSIIEHVP TGARSLEKIP VKVTASVSRA GVLAGVGALV
101  RQGAKLGKRA VPYVGTALLA YDIYETFKDE IKEQGYQYDP ETDKFVKGYE
151  YSNCIWEHAE NGIKTYGCYG VDSSIMRLMS DYSRFPEVKE LMEHQMEIVG
201  RNYWEMVRKN RNDSFRNYNF SRCYFNWNGG NCNIGEDIND ARSFINFSLI
251  RNPKYKEEMD AKKLEEILAL KVDANPDKYI QATGYPGYSE KVEVAPGTKV
301  NMGPVTDRNG NPVQVVATFG RDSQGNTTVD VQVIPRPDLT PGSAEAPETK
351  PKPAPTPETN PKEKENPREE DQDNPKPTPT PGETPSPNES PKDRREEKKP
401  DGNGGLLCDL FPKILACAEM GEPSENDFEG IAIPKAVNEE TWSPDNMFPS
451  SGVCPKDKTF HVFGKAFSVS YQPLCTLMEN VRFAVIIGFI IMSAFITFGS
501  LRKE  (SEQ ID NO: 12)
```

Figure 5

```
YP_974402.1|NMC0283       ------------------------------------------------------------
YP_974170.1|NMC0025       ------------MFLILGRNFLKIILCFSFFVSKFALASVNVPGKFDRVEVYDDGRYLGIRGSDDKR
NP_274555.1|NMB1548       ------------------------------------------------MASVNVPGKFDRVEVYDDGRYLGIRGSDDKR
NP_002343084.1|NMA1797    MKQNVMFIILGRNFLKIILCFSFFVSKFALASVNPGKFDRVEVYDDCRYLGIRGSDDKR
YP_975800.1|NMC1866       MKQNVMFL-LGRNF-KIILCFSFFVPKFALASVNVPGKFDRVEVYDDGRY-GIRGSDDKR
YP_975665.1|NMC1715       ---------MYALSEKYNDNGFKAYKV_GEGGGIYTEYNYKFDKSLNLNVLESSTG-
NP_274634.1|NMB1628       ----------MSLIFLLGSQKKMEKFRMNLFTRNFLIATPILMCCSLSFAEPARIDDRIIKFRPSK
NP_208336.1|NGO1265       ------------------------MLGMFSVNSYAERFKYPIGNSDVRLDIDH
YP_208245.1|NGO1167       -----------------MMYSFEANANAVKISETLSVDT
YP_208219.1|NGO1140       -------------MVTKHTN_NFAKLSI-AILMMYSFEANANAVKISETLSVDT
NP_274748.1|NMB1747       -----------------MMYSFEANANAVKISETLSVDT
                          ----------MYALSEKYNDNGFKAYKV_GEGG
                                                                                  60

|IGB domain→
YP_974402.1|NMC0283       RRVWEGVTDKESGRYLNSEAQDLTVRHVSTGASSTGKVSAVVSSSVSRAGVLAGVGKLAR
YP_974170.1|NMC0025       RRVWEGVFDKESGRYLNSEAQDLTVRHVSTGASSTGKVSAVVSSSVSRAGVLAGVGKLAR
NP_274555.1|NMB1548       RRIWKGVFDRESGRYLTSEAQD_KVRHVSTGASSTGKVSVSSVVSSSVSRAGVLAGVGKLAR
NP_002343084.1|NMA1797    RRIWKGVFDRESGRY_TSEAQDLKVRHVSTGASSTGKVSVSSVVSSSVSRAGV_AGVGKLAR
YP_975800.1|NMC1866       ------ARS_EK--VPVKFTASVSRAGV_AGVGKLAR
YP_975665.1|NMC1715       SKFFESTGYRKINNEFSKFTEAANVEHIPTGAKAR---INAKITASVSRAAVLSVGVKLVR
NP_274634.1|NMB1628       KKSVVTDFRVDGQRFSGRIIEPSIIEHVPTGARSLEKVPVKFTASLEKVPVKFTASVSRAAVLSVGVKLVR
NP_208336.1|NGO1265       GQGAKVHKFVPKSSNIYSSDLTKAVDLTHIPTGAKARINAKITASVSRAGVLSGVGKLVR
YP_208245.1|NGO1167       GQGAKVHKFVPKSSNIYSSDLTKAVD_THIPTGAKARINAKITASVSRAGV_SGVGKLVR
YP_208219.1|NGO1140       GQGAKVHKFVPKSSNIYSSDI-KAVDLTHIPTGAKARINAKITASVSRAGVLSGVGKLVR
NP_274748.1|NMB1747       GIHTEYNYKFDKSLNLN--------VLESSTGARSLEKVPVKVTASVSRAAVLSGVGKLVR
                          .:                    .:  :**:: **:.***:.**. 
                                                                                  120

YP_974402.1|NMC0283       LGAKFSTRAVPYVGTALLAHDVYETFKEDIQAQGYQVD-ETDKFVKGYEYSNCLWYEDER
YP_974170.1|NMC0025       LGAKFSTRAVPYVGTA-LAHDVYE-FKED-QAQGYQYDPETDKFVKGYEYSNC_WYEDER
NP_274555.1|NMB1548       _GAKLSTRAVPYVGTA_LAHDVYETFKEDIQAQGYQYDPETDKFVKGYEYSNCLWYEDKR
NP_002343084.1|NMA1797    LGAKFSTRAVPYVGTALLAHDVYETFKEDIQAQGYDPETDKFVKGYEYSNCLWYEDER
YP_975800.1|NMC1866       LGAKFSTRAVPYVGTALLAHDVYETFKEDIQAQGYQARGYQYDPETDKFVKGYEYSNCLWYEDER
YP_975665.1|NMC1715       LGAKLSTRAVPYVGTALLAHDVYETFKEDIQAQGYQARGYQYDTETDKFVKGYEYSNCLWYEDER
NP_274634.1|NMB1628       LGAKLSTRAVPYVGTAL_AHDVYETFKEDIQAQGYQARGYQYDPETDKFVKGYEYSNCLWYEDKR
NP_208336.1|NGO1265       QGAKFGTRAVPYVGTALLAHDVYETFKEDIQARGCRYDPETDKFVKGYEYANCLWYEDER
YP_208245.1|NGO1167       QGAKFGTRAVPYVGTALLAHDVYETFKEDIQARGCRYDPETDKFVKGYEYANCLWYEDER
YP_208219.1|NGO1140       QGAKFGTRAVPYVGTALLAHDVYETFKEDIQAQGYQYDPETDKFVKGYEYANCLWYEDER
NP_274748.1|NMB1747       LGAKLSTRAVPYVGTALLAHDVYETFKEDIQAQGYQYDPETDKFVKGYEYSNCLWYEDKR
                          ***.:.:*******.*:*.:*****.:*** .. :**::.*:*:*********:*:.*
                                                                                  180
```

Figure 5 (cont'd)

```
YP_974402.1|NMC0283      RINRTYGCYGVDSSIMRLMSDYSRFPEVKELMESQMYRLARPFWNWHKEELNKLSSLDWN
YP_974170.1|NMC0025      RINRTYGCYGVDSSIMRLMSDYSRFPEVKELMESQMYRLARPFWNWHKEELNKLSSLDWN
NP_274555.1|NMB1548      RINRTYGCYGVDSSIMRLMSDDSRFPEVKELMESQMYRLARPFWNWHKEELNKLSSLDWN
NP_002343084.1|NMA1797   RINRTYGCYGVDSSIMRLMSDYSRFPEVKELMESQMYRLARPYWEKLRNRPDMYYFKNYN
YP_975800.1|NMC1866      RINRTYGCYGVDSSIMRLMSDYSRFPEVKELMESQMYRLARPYWEKLRNRPDMYYFKNYN
YP_975665.1|NMC1715      RINRTYGCYGVDSSIMRLMSDYSRFPEVKELMESQMERLARPYWEKLRNRPDMYYFKNYN
YP_274634.1|NMB1628      RINRTYGCYGVDSSIMRLMSDDSRFPEVKELMESQMERLARPFWNWHKEELNKLSSLDWN
YP_208336.1|NGO1265      RINRTYGCYGVDSSIMRLMPDRSRFPEVKQLMESQMYRLARPFWNWRKEELNKLSSLDWN
YP_208245.1|NGO1167      RINRTYGCYGVDSSIMRLMPDRSRFPEVKQLMESQMYRLARPFWNWRKEELNKLSSLDWN
YP_208219.1|NGO1140      RINRTYGCYGVDSSIMRLMPDRSRFPEVKELMESQMYRLARPFWNWHKEELNKLSSLDWN
NP_274748.1|NMB1747      RINRTYGCYGVDSSIMRLMSDDSRFPEVKELMESQMYRLARPFWNWHKEELNKLSSLDWN
                         *********************.*:**********:.*****:***::***********
                                                                                    240

YP_974402.1|NMC0283      NFVLNRCTFDWNGGDCVVNKGDDYRNGANFSLSRNPKYKEEMDAKKLEEILSLKVDANPD
YP_974170.1|NMC0025      NFVLNRCTFDWNGGDCVVNKGDDYRNGANFSLSRNPKYKEEMDAKKLEEILSLKVDANPD
NP_274555.1|NMB1548      NFVLNSCTFDWNGGDCVVNKGDDFRNGADFSLIRNSKYKEEMDAKKLEEILSLKVDANPD
NP_002343084.1|NMA1797   ----FKRCYFGLNGGDCLVAKGDDGRTFISFSLQGNSKYKEEMDAK-KEEILSLKVDANPD
YP_975800.1|NMC1866      ----FKRCYFGLNGGDCLVAKGDDGRTFISFSLQGNSKYKEEMDAKKLEEILSLKVDANPD
YP_975665.1|NMC1715      ----FKRCYFGLNGGDCLVAKGDDGRTFISFSLQGNSKYKEEMDAKKLEEILSLKVDANPD
YP_274634.1|NMB1628      NFVLNRCTFDWNGGDCLVNKGDDFRAGASFSLGRNPKYKEEMDAKKPEEILSLKVDADPD
YP_208336.1|NGO1265      NFVLNRCTFDWNGGGCAVNKGDDFRAGASFSLGRNPKYKEEMDAKKPEEILSLKVDADPD
YP_208245.1|NGO1167      NFVLNRCTFDWNGGGCAVNKGDDFRAGASFSLGRNPKYKEEMDAKKPEEILSLKVDADPD
YP_208219.1|NGO1140      NFVLNRCTFDWNGGDCLVNKGDDFRNGADFSLIRNSKYKEEMDAKKLEEILSLKVDADPD
NP_274748.1|NMB1747      NFVLNRCTFNWNGGDCLVNKGDDFRNGADFSLIRNSKYKEEMDAKKLEEILSLKVDANPD
                             *  *:.*:****.*:..**  .    *:..:******:.** ***********.**
                                                                                    300

YP_974402.1|NMC0283      KYIKATGYPGYSEKVEVAPGTKVNMGPVTDRNGNPVQVVATFGRDSQGNTTVDVQVIPR?
YP_974170.1|NMC0025      KYIKATGYPGYSEKVEVAPGTKVNMGPVTDRNGNPVQVVATFGRDSQGNTTVDVQVIPR?
NP_274555.1|NMB1548      KYIKATGYPGYSEKVEVAPGTKVNMGPVTDRNGNPVQVVATFGRDSQGNTTVDVQVIPR?
NP_002343084.1|NMA1797   KYIKATGYPGYSEKVEVAPGTKVNMGPVTDRNGNPVQVVATFGRDSQGNTTVDVQVIPR?
YP_975800.1|NMC1866      KYIKATGYPGYSEKVEVAPGTKVNMGPVTDRNGNPVQVVATFGRDSQGNTTVDVQVIPR?
YP_975665.1|NMC1715      KYIKATGYPGYSEKVEVAPGTKVNMGPVTDRNGNPVQVVATFGRDSQGNTTVDVQVIPR?
YP_274634.1|NMB1628      KYIKATGYPGYSEKVEVAPGTKVNMGPVTDRNGNPVQVVATFGRDSQGNTTVDVQVIPR?
YP_208336.1|NGO1265      KYIEATGYPGYSEKVEVAPGTKVNMGPVTDRNGNPVQVAATFGRDAQGNTTADVQVIPR?
YP_208245.1|NGO1167      KYIEATGYPGYSEKVEVAPGTKVNMGPVTDRNGNPVQVAATFGRDAQGNTTADVQVIPR?
YP_208219.1|NGO1140      KYIKATGYPGYSEKVEVAPGTKVNMGPVTDRNGNPVQVVATFGRDSQGNTTVDVQVIPR?
NP_274748.1|NMB1747      KYIKATGYPGYSEKVEVAPGTKVNMGPVTDRNGNPVQVVATFGRDSQGNTTVDVQVIPR?
                         ***:*****************************:****:*****:*****.*******
                         ←End IGB domain|
                                                                                    360
```

Figure 5 (cont'd)

```
YP_974402.1|NMC0283     DLTPGSAEAPNAQPLPEVSPAENPANNPAPNENPGTRPNPEPDPDLNPDANPDTDGQPGT
YP_974170.1|NMC0025     DLTPGSAEAPNAQPLPEVSPAENPANNPAPNENPGTRPNPEPDPDLNPDANPDTDGQPGT
NP_274555.1|NMB1548     DLTPGSAEAPNAQPLPEVSPAENPANNPAPNENPGTRPNPEPDPDLNPDANPDTDGQPGT
YP_002343084.1|NMA1797  DLTPGSAEAPNAQPLPEVSPAENPANNPAPNENPGTSPNPEPDPDLNPDANPDTDGQPGT
YP_975800.1|NMC1866     DLTPGSAEAPNAQPLPEVSPAENPANNPAPNENPGTRPNPEPDPDLNPDANPDTDGQPGT
YP_975665.1|NMC1715     DLTPGSAEAPNAQPLPEVSPAENPANNPAPNENPGTRPNPEPDPDLNPDANPDTDGQPGT
NP_274634.1|NMB1628     DLTPGSAEAPNAQPLPEVSPAENPANNPNPNENPGTRPNPEPDPDLNPDANPDTDGQPGT
YP_208336.1|NGO1265     DLTPASAEAPHAQPLPEVSPAENPANNPDPDENPGTRPNPEPDPDLNPDANPDTDGQPGT         420
YP_208245.1|NGO1167     DLTPASAEAPHAQPLPEVSPAENPANNPDPDENPGTRPNPEPDPDLNPDANPDTDGQPGT
YP_208219.1|NGO1140     DLTPGSAEAPNAQPLPEVSPAENPANNPNPNENPGTSPNPEPDPDLNPDANPDTDGQPGT
NP_274748.1|NMB1747     DLTPGSAEAPNAQPLPEVSPAENPANNPNPNENPGTSPNPEPDPDLNPDANPDTDGQPGT
                        ****.******.******************  *:*****:******:***********

YP_974402.1|NMC0283     RPDSPAVPDRPNGRHRKERKEGEDGGLLCKFFPDILACDRLPEPNP--AEDLNLPSETVN
YP_974170.1|NMC0025     RPDSPAVPDRPNGRHRKERKEGEDGGLLCKFFPDILACDRLPEPNP--AEDLNLPSETVN
NP_274555.1|NMB1548     RPDSPAVPGRTNGRDGKDGKDGKDGGLLCKFFPDILACDRLPESNP--AEDLNLPSETVN
YP_002343084.1|NMA1797  SPDSPAVPDRPNGR-------DGKDGGLLCKFFPDILACDRLPEPNP--AEDLNLPSETVN
YP_975800.1|NMC1866     RPDSPAVPDRPNGRHRKERKEGEDGGLLCKFFPDILACDRLPEPNP--AEDLNLPSETVN        478
YP_975665.1|NMC1715     RPDSPAVPDRPNGRHRKERKEGEDGGLLCKFFPDILACDRLPEPNP--AEDLNLPSETVN
NP_274634.1|NMB1628     RPDSPAVPDRPNGRHRKERKEGEDGKDGGLLCKFFPDILACDRLPESNP--AEDLNLPSETVN
YP_208336.1|NGO1265     SPDSPAVPDRPNGRHRKERKEGEDGGLSCYFPEILACQEMGKPSDRMFHDISIPQVTDD
YP_208245.1|NGO1167     SPDSPAVPDRPNGRHRKERKEGEDGGLSCYFPEILACQEMGKPSDRMFHDISIPQVTDD
YP_208219.1|NGO1140     SPDSPAVPDRPNGRHRKERKEGEDGGLSCYFPEILACQEMGKPSDRMFHDISIPQVTDD
NP_274748.1|NMB1747     RPDSPAVPDRPNGRHRKERKEGEDGGLLCYFPDILACDRLPEPNP--AEDLNLPSETVN
                        :********.****      ::****** **:*:**.    ::*:. :..

YP_974402.1|NMC0283     VEFQKSGIFQDSAQCPAPVTFTVTVLDSSRQFAFSFENACTIAERLRYMLLALAWAVAAF
YP_974170.1|NMC0025     VEFQKSGIFQDSAQCPAPVTFTVTVLDSSRQFAFSFENACTIAERLRYMLLALAWAVAAF
NP_274555.1|NMB1548     VEFQKSGIFQDSAQCPAPVTFTVTVLDSSRQFAFSFENACTIAERLRYMLLALAWAVAAF
YP_002343084.1|NMA1797  VEFKKSGIFQDSAQCPAPVTFTITVTVTVLDSSKQFAFSFENACTIAERLRYMLLALAWAVAAF
YP_975800.1|NMC1866     VEFQKSGIFQDSAQCPAPVTFTVTVLDSSRQFAFSFENACTIAERLRYMLLALAWAVAAF       538
YP_975665.1|NMC1715     VEFQKSGIFQDSAQCPAPVTFTVTVLDSSRQFAFSFENACTIAERLRYMLLALAWAVAAF
NP_274634.1|NMB1628     VEFQKSGIFQDSAQCPAPVTFTVTVLDSSRQFAFSFENACTIAERLRYMLLALAWAVAAF
YP_208336.1|NGO1265     ----QYRASYEPLCVFAEKIRFAVLLAFIIMSAF
YP_208245.1|NGO1167     ----QYRASYEPLCVFAEKIRFAVLLAFIIMSAF
YP_208219.1|NGO1140     ----QYRASYEPLCVFAEKIRFAVLLAFIIMSAF
NP_274748.1|NMB1747     ----QYQASYEPLCVFAEKIRFAVLLAFIIMSAF
                        *:   *:::**: *:.*.*: **:::*:*
```

Figure 5 (cont'd)

```
YP_974402.1|NMC0283      FCIRTVSREV     (SEQ ID NO: 1)
YP_974170.1|NMC0025      FCIRTVSREV     (SEQ ID NO: 2)
NP_274555.1|NMB1548      FCIRTVSREV     (SEQ ID NO: 3)
YP_002343084.1|NMA1797 548 FCIRTVSREV   (SEQ ID NO: 4)
YP_975800.1|NMC1866      FCIRTVSREV     (SEQ ID NO: 5)
YP_975665.1|NMC1715      FCIRTVSREV     (SEQ ID NO: 6)
NP_274634.1|NMB1628      FCIRTVSREV     (SEQ ID NO: 7)
YP_208336.1|NGO1265      VVFGSLGGE-     (SEQ ID NO: 8)
YP_208245.1|NGO1167      VVFGSLGGE-     (SEQ ID NO: 9)
YP_208219.1|NGO1140      VVFGSLGGE-     (SEQ ID NO: 10)
NP_274748.1|NMB1747      VVFGSLKGK-     (SEQ ID NO: 11)
                          :  ::  :
```

Figure 7

Leader Peptide (variable)
1                                29
MKQNVMFIILGRNFLKIILCFSFFVSKFA Amino (N-) terminal domain (variable)
30                                                                                   104
LASVNAPGKFDRVEVYDDGRYLGIRGSDDKRRRIWKGVFDRESGRYLTSEAQDLKVRHVSTGASSTGKVSSVVSS Immunoglobulin Binding Domain (also known as the globular β sheet domain) (IGB domain: SEQ ID NO: 47)
105
SVSRAGVLAGVGKLARLGAKLSTRAVPYVGTALLAHDVYETFKEDIQAQGYQYDPETDKFVKGYEYSNCLWYEDKRRINR
TYGCYGVDSSIMRLMSDDSRFPEVKEL        211
212
MESQMYRLARPFWNWHKEELNKLSSLDWNNFVLNSCTFDWNGGDCVVNKGDDFRNGADFSLIRNSKYKEEMDAKKLEEI
LSLKVDANPDKYIKATGYPGYSEKVEVA          318
319                                                               357
PGTKVNMGPVTDRNGNPVQVVATFGRDSQGNTTVDVQVI Proline-rich domain (conserved)
358
PRPDLTPGSAEAPNAQPLPEVSPAENPANNPNPNENPGTSPNPEPDPDLNPDANPDTDGQPGTRPDSPAVPGRTNGRDGKDG
KDGKDGGLLCKFFPDILACDRLPES        464

Membrane anchor domain (variable)
465
NPAEDLNLPSETVNVEFQKSGIFQDSAQCPAPVTFTVTVLDSSRQFAFSFENACTIAERLRYMLLALAWAVAAFFCIRTVSRE
V        548 (full-length : SEQ ID NO: 3)

Figure 8

```
NMA1797      MKQNVMFLIIGRNF_KIILCFSFFVPKFALASVNVPGKFDRVEVYDDGRYLIGIRGSDDKRRR_WKGVFDRESGRYLTSEAQDLKVRH
NMB1548      MKQNVMFLIIGRNFLK-ILCFSFFVSKFALASVNAPGKFDRVEVYDDGRYLIGIRGSDDKRRRIWKGVFDRESGRYLTSEAQDLKVRH  87
NMB1628      ------------------M_GMFSVNSYAERFKYPIGNSDVRLDIDHKKSVV_DFRVDGQRFSGRIIEPSIIEH
NMB1747      ------------------MYALSEKYNDNGFKAYKVLGE------GGGIHTEYNYKFDKSLNLNV_E
NMA0776      -----------MELKLKR_ILIMLGMFSVNSYAERFKYPIGNSDVR_DIDHTKSVVTDFRVDGQRFSGR-IEPSIIEH
                                :  *  *           *         ::                   :.     ::

|IGB domain→
NMA1797      VSIGASSIGKVSSVVSSSVSRAGVLAGVGKLARLGAKFSTRAVPYVGTALLAHDVYETFKEDIQAGYQYDPETDKFVKGYEYSNCI
NMB1548      VSIGASSIGKVSSVVSSVVSSVSRAGV_AGVGKLARLGAKLS_RAVPYVGTALLAHDVYETFKEDIQAGYQYDPETDKFVKGYEYSNC_ 174
NMB1628      VPTGARSLEKVPVKFTASVSRAAVLSGVGKLAR_GAKLSTRAVPYVGTALLAHDVYETFKEDIQAGYQYDPETDKFVKGYEYSNCL
NMB1747      SSTGARSLEKVPVKVTASVSRAAVLSGVK_ARLGAKLSTRAVPYVGTIALLAHDVYETFKEDIQAGYQYDPETDKFVKGYEYSNCL
NMA0776      VP_GARSLEKIPVKVTASVSRAGVLAGVGAKIGKRAVPYVGTALLAYDIYE_FKDEIKEQGYQYDPETDKFVKGYEYSNC_
             : ***  *   ::.:******.**:****:      *      ******:******:** *:  *:***************

|Variant group peptide→
NMA1797      WYEDERRINRTYGCYGVDSS_VRLMSDYSRFPEVKELMESQMERLARPYWEKLRNRPDMYYFKNYN---FKRCYFGLNGGDC_VAKG
NMB1548      WYEDKRRINRTYGCYGVDSSIMRLMSDSSRFPEVKE_MESQMYRLARPFWNWHKEELNKLSSLDWNNFVLNSCTFDWNGGDCVVNKG 261
NMB1628      WYEDKRRINRTYGCYGVDSSIMRLMSDDSRFPEVKELMESQMYRLARPFWNWHKEE_NKLSSLDWNNFVLNRC-FNWNGGDCLVNKG
NMB1747      WYEDKRRINRTYGCYGVDSSIMRLMSDDSRFPEVKELMESQMYRLARPFWNWHKEELNKLSSLDWNNFVLNRCTFNWNGGDCLVNKG
NMA0776      WEHAEN-GIKTYGCYGVDSSIMRLMSDYSRFPEVKELMEHQMEIVGRNYWEMVRKN----RNDSFRNYNFSRCYFNWNGNCNIGED
             *  :.  .: ********.* :****.::*******:**.**  :.:     . :                     :.:.

←End variant group peptide|
NMA1797      D-DGRTFISFSLQGNSKYKEEMDAK-KEEILSLKVDANPDKYIKATGYPGYSEKVEVAPGTKVNMGPVTDRNGNPVQVVATFGRDSQ
NMB1548      D-DFRNGADFSLIRNSKYKEEMDAKKLEEILSLKVDANPDKYIKATGYPG*SEKVEVAPGTKVNMGPVTDRNGNPVQVVATFGRDSQ 347
NMB1628      D-DFRNGADFSLIRNSKYKEEMDAKKLEEILSLKVDANPDKVIKATGYPGYSEKVEVAPGTKVNMGPVTDRNGNPVQVVATFGRDSQ
NMB1747      D-DFRNGADFS_IRNSKYKEEMDAKKLEEILSLKVDANPDKYIKATGYPGYSEKVEVAPGTKVNMGPVTDRNGNPVQVA_FGRDSQ
NMA0776      INDARSFINFS_IRNPKYKEEMDAKKLEEILALKVDANPDKYIQATGYPG*SEKVEVAPGTKVNMGPVTDRNGNPVQVVATFGRDSQ
              *    :.:* : **.********* **** **********:*:*****.****************************:******

←End IGB domain|Proline-rich                                      ←End proline-rich region|
NMA1797      GNTTVDVQVIPRPDLTPGSAEAPNAQPLPEVSPAENPANNPAPNENPGTRPNPEPDPDLNPDANPDTDGQPGTSPDSPAVPDRPNGR
NMB1548      GNTTVDVQVIPRPD_TPGSAEAPNAQPLPEVSPAENPANNPNPNENPGTSPNPEPDPDLNPDANPDTDGQPGTRPDSPAVPGRTNGR 434
NMB1628      GNTTVDVQVIPRPD_TPGSAEAPNAQPLPEVSPAENPANNPNPNENPGTSPNPEPDPD_NPDANPDTDGQPGTRPDSPAVPGRTNGR
NMB1747      GNTTVDVQVIPRPDLTPGSAEAPNAQPLPEVSPAENPANNPNPNENPGTSPNPEPDPD_NPDANPDTDGQPGTRPDSPAVPDRPNGR
NMA0776      GNTTVDVQVIPRPDLTPGSAEAPETKPKPAPTETNPKEKENPREEDQDNPKPTPTPGETPSPNESPKDR---------
             *************.*********:.:*:*.*.:.*:*::**  ::  :*.:*  . :    *:.  :
```

Figure 8 (cont'd)

```
NMA1797    DGKDG------GLLCKFFPD-LACDRLPEPNP--AEDLNLPSETVNVEFKKSGIFQDSAQCPAPVTFTITVLDSSKQFAFSFENACT
NMB1548    DGKDGKDGKDGGLLCKFFPDILACDRLPESNP--AEDLNLPSETVNVEFQKSGIFQDSAQCPAPVTFTVTVLDSSRQFAFSFENACT  519
NMB1628    DGKDGKDGKDGGL-CKFFPDI-ACDRLPESNP--AEDLNLPSE-VNVEFQKSG-FQDSAQCPAPVTFTVTVLDSSRQFAFSFENACT
NMB1747    HRKEREGEDGGLLCDYFPEILACQEMGKPSDGMFHDISIPQVIDDK-WSSHNFLPSNGVCPQPK-FHVFGR----QYQASYEPLCV
NMA0776    -REEKKPDGNGGLICDLFPKILACAEMGEPSENDFEGIAIPKAVNEETWSPDNMFPSSGVCPKDKTFHVFGK----AFSVSYQPICT
              ::   *  ** ***** :    ****  .    :::    *:  .:: ..  :*    :*  *.  :   *  .  *.

NMA1797    IAERLRYMLIALAWAVAAFFCIRTVSREV           (SEQ ID NO: 4)
NMB1548    IAERLRYMLIALAWAVAAFFCIRTVSREV  548      (SEQ ID NO: 3)
NMB1628    IAERLRYMLIALAWAVAAFFCIRTVSREV           (SEQ ID NO: 7)
NMB1747    FAEK-RFAVLLAFIIMSAFVVFGSLKGK-           (SEQ ID NO: 11)
NMA0776    -MENVRFAVIIGFIIMSAFITFGSLRKE-           (SEQ ID NO: 12)
            :    *   :: ::   :**
```

Figure 9

Variant group peptides of group 1 based on group A strain Z2491 gene NMA1797

```
NMA1797 216 MERLARPYWEKLRNRPDMYYFKNYNFKRCYFGLNGGDCLVAKGDDGRTFISFSLQGNSK 274 (SEQ ID NO: 13)
NMC1715 210 MERLARPYWEKLRNRPDMYYFKNYNFKRCYFGLNGGDCLVAKGDDGRTFISFSLQGNSK 268 (SEQ ID NO: 13)
NMC1866 172 MERLARPYWEKLRNRPDMYYFKNYNFKRCYFGLNGGDCLVAKGDDGRTFISFSLQGNSK 230 (SEQ ID NO: 13)
            ***********************************************************
```

Variant group peptides of group 2 based on group B strain MC58 gene NMB1548

```
NMB1548 214 MYRLARPFWNWHKEELNKLSSLDWNNFVLNSCTFDWNGGDCVVNKGDDFRNGADFSLIRNSK 277 (SEQ ID NO: 14)
NMC0283 209 MYRLARPFWNWHKEELNKLSSLDWNNFVLNRCTFDWNGGDCVVNKGDDYRNGANFSLSRNPK 272 (SEQ ID NO: 15)
NMC0025 185 MYRLARPFWNWHKEELNKLSSLDWNNFVLNRCTFDWNGGDCVVNKGDDYRNGANFSLSRNPK 248 (SEQ ID NO: 16)
NMB1628 183 MYRLARPFWNWHKEELNKLSSLDWNNFVLNRCTFNWNGGDCLVNKGDDFRNGADFSLIRNSK 246 (SEQ ID NO: 17)
NMB1747 170 MYRLARPFWNWHKEELNKLSSLDWNNFVLNRCTFNWNGGDCLVNKGDDFRNGADFSLIRNSK 233 (SEQ ID NO: 18)
NGO1167 195 MYRLARPFWNWRKEELNKLSSLDWNNFVLNRCTFDWNGGGCAVNKGDDFRAGASFSLGRNPK 258 (SEQ ID NO: 19)
NGO1140 176 MYRLARPFWNWRKEELNKLSSLDWNNFVLNRCTFDWNGGGCAVNKGDDFRAGASFSLGRNPK 239 (SEQ ID NO: 20)
NGO1265 176 MYRLARPFWNWRKEELNKLSSLDWNNFVLNRCTFDWNGGGCAVNKGDDFRAGASFSLGRNPK 239 (SEQ ID NO: 21)
            ***********:****************** ***:****.* ******:* **.*** **.*
```

Variant group peptide of group 3 based on group A strain Z2491 gene NMA0776

```
196 MEIVGRNYWEMVRKNRNDSFRNYNFSRCYFNWNGGNCNIGEDINDARSFINFSLIRNPK 254 (SEQ ID NO: 22)
```

```
NMA1797   SVSRAGVLAGVGKLARLGAKFSTRAVPYVGTALLAHDVYETFKEDIQAQGYQYDPETDKFVKGYEYSNCLWYEDERRINRTYGCYGVDSS
NMC1866   SVSRAGVLAGVGKLARLGAKFSTRAVPYVGTALLAHDVYETFKEDIQAQGYQYDPETDKFVKGYEYSNCLWYEDERRINRTYGCYGVDSS
NMC1715   SVSRAAVLSGVGKLVRQGAKFSTRAVPYVGTALLAHDVYETFKEDIQARGYQDTETDKFVKGYEYSNCLWYEDERRINRTYGCYGVDSS
NMC0283   SVSRAGVLAGVGKLARLGAKFSTRAVPYVGTALLAHDVYETFKEDIQAQGYQYDPETDKFVKGYEYSNCLWYEDERRINRTYGCYGVDSS
NMC0025   SVSRAAVLSGVGKLARLGAKFSTRAVPYVGTALLAHDVYETFKEDIQAQGYQYDPETDKFVKGYEYSNCLWYEDKRRINRTYGCYGVDSS
NMB1628   SVSRAAVLSGVGKLARLGAKLSTRAVPYVGTALLAHDVYETFKEDIQAQGYQYDPETDKFVKGYEYSNCLWYEDKRRINRTYGCYGVDSS
NMB1747   SVSRAAV_SGVGKLARLGAKLSTRAVPYVGTALLAHDVYETFKED_QAQGYQYDFE_DKFVKGYEYSNCLWYEDKRRINRTYGCYGVDSS
NMB1548   SVSRAGVLAGVGKLAR_GAKLSTRAVPYVGTALLAHDVYE_FKEDIQAQGYQYDPETDKFVKGYEYSNC_WYEDERRINRTYGCYGVDSS  194
NGO-265   SVSRAGVLSGVGKLVRQGAKFGTRAVPYVGTALLAHDVYETFKEDIQARGCRYDPETDKFVKGYEYANCLWYEDERRINR_YGCYGVDSS
NGO1167   SVSRAGVLSGVGKLVRQGAKFSTRAVPYVGTALLAHDVYE_FKEDIQARGYQDTETDKFVKGYEYANCLWYEDERRINRTYGCYGVDSS
NGO1140   SVSRAGVLSGVGKLVRQGAKFGTRAVPYVGALLAHDVYETFKEDIQARGCRYDPETDKFVKGYEYANCLWYEDERRINRTYGCYGVDSS
NMA0776   SVSRAGVLAGVGALVRQGAKLGKRAVPYVGTA_LAYDIYETFKDEIKEQGYQDPETDKFVKGYEYSNCIWEHAENGIK-TYGCYGVDSS
          *****.**:.*** * *** ::.  ***********.:*****:..: ..   :*  *.  :..*************..:**. ***********
```

```
NMA1797   IMRLMSDYSRFPEVKELMESQ-    (SEQ ID NO: 23)
NMC1866   IMRLMSDYSRFPEVKE_MESQ-    (SEQ ID NO: 24)
NMC1715   IMRLMSDYSRFPEVKELMESQ-    (SEQ ID NO: 25)
NMC0283   IMRLMSDYSRFPEVKELMESQ-    (SEQ ID NO: 26)
NMC0025   IMRLMSDYSRFPEVKELMESQ-    (SEQ ID NO: 27)
NMB1628   IMRLMSDDSRFPEVKELMESQ-    (SEQ ID NO: 28)
NMB1747   IMRLMSDDSRFPEVKELMESQ-    (SEQ ID NC: 29)
NMB1548   IMRLMSDDSRFPEVKELMESQ-  215 (SEQ ID NO: 30)
NGO-265   IMRLMPDRSRFPEVKQLMESQ-    (SEQ ID NO: 31)
NGO1167   IMRLMPDRSRFPEVKELMESQ-    (SEQ ID NO: 32)
NGO1140   IMRLMPDRSRFPEVKQIMESQ-    (SEQ ID NO: 33)
NMA0776   IMRLMSDYSRFPEVKELMEHQ-    (SEQ ID NO: 34)
          *****.*  ***********:*
```

```
NMA1797    YKEEMDAKKLEEILSLKVDANPDKYIKATGYPGYSEKVEVAPGTKVNMGPVTDRNGNPVQVVATFGRDSQGNTTVDVQVI
NMC1866    YKEEMDAKKLEEILSLKVDANPDKYIKATGYPGYSEKVEVAPGTKVNMGPVTDRNGNPVQVVATFGRDSQGNTTVDVQVI
NMC1715    YKEEMDAKKLEEILSLKVDANPDKYIKATGYPGYSEKVEVAPGTKVNMGPVTDRNGNPVQVVA-FGRDSQGNTTVDVQVI
NMC0283    YKEEMDAKKLEEILSLKVDANPDKYIKA-GYPGYSEKVEVAPGTKVNMGPVTDRNGNPVQVVATFGRDSQGNTTVDVQVI
NMC0025    YKEEMDAKKLEEILSLKVDANPDKYIKATGYPGYSEKVEVAPGTKVNMGPVTDRNGNPVQVVATFGRDSQGNTTVDVQVI
NMB1628    YKEEMDAKK-EEILSLKVDANPDKYIKATGYPGYSEKVEVAPGTKVNMGPVTDRNGNPVQVVATFGRDSQGNTTVDVQVI
NMB1747    YKEEMDAKKLEEILSLKVDANPDKYIKATGYPGYSEKVEVAPGTKVNMGPVTDRNGNPVQVVATFGRDSQGNTTVDVQVI
NMB1548    -KEEMDAKKLEEILSLKVDANPDKYIKATGYPGYSEKVEVAPGTKVNMGPVTDRNGNPVQVVATFGRDSQGNTTVDVQV- 357
NGO1265    YKEEMDAKKPEEILSLKVDADPDKYIEATGYPGYSEKVEVAPGTKVNMGPVTDRNGNPVQVVAATFGRDAQGNTTADVQVI
NGO1167    YKEEMDAKKPEEILSLKVDADPDKYIEATGYPGYSEKVEVAPGTKVNMGPVTDRNGNPVQVVAATFGRDAQGNTTADVQVI
NGO1140    YKEEMDAKKPEEILSLKVDADPDKYIEATGYPGYSEKVEVAPGTKVNMGPV-DRNGNPVQVVATFGRDAQGNT-ADVQVI
NMA0776    YKEEMDAKKLEEILALKVDANPDKYIQATGYPGYSEKVEVAPGTKVNMGPVTDRNGNPVQVVATFGRDSQGNTTVDVQVI
           ********* **** ***:*.******:*:*****************.********** *******.:***.**:****
```

```
NMA1797    (SEQ ID NO: 35)
NMC1866    (SEQ ID NO: 36)
NMC1715    (SEQ ID NO: 37)
NMC0283    (SEQ ID NO: 38)
NMC0025    (SEQ ID NO: 39)
NMB1628    (SEQ ID NO: 40)
NMB1747    (SEQ ID NO: 41)
NMB1548    (SEQ ID NO: 42)
NGO1265    (SEQ ID NO: 43)
NGO1167    (SEQ ID NO: 44)
NGO1140    (SEQ ID NO: 45)
NMA0776    (SEQ ID NO: 46)
```

Figure 11
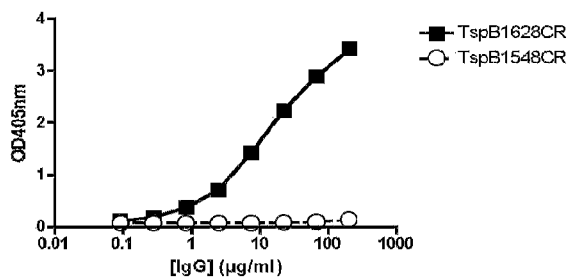
Figure 12
A.
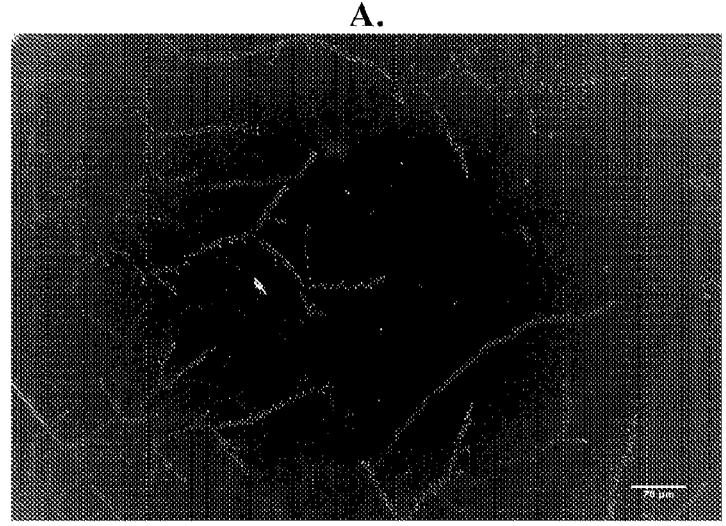
B.
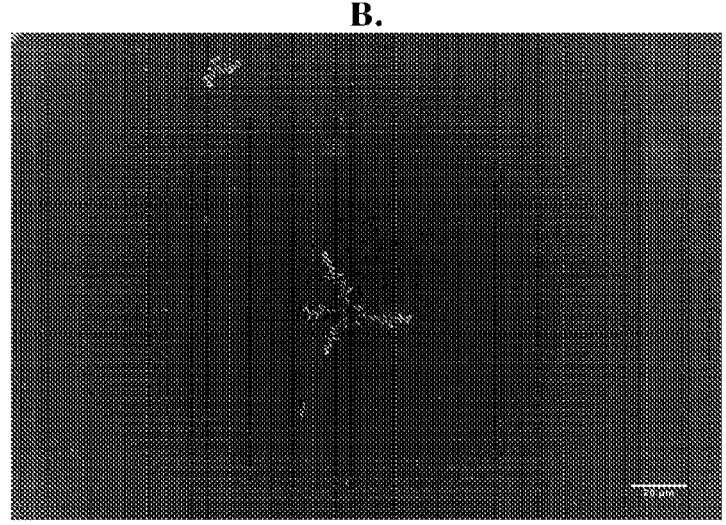

T-CELL STIMULATING PROTEIN B AND METHODS OF USE

CROSS-REFERENCE TO RELATED APPLICATIONS

This application claims priority benefit to U.S. provisional application Ser. No. 61/259,032 filed on Nov. 6, 2009, which application is incorporated herein by reference in its entirety.

STATEMENT REGARDING FEDERALLY SPONSORED RESEARCH

This invention was made with government support under National Institutes of Health grant no. R01 AI064314. The government has certain rights in this invention.

INTRODUCTION

*Neisseria meningitidis* is a Gram-negative bacterium which colonizes the human upper respiratory tract and is responsible for worldwide sporadic and cyclical epidemic outbreaks of, most notably, meningitis and sepsis. The attack and morbidity rates are highest in children under 2 years of age. Like other Gram-negative bacteria, *Neisseria meningitidis* typically possess a cytoplasmic membrane, a peptidoglycan layer, an outer membrane which together with the capsular polysaccharide constitute the bacterial cell wall, and pili, which project into the outside environment. Encapsulated strains of *Neisseria meningitidis* are a major cause of bacterial meningitis and septicemia in children and young adults. The prevalence and economic importance of invasive *Neisseria meningitidis* infections have driven the search for effective vaccines that can confer immunity across different strains, and particularly across genetically diverse group B strains with different serotypes or serosubtypes.

T cell stimulating proteins (Tsps) were identified by Ala'Aldeen et al. in membranes of *Neisseria meningitidis* group B strain SD grown in iron-depleted media (Woodridge K G et al. 11th *International Pathogenic Neisseria Conference* 1998, Nice, France). T cell stimulating proteins designated as TspA and TspB were subsequently identified from genomic expression libraries using rabbit antisera produced by immunizing with the membrane fractions (Woodridge K G et al, supra; Kizil G I et al. 1999 *Infect. Immun* 67:3533-3541). Although TspA and B were both found to stimulate T cells, they are unrelated with respect to DNA sequence.

TspB is homologous to Orf6, which was found to be associated with invasive meningococci when the genome sequences of commensal isolates that did not cause disease were compared with those of invasive isolates that did cause disease (Bille E J R et al. 2005 *J. Exp. Med.* 201:1905-1913). Inactivating Orf6 did not have an observable effect on commonly used laboratory assays for correlates of pathogenicity (e.g. growth in rabbit serum, adhesion to T84 human cells, virulence in an immunocompromised mouse model) (Bille E J R et al. 2005, supra).

SUMMARY

Polypeptides that can elicit antibodies that bind T-cell stimulating protein B (TspB) epitopes of *N. meningitidis*, and inhibit Neisserial TspB from binding to human Ig, and methods of use.

The present disclosure provides an isolated polypeptide comprising a variant peptide region ($V^N$) of a TspB, in which the polypeptide contains a contiguous amino acid sequence that is less than the full-length amino acid sequence of TspB.

BRIEF DESCRIPTION OF THE DRAWINGS

FIG. 2 shows the results of the flow cytometry experiment designed to detect the presence of human IgG bound to *Neisseria meningitidis* group W135 strain A22 cultured in the presence of serum from two different donors (panel A) or genetically diverse *Neisseria meningitidis* group W135, B, and C strains in the presence of serum from a single donor (RGM) (panel B).

FIG. 4 shows the amino acid sequence of the protein identified by MALDI-TOF mass fingerprinting using Mascot. Matched peptides are underlined.

FIG. 5 is an alignment of TspB amino acid sequences from various strains, including invasive *Neisseria meningitidis* group A (Z2491; NMA), group B (MC58; NMB), and group C (FAM18; NMC) and *Neisseria* gonorrheae (FA 1090; NGO) genomes available at NCBI retrieved using the protein sequence of NMA0776.

FIG. 7 shows an amino acid sequence of the full length TspB encoded by gene NMB1548 from the strain MC58 genome sequence.

FIG. 8 is an alignment of 4 of the protein sequences shown in FIG. 5 together with NMA0776. The IGB domain, variant peptide region, and the proline-rich region are labeled along the lengths of the protein sequences.

FIG. 9 shows alignments for three groups of variant peptide sequences that share high sequence identity within each group. The variant peptides are derived from amino acid sequences shown in FIG. 5 along with the amino acid sequence of NMA0776.

FIG. 10, panel A is an alignment of segments of IGB domains that are N-terminal to the variant peptide regions. Panel B is an alignment of segments of IGB domains that are C-terminal to the variant peptide regions. All sequences shown in FIG. 10 are derived from various TspB sequences previously shown in FIGS. 5 and 8.

FIG. 11 shows binding of human IgG to wells containing either TspB1548IGB or TspB628IGB by ELISA.

FIG. 12 are micrographs of TspB1628IGB (panel A) and TspB1548IGB (panel B) spotted on a microscope slide and dried overnight.

Figure 1:
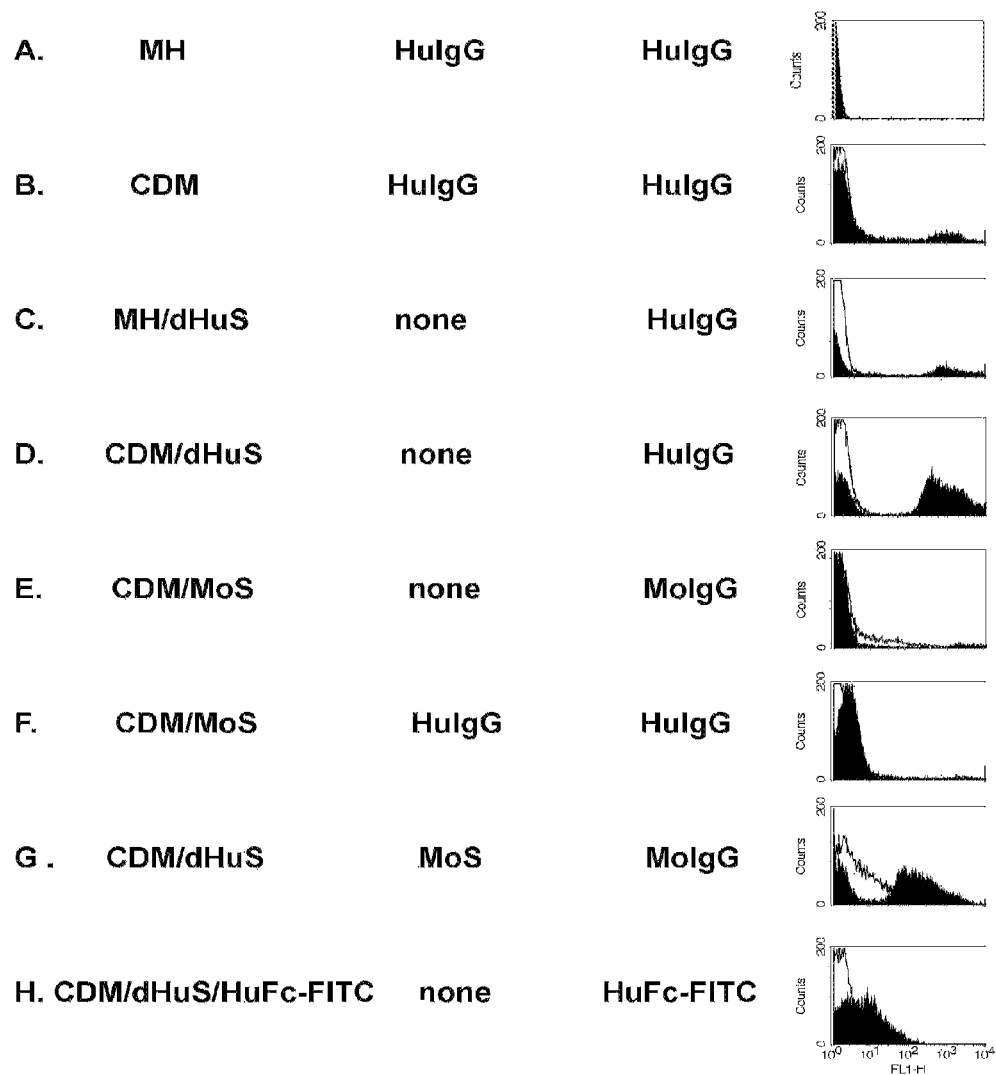
FIG. 1 shows the results of the flow cytometry experiments designed to detect the presence of human or mouse IgG bound to the surface of *Neisseria meningitidis* group W135 strain A22 when the cells are cultured under different conditions and incubated without or with serum or purified IgG as indicated.

Before the present invention and specific examples of embodiments of the invention are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited. To the extent such publications may set out definitions of a term that conflict with the explicit or implicit definition of the present disclosure, the definition of the present disclosure controls.

It must be noted that as used herein and in the appended claims, the singular forms "a", "an", and "the" include plural referents unless the context clearly dictates otherwise. Thus, for example, reference to "an antigen" includes a plurality of such antigens and reference to "the protein" includes reference to one or more proteins, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF EXEMPLARY EMBODIMENTS

Overview

The polypeptides of the present disclosure are derived from (e.g. contain contiguous amino acid sequence of) the T-cell stimulating protein B (TspB). TspB is expressed by various *Neisseria* strains and is also homologous to Orf6, which is found in many invasive *Neisseria meningitidis* strains known to cause the majority of human meningococcal diseases.

In the present disclosure, it is found that TspB/Orf6 expression on the cell surface of the *Neisseria* bacteria is enhanced when cultured in media containing human serum. It is also found that polypeptides presented herein are able to bind to human Ig independent of the antigen-specificity of the human Ig (e.g., by binding to the Fc region). Binding of TspB/Orf6 to human Ig results in activation of human complement but does not lead to productive bacteriolysis or opsonophagocytosis. Accordingly, TspB/Orf6 may facilitate the ability of the bacteria to avoid human complement activation, thus reducing bacterial clearance.

Employing polypeptides of the present disclosure as a vaccine can elicit antibodies. Such antibodies may also prevent binding of TspB to human Ig. The antibodies elicited by the vaccine presented herein may then lead to the inactivation of the mechanism important for the survival of *N. meningitidis* in human blood.

Such polypeptides can find use in combination with other vaccines (e.g. factor H binding protein-containing vaccines, such as r3C), to enhance the bactericidal activity of an anti-Neisserial immune response elicited by the vaccine in a host.

Polypeptides of the present disclosure may also act as a carrier protein when conjugated to other proteins or biomolecules. Such conjugates may be used, for example, in protein-polysaccharide conjugate vaccines.

The present disclosure provides polypeptides derived from the amino acid sequence of TspB but not the full-length TspB, and methods of use of such polypeptides in preparation of vaccines and in eliciting antibodies (e.g. antibodies that block the function of TspB, such as binding Fc region of human IgG). Examples of embodiments of such are described below.

Methods to produce the subject polypeptides and/or full-length TspB are also provided herein. The methods involve culturing host cells that express the polypeptides in chemically defined media supplemented with one or more components of human serum. The method can also be employed to produce vesicles having the subject polypeptides and/or full-length TspB, such as microvesicles, outermembrane vesicles, or a combination of both.

Definitions

"T cell stimulating protein B" (TspB), which is also known in the literature as the protein homologous to the proteins encoded by genes such as NMA0776, NMA1797, and Orf6, is a T-cell and B-cell stimulating protein. Orf6 is one of the nine genes found in prophage DNA that has been linked to invasive disease caused by *N. meningitidis* (Bille E et al. 2005 *J. Exp. Med.* 201:1905-1913), particularly in young adults (Bille et al. 2008 PLoS One 3:e3885). For clarity, the present disclosure may use TspB or Orf6 interchangeably. See FIGS. 5 and 7 for the amino acid sequences of examples of TspB/Orf6.

"Mature TspB" as used herein, refers to a TspB that lacks the leader peptide region. The leader peptide resides at the N-terminus of a naturally-occurring immature TspB.

In referring to amino acid residues in a TspB, the native TspB (NP_274555) of group B strain MC58 encoded by NMB1548 is used herein as a reference sequence for purposes of residue numbering (e.g. see FIG. 7). It is noted, as shown in FIG. 7, that this TspB amino acid sequence contains the leader peptide region. Because the length of TspB can differ from one gene to another by 5, 19, or up to 44 amino acid residues, the numbering system used herein to refer to an amino acid residue in a TspB protein may differ from the numbering based on the actual amino acid sequences of these proteins. Thus, for example, reference to a methionine residue (M) at position 216 of MC58 (NP_274555) sequence in FIG. 5 refers to the residue at position 211 of NMC0283 (YP_974402). For further clarification, see the alignment in FIG. 5.

The terms "polypeptide," "peptide," and "protein", are used interchangeably herein, refer to a polymeric form of amino acids of any length, which can include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

It will be appreciated that throughout this present disclosure reference is made to amino acids according to the single letter or three letter codes. For the reader's convenience, the single and three letter amino acid codes are provided below:

| G | Glycine | Gly | P | Proline | Pro |
|---|---------|-----|---|---------|-----|
| A | Alanine | Ala | V | Valine | Val |
| L | Leucine | Leu | I | Isoleucine | Ile |
| M | Methionine | Met | C | Cysteine | Cys |
| F | Phenylalanine | Phe | Y | Tyrosine | Tyr |
| W | Tryptophan | Trp | H | Histidine | His |
| K | Lysine | Lys | R | Arginine | Arg |
| Q | Glutamine | Gln | N | Asparagine | Asn |
| E | Glutamic Acid | Glu | D | Aspartic Acid | Asp |
| S | Serine | Ser | T | Threonine | Thr |

The terms "nucleic acid molecule" and "polynucleotide" are used interchangeably and refer to a polymeric form of nucleotides of any length, either deoxyribonucleotides or ribonucleotides, or analogs thereof. Non-limiting examples of polynucleotides include linear and circular nucleic acids, messenger RNA (mRNA), cDNA, recombinant polynucleotides, vectors, probes, and primers.

The term "heterologous" refers to two components that are defined by structures derived from different sources, e.g. to provide a nucleic acid or protein not found in nature. For example, where "heterologous" is used in the context of a polypeptide, where the polypeptide includes operably linked amino acid sequences that can be derived from different polypeptides (e.g., a first component composed of a recombinant peptide and a second component derived from a native TspB polypeptide). Similarly, "heterologous" in the context of a polynucleotide encoding a chimeric polypeptide includes operably linked nucleic acid sequence that can be derived from different genes (e.g., a first component from a nucleic acid encoding a peptide according to an embodiment disclosed herein and a second component from a nucleic acid encoding a carrier polypeptide). Such fusion polypeptides as described herein provide for presentation of epitopes in a single polypeptide that are normally found in different polypeptides. Other exemplary "heterologous" nucleic acids include expression constructs in which a nucleic acid comprising a coding sequence is operably linked to a regulatory element (e.g., a promoter) that is from a genetic origin different from that of the coding sequence (e.g., to provide for expression in a host cell of interest, which may be of different genetic origin relative to the promoter, the coding sequence or both). For example, a T7 promoter operably linked to a polynucleotide encoding a TspB polypeptide or domain thereof is said to be a heterologous nucleic acid. "Heterologous" in the context of recombinant cells can refer to the presence of a nucleic acid (or gene product, such as a polypeptide) that is of a different genetic origin than the host cell in which it is present. For example, a Neisserial amino acid or nucleic acid sequence of one strain is heterologous to a Neisserial host of another strain.

The term "operably linked" refers to functional linkage between molecules to provide a desired function. For example, "operably linked" in the context of nucleic acids refers to a functional linkage between nucleic acids to provide a desired function such as transcription, translation, and the like, e.g., a functional linkage between a nucleic acid expression control sequence (such as a promoter, signal sequence, or array of transcription factor binding sites) and a second polynucleotide, wherein the expression control sequence affects transcription and/or translation of the second polynucleotide. "Operably linked" in the context of a polypeptide refers to a functional linkage between amino acid sequences (e.g., of different domains) to provide for a described activity of the polypeptide (e.g., presentation of an epitope to facilitate production of antibodies that specifically bind that epitope).

As used herein in the context of the structure of a polypeptide, "N-terminus" and "C-terminus" refer to the extreme amino and carboxyl ends of the polypeptide, respectively, while "N-terminal" and "C-terminal" refer to relative positions in the amino acid sequence of the polypeptide toward the N-terminus and the C-terminus, respectively, and can include the residues at the N-terminus and C-terminus, respectively. "Immediately N-terminal" or "immediately C-terminal" refers to a position of a first amino acid residue relative to a second amino acid residue where the first and second amino acid residues are covalently bound to provide a contiguous amino acid sequence.

"Derived from" in the context of an amino acid sequence or polynucleotide sequence (e.g., an amino acid sequence "derived from" a TspB) is meant to indicate that the polypeptide or nucleic acid has a sequence that is based on that of a reference polypeptide or nucleic acid (e.g., a naturally occurring TspB or encoding nucleic acid), and is not meant to be limiting as to the source or method in which the protein or nucleic acid is made. "Derived from" in the context of bacterial strains is meant to indicate that a strain was obtained through passage in vivo, or in in vitro culture, of a parental strain and/or is a recombinant cell obtained by modification of a parental strain. Thus, for example, a "TspB-derived polypeptide" is used to described polypeptides that have an amino acid sequence based on that of a naturally-occurring TspB polypeptide.

The term "protective immunity" means that a vaccine or immunization schedule that is administered to a mammal induces an immune response that prevents, retards the development of, or reduces the severity of a disease that is caused by *Neisseria meningitidis*, or diminishes or altogether eliminates the symptoms of the disease. Protective immunity can be accompanied by production of bactericidal antibodies. It should be noted that production of bactericidal antibodies against *Neisseria meningitidis* is accepted in the field as predictive of a vaccine's protective effect in humans (Goldschneider et al. 1969 *J. Exp. Med.* 129:1307; Borrow et al. 2001 *Infect Immun.* 69:1568).

The phrase "a disease caused by *Neisseria meningitidis*" encompasses any clinical symptom or combination of clinical symptoms that are present in an infection of a human with *Neisseria meningitidis*. These symptoms include but are not limited to: colonization of the upper respiratory tract (e.g. mucosa of the nasopharynx and tonsils) by a pathogenic strain of *Neisseria meningitidis*, penetration of the bacteria into the mucosa and the submucosal vascular bed, septicemia, septic shock, inflammation, haemmorrhagic skin lesions, activation of fibrinolysis and of blood coagulation, organ dysfunction such as kidney, lung, and cardiac failure, adrenal hemorrhaging and muscular infarction, capillary leakage, edema, peripheral limb ischaemia, respiratory distress syndrome, pericarditis and meningitis.

The phrase "broad spectrum protective immunity" means that a vaccine or immunization schedule elicits "protective immunity" against at least more than one variant, subvariant, and/or strain (and can be against at least two, at least three, at least four, at least five, against at least eight, or more strains) of *Neisseria meningitidis*. The present disclosure specifically contemplates and encompasses a vaccine and vaccination regimen that confers protection against a disease caused by a member of any capsular group (e.g., A, B, C, W135, X, Y 29E), with protection against disease caused by a capsular group B strain of *Neisseria meningitidis* being of interest due to the epidemiological prevalence of strains causing disease with this capsular group and lack of broadly effective group B vaccines. For example, the polypeptides of the present disclosure alone or in combination with other components present an epitope(s) of interest can be used to potentiate bactericidal antibody responses that cross-react across diverse capsular groups.

The terms "host" or "subject" are used interchangeably herein to refer to a human and non-human animal, where non-human animals are generally referred to in the context of production of anti-*Neisseria* antibodies and humans are hosts of interest for vaccination to reduce the risk of disease by *Neisseria* infection.

The phrase "specifically binds to an antibody" or "specifically immunoreactive with", in the context of an antigen (e.g., a polypeptide antigen) refers to a binding reaction which is based on and/or is probative of the presence of the antigen in a sample which may also include a heterogeneous population of other molecules. Thus, under designated conditions, the specified antibody or antibodies bind(s) to a particular antigen or antigens in a sample and do not bind in a significant amount to other molecules present in the sample. "Specifically binds to an antibody" or "specifically immunoreactive with" in the context of an epitope of an antigen (e.g., an epitope of a polypeptide) refers to a binding reaction which is based on and/or is probative of the presence of the epitope in an antigen (e.g., polypeptide) which may also include a heterogeneous population of other epitopes, as well as a heterogeneous population of antigens. Thus, under designated conditions, the specified antibody or antibodies bind(s) to a particular epitope of an antigen and does not bind in a significant amount to other epitopes present in the antigen and/or in the sample.

The phrase "in a sufficient amount to elicit an immune response" means that there is a detectable difference between an immune response indicator measured before and after administration of a particular antigen preparation. Immune response indicators include but are not limited to: antibody titer or specificity, as detected by an assay such as enzyme-linked immunosorbent assay (ELISA), bactericidal assay, flow cytometry, immunoprecipitation, Ouchterlony immunodiffusion; binding detection assays of, for example, spot, Western blot or antigen arrays; cytotoxicity assays, etc.

A "surface antigen" is an antigen that is present in a surface structure of a cell, particularly a bacterium such as *Neisseria meningitidis* (e.g. the outer membrane, capsule, pili, etc.).

"Isolated" refers to a compound of interest that, if naturally occurring, is in an environment different from that in which it may naturally occur. "Isolated" is meant to include compounds that are within samples that are substantially enriched for the compound of interest and/or in which the compound of interest is partially or substantially purified. Where the compound is not naturally occurring, "isolated" indicates the compound has been separated from an environment in which it was made by either synthetic or recombinant means.

"Enriched" means that a sample is non-naturally manipulated (e.g., by an experimentalist or a clinician) so that a compound of interest is present in a greater concentration (e.g., at least a three-fold greater, at least 4-fold greater, at least 8-fold greater, at least 64-fold greater, or more) than the concentration of the compound in the starting sample, such as a biological sample (e.g., a sample in which the compound naturally occurs or in which it is present after administration), or in which the compound was made (e.g., as in a bacterial polypeptide, antibody, chimeric polypeptide, and the like).

"Substantially pure" indicates that an entity (e.g., polypeptide) makes up greater than about 50% of the total content of the composition (e.g., total protein of the composition) and typically, greater than about 60% of the total protein content. More typically, a "substantially pure" refers to compositions in which at least 75%, at least 85%, at least 90% or more of the total composition is the entity of interest (e.g., of the total protein. Preferably, the protein will make up greater than about 90%, and more preferably, greater than about 95% of the total protein in the composition.

TspB-Derived Polypeptides

The present polypeptides find use in eliciting antibodies. Where the elicited antibodies bind TspB, the antibodies may inhibit binding of TspB to human Ig. Such polypeptides find use in production of immunogenic compositions which can be used in methods of eliciting anti-TspB antibodies to facilitate an anti-Neisserial immune response.

Polypeptides of the present disclosure contain contiguous amino acid residues derived from TspB of a length sufficient to serve as an antigenic fragment (e.g., which can be provided in an immunogenic composition). Such polypeptides can have a contiguous amino acid sequence of a TspB that is at least 55 amino acid residues in length, at least 60 to 100 amino acid residues in length, at least 60 to 150 amino acid residues in length, at least 60 to 200 amino acid residues in length, at least 60 to 250 amino acid residues in length, at least 60 to 300 amino acid residues in length, or at least 60 to 400 amino acid residues in length. In addition to being an antigenic fragment, a polypeptide of the present disclosure may also retain the activity of binding to human Ig independent of the antigen-specificity of the human Ig (e.g., by binding to the Fc region).

One example of a polypeptide of the present disclosure contains an immunoglobulin-binding (IGB) domain from strain NMB1548 (e.g. SEQ ID NO: 47) as demarcated in FIGS. 5, 7, and 8. Another example of a polypeptide of the present disclosure contains the IGB domain from another strain, such as NMB1628 (e.g. SEQ ID NO: 48), as shown in FIG. 8.

The term "IGB domain" is also referred to herein as the "globular β sheet" domain or the "constant region" (CR) of TspB. Full length TspB amino acid sequences are aligned in FIG. 5, in which the IGB domains are demarcated. A specific IGB domain found in Nmb 1548 TspB is demarcated in FIG. 7. IGB domains, as well as other domains of a TspB, are also demarcated in FIG. 8 in examples of TspB amino acid sequences.

A polypeptide comprising an amino acid sequence that is substantially similar to the amino acid sequence of a *Neisseria* TspB includes a polypeptide comprising an amino acid sequence having at least about 75%, at least about 80%, at least about 85%, at least about 90%, at least about 95%, at least about 98%, or at least about 99%, amino acid sequence identity to a contiguous stretch of from about 55 aa to about 75 aa, from about 75 aa to about 100 aa, from about 100 aa to about 150 aa, from about 150 aa to about 200 aa, from about 200 aa to about 250 aa, from about 250 aa to about 300 aa, from about 300 aa to about 350 aa, from about 350 aa to about 400 aa, from about 400 aa to about 450 aa, from about 450 aa to about 500 aa, from about 500 aa to about 550 aa, or from about 550 aa to about 580 aa, of a *Neisseria* TspB (e.g., a TspB as set forth in SEQ ID NO: 1. SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, or SEQ ID NO: 12.)

The subject polypeptides may not contain a full-length mature TspB, and may lack at least 5, at least 10, at least 50, at least 100, up to at least 200 or more aa relative to a naturally-occurring full-length mature TspB. For example, the subject polypeptide may be a truncated TspB that lacks the leader peptide sequence and/or the N-terminal variable domain. One such polypeptide can be described as a TspB encoded by gene NMB1548 which is truncated in that it lacks the 104 most N-terminal amino acid residues of the naturally-occurring immature polypeptide. The leader peptide sequence and the N-terminal variable domain are sequences N-terminal to the immunoglobulin binding (IGB) domain, as shown in FIGS. 7 and 8. The polypeptides can also include or exclude the proline-rich domain.

The polypeptides of the present disclosure can be described as having an IGB domain as shown in FIGS. 5, 7, and 8. The IGB domain of TspB begins with serine 105 and ends before the proline-rich domain starting at proline 358. The serine and the proline in each TspB that mark the beginning of the IGB domain and the beginning of the proline-rich domain, respectively, are bolded in FIGS. 5 and 8. As noted above, the amino acid residue numbering system as referred to herein is based on NP_274555 as encoded by NMB1548 of strain MC58. As noted above, the term "IGB domain" is also synonymous with the globular β sheet domain or the constant region (CR) as shown in FIG. 7.

Within each IGB region of a TspB, there is a contiguous segment of amino acid residues that do not share high amino acid sequence identity across all TspB sequences shown in FIGS. 5 and 8. This contiguous segment of amino acid sequence labeled as "variant group peptide" in FIG. 8, is flanked on both its N-terminus and the C-terminus by amino acid sequences that are highly conserved across TspB sequences shown in FIGS. 5 and 8. The amino acid sequences of the variant peptide regions can be used as a basis to categorize the variant peptide regions into groups, referred to herein as TspB groups. The alignment of variant peptide regions shows highly conserved variant peptide sequences within each TspB group. Such alignments of some examples of variant peptide regions are shown in FIG. 9.

"Variant group peptide" or "$V^N$" refers to a contiguous amino acid sequence of TspB which can be used to assign Neisserial strains to "groups" based on similarity of the amino acid sequence in this region. As illustrated in FIGS. 7, 8, and 9, $V^N$ begins with methionine 214 (M214) and ends at lysine 277 (K277), which are shown as bolded and underlined in the amino acid sequence of TspB (FIG. 7). The methionine that begins the variant group peptide region for each TspB is also bolded in FIG. 8. As seen in FIG. 9, variant group peptides are highly conserved within each of the three groups shown.

The subject polypeptide can contain one or a multimer (e.g., at least two, at least three or more) of variant group peptide regions, each independently selected from a group shown in FIG. 9. For example, a subject polypeptide can contain a contiguous amino acid sequence of at least 84%, at least 85%, at least 86%, at least 88%, at least 89%, at least 93%, at least 95%, at least 98%, up to 100% identity with SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, or SEQ ID NO: 22, as set forth in FIG. 9.

Where the subject polypeptide has more than one variant group peptide, the variant group peptides may be separated by a linker. For example, if $V^N$ contains three variant group peptide regions, it may be represented as $V^1$-$L^1$-$V^2$-$L^2$-$V^3$. Where more than one linkers are used in a subject polypeptide, each linker used is independently selected and may be different from other linkers in the subject polypeptide. In addition to the variant group peptides, the polypeptide of the present disclosure can also optionally have other amino acid sequences ($S^N$) in the TspB, such as those within the IGB domain that flank the variant peptide region in TspB amino acid sequences shown in FIGS. 5 and 8.

Where the subject polypeptide contains amino acid sequences flanking ($S^N$) the variant peptide region(s), the flanking amino acid sequence may be a segment of the IGB domain N-terminal to (e.g. preceding) the variant group peptide region (e.g. $S^1$) and/or the segment of the IGB domain C-terminal to (e.g. following) the variant group peptide region (e.g. $S^2$). Contiguous amino acid segments from other areas of TspB can also be incorporated into the subject polypeptide as an $S^N$ (e.g. amino acid sequences beyond the IGB domains).

Examples of amino acid sequences of the IGB domain that are N-terminal to the variant peptide regions (e.g. $S^1$) are set forth in FIG. 10, panel A as SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, and SEQ ID NO: 34.

Examples of amino acid sequences that are C-terminal to the variant peptide regions (e.g. $S^2$) are set forth in FIG. 10, panel B as SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, and SEQ ID NO: 46.

Accordingly, an example of a subject polypeptide may be represented by the following formula $S^1$-$L^1$-$V^N$-$L^2$-$S^2$, in which $L^N$ refers to the one or more linkers which are optionally present or absent to link amino acid sequences together in the subject polypeptide, $V^N$ refers to one or more of the variant group peptide amino acid sequences as described above, and $S^1$ and $S^2$ refer to the flanking amino acid sequences (e.g. as those derived from the IGB domain), also as described above. Some examples of the subject polypeptide may be represented as $S^1$-$V^1$-$L^1$-$V^2$-$L^2$-$V^3$-$S^2$, $S^1$-$V^1$-$S^2$-$L^1$-$S^1$-$V^2$-$S^2$, or $S^1$-$L^1$-$V^1$-$L^2$-$S^2$. Other combinations and permutations are also contemplated herein.

Aside from having a contiguous amino acid sequence from an IGB domain, which may encompass a contiguous amino acid sequence of a variant group peptide region, the subject polypeptide can contain other domains of TspB. For example, the subject polypeptide can further contain contiguous amino acid sequences derived from the proline-rich domain and/or transmembrane anchor domain, as labeled in FIGS. 7 and 8. An example of such a polypeptide may be represented by $V^1$-$S^1$-$S^2$-$S^3$, in which $S^1$ represents a flanking amino acid sequence derived from the IGB domain, $S^2$ represents the proline-rich domain, and $S^3$ represents the membrane anchor domain. $S^1$, $S^2$, $S^3$ can also each be independently substituted with contiguous amino acid sequences from any segment of TspB or other types of proteins. For example, the polypeptide may contain a transmembrane domain from a protein other than TspB (a "heterologous" transmembrane domain). The subject polypeptides containing a transmembrane domain can find use in providing the subject polypeptides in vesicles.

The present disclosure provides an isolated polypeptide, antigenic fragments of a TspB, and variants of a TspB. A subject polypeptide may be isolated from a natural source, e.g., is in an environment other than its naturally-occurring environment. The subject polypeptide may also be recombinantly made, e.g., in a genetically modified host cell (e.g., bacteria; yeast; *Pichia*; insect cells; and the like), where the genetically modified host cell is genetically modified with a nucleic acid comprising a nucleotide sequence encoding the subject polypeptide. The subject polypeptide encompasses synthetic polypeptides, e.g., a subject synthetic polypeptide is synthesized chemically in a laboratory (e.g., by cell-free chemical synthesis).

The polypeptides disclosed herein include those of the specific contiguous amino acid sequences provided herein, as well as those having 1, 2, 3, 4, 5, 6, 7, 8, 9, or 10 usually no more than 10, 6, or 4 amino acid substitutions, where the substitution is usually a conservative amino acid substitution. By "conservative amino acid substitution" generally refers to substitution of amino acid residues within the following groups:

1) L, I, M, V, F;
2) R, K;
3) F, Y, H, W, R;
4) G, A, T, S;
5) Q, N; and
6) D, E.

Conservative amino acid substitutions in the context of a peptide or polypeptide disclosed herein are selected so as to preserve either a presentation of an epitope of interest or the Fc binding activity of the polypeptide. Such presentation may be preserved by substituting with an amino acid with a side chain of similar acidity, basicity, charge, polarity, or size to the side chain of the amino acid being replaced. Guidance for such substitutions may be derived on alignments of amino acid sequences of TspB. For example, according to the alignment shown in FIG. 5, at certain residue positions that are fully conserved (*), substitution, deletion or insertion may not be allowed while at other positions where one or more residues are not conserved, an amino acid change can be tolerated. Residues that are semi-conserved (. or :) may tolerate changes that preserve charge, polarity, and/or size.

The polypeptides of the present disclosure can be provided in a native folded form or an at least partially-denatured form (e.g., partially denatured or fully denatured form).

In one embodiment, the polypeptides are at least partially denatured. Where the polypeptides are in an at least partially-denatured form, the polypeptide may be a mature full-length TspB or fragment thereof. Partially denatured polypeptides can be used as an immunogen to elicit antibodies to TspB. By "at least partially denatured" in the context of a TspB protein or fragment thereof is meant that the protein is modified in tertiary structure relative to native TspB or fragment thereof so as to decrease the ability of the protein to form polymers with TspB or fragments thereof. Partial denaturation can be accomplished by, for example, purification in the presence of a denaturant (e.g., urea, reducing agent, high salt (e.g., lithium chloride, sodium perchlorate), heating, detergent, and so forth. For example, partially denatured polypeptides can be obtained by purifying the polypeptides under denaturing conditions At least partially denatured TspB polypeptides can be identified by examining the ability of the polypeptide to form polymers. For example, by the formation of polymers visible by microscopy or the formation of gels in aqueous solutions of TspB.

At least partially denatured TspB polypeptides can be identified by their ability to elicit anti-TspB antibodies that block immunoglobulin binding to native TspB. The ability of anti-TspB to block IgG binding on live Neisserial bacteria by flow cytometry.

Immunization with an at least partially denatured TspB or fragment thereof of the present disclosure elicits antibodies that block binding of human immunoglobulin. Such can inhibit an important mechanism for the pathogenesis of *Neisseria*. Examples of a partially denatured polypeptide can include the IGB domain of TspB from NmB 1628 (rf TspB1628IGB), that is purified under denaturing conditions.

Protein Conjugates

The polypeptides of the present disclosure can be provided as fusion proteins containing a subject polypeptide as described herein. For example, the polypeptide as described above can be fused to an N-terminal end of another protein.

The polypeptides of the present disclosure may contain one or more additional elements at the N- and/or C-terminus of the polypeptide, such as a protein (e.g. having an amino acid sequence heterologous to the subject polypeptide) and/or a carrier molecule. Exemplary elements that may be linked to the subject polypeptide include a fatty acid moiety (e.g. an aliphatic carboxylic acid) and/or a carrier molecule (e.g., a carrier protein, (e.g. bovine serum albumin (BSA)), ovalbumin, keyhole limpet hemacyanin (KLH), bovine thyroglobulin, soybean trypsin inhibitor, purified protein derivative of tuberculin (PPD), a cytokine or other vaccine antigens such as fHbp, NadA, GNA2132, etc. Such additional elements may be linked to the polypeptide via a linker, e.g. a flexible linker. For example, the polypeptide may be conjugated to a carrier molecule, e.g., to facilitate administration and/or to increase the immunogenicity in a subject to be vaccinated or treated against *N. meningitidis*. The additional moiety may also aid in immunogenicity or forming a complex with another component in a vaccine and/or facilitate delivery to a cell or tissue of interest.

The polypeptide can also be modified to be conjugated to an antigen such as molecular mimetics, capsular polysaccharides, or derivatives thereof. Capsular polysaccharides may be those found in meningococcal group A, C, W135, Y, and/or X. Examples of such are described in U.S. Pat. Nos. 4,727, 136 and 6,030,619, the disclosures of which are incorporated herein by reference.

Where the subject polypeptide is conjugated to a polysaccharide derivative, the polysaccharide derivatives may be a mixture of N-acetyl or de-N-acetyl polysialic acid derivatives, such as those containing long chain hydrocarbons, as well as aggregates thereof. The polysaccharides may be attached to the subject polypeptide at either and/or both the N-/C-terminus, or to an internal amino acid residue. The polysaccharides may be conjugated via a linker or directly to an amino acid residue. Polysaccharide derivatives suitable for use in the TspB conjugates contemplated herein, as well as methods of making such polysaccharide derivatives, known in the art.

When provided as a fusion protein, the carrier molecules may facilitate presentation of the globular domain of TspB to the immune system and thus facilitate production of anti-*N. meningitidis* antibodies having properties of binding to human Ig. The polypeptide can be fused at the N-terminus, fused at the C-terminus, or positioned in the scaffold such that the amino acid sequence of the globular domain of TspB is flanked by carrier protein sequence. The scaffold may also facilitate display of the polypeptide on a membrane surface (e.g. a vesicle vaccine). The polypeptides are heterologous to the carrier protein and thus provide for a fusion polypeptide not found in nature.

Linkers

As noted above, linkers may be optionally present in a conjugate of the subject polypeptide. Linkers suitable for use in modifying the polypeptides to include additional elements exemplified above include "flexible linkers". Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids.

Examples of flexible linkers include glycine polymers $(G)_n$, glycine-serine polymers (including, for example, $(GS)_n$, $GSGGS_n$ (SEQ ID NO:50) and $GGGS_n$ (SEQ ID NO:60), where n is an integer of at least one), glycine-alanine polymers, alanine-serine polymers, and other flexible linkers known in the art. Glycine and glycine-serine polymers are of interest since both of these amino acids are relatively unstructured, and therefore may serve as a neutral tether between components. Glycine polymers are of particular interest since glycine accesses significantly more phi-psi space than even alanine, and is much less restricted than residues with longer side chains (see Scheraga, Rev. Computational Chem. 11 173-142 (1992)). Exemplary flexible linkers include, but are not limited to GGSG (SEQ ID NO: 51), GGSGG (SEQ ID NO:52), GSGSG (SEQ ID NO:53), GSGGG (SEQ ID NO:54), GGGSG (SEQ ID NO:55), GSSSG (SEQ ID NO:56), and the like. The ordinarily skilled artisan will recognize that design of a polypeptide conjugated to any elements described above can include linkers that are all or partially flexible, such that the linker can include a flexible linker as well as one or more portions that confer less flexible structure.

Methods of Production

The polypeptides of the present disclosure can be produced by any suitable method, including recombinant and non-recombinant methods (e.g., chemical synthesis). Where the polypeptide is chemically synthesized, the synthesis may proceed via liquid-phase or solid-phase. Solid-phase synthesis (SPPS) allows the incorporation of unnatural amino acids, polypeptide/protein backbone modification. Various forms of SPPS, such as Fmoc and Boc, are available for synthesizing polypeptides of the present invention. Details of the chemical synthesis are known in the art (e.g. Ganesan A. 2006 *Mini Rev. Med. Chem.* 6:3-10 and Camarero J A et al. 2005 *Protein Pept Lett.* 12:723-8).

Briefly, small insoluble, porous beads are treated with functional units on which polypeptide chains are built. After repeated cycling of coupling/deprotection, the free N-terminal amine of a solid-phase attached is coupled to a single N-protected amino acid unit. This unit is then deprotected, revealing a new N-terminal amine to which a further amino acid may be attached. The polypeptide remains immobilized on the solid-phase and undergoes a filtration process before being cleaved off.

Where the polypeptide is produced using recombinant techniques, the methods can involve any suitable construct and any suitable host cell, which can be a prokaryotic or eukaryotic cell, usually a bacterial cell (e.g. *E. coli* BL21 (DE3) or *E. coli* TOP10F') or yeast host cell.

Bacterial cells, such as *Neisseria* bacteria, may be used to produce the subject polypeptides, e.g. where the polypeptide is to be provided in a vesicle-based vaccine. Any of a variety of *Neisseria* strains can be used in the methods to produce the polypeptides of the present disclosure. Pathogenic *Neisseria* spp. or strains derived from pathogenic *Neisseria* spp., particularly strains pathogenic for humans or derived from strains pathogenic or commensal for humans, are of particular interest. Exemplary Neisserial spp. include *N. meningitidis, N. flavescens N. gonorrhoeae, N. lactamica, N. polysaccharea, N. cinerea, N. mucosa, N. subflava, N. sicca, N. elongata,* and the like. "Derived from" in the context of bacterial strains is meant to indicate that a strain was obtained through passage in vivo, or in in vitro culture, of a parental strain and/or is a recombinant cell obtained by modification of a parental strain.

Examples of *N. meningitidis* strains that may be used as host cells can be of any serologic group, serotype or subtype, e.g. serogroups A, B, C, X, Y, Z, 29-E, and W-135. Strains of the serogroups A, B, C, X, Y and W-135 are of particular interest.

In addition to the TspB-derived polypeptides of the present disclosure, Neisserial host cells used for expression of the subject polypeptides can naturally express, or be genetically modified to express other antigens of interest, such as factor H binding protein (fHbp), PorA, GNA2132, and the like. A polypeptide that is expressed from a nucleic acid introduced into a host cell is referred to herein as being "exogenous". Where the host cell produces an endogenous TspB, the exogenous subject polypeptide may have an amino acid sequence that is the same as, or different from, a contiguous amino acid sequence of the endogenous TspB. The gene encoding the native TspB of the host cell may optionally be modified, e.g., to provide a host cell that does not express a functional endogenous TspB, such as a TspB knock out strain.

The *Neisseria* bacteria may also be genetically modified to have a defect in the LPS biosynthesis, as described below. For example, the host cell may be genetically modified to provide for decreased or no activity of the product of the lpxL1 gene and that produces a level of the polypeptide of the present disclosure, sufficient to provide for vesicles that, when administered to a subject, evoke serum anti-TspB antibodies. Details on the membrane vesicle preparation and decreasing the expression of the lpxL1 gene are described later below and may also be found in US Pat. Pub. No. 20090035328 and PCT Pub. WO 2006/081259, disclosures of which are incorporated herein by reference.

The present disclosure also provides a method of producing the subject polypeptide and/or a full-length mature TspB, in which the *Neisseria* host cells are cultured in the presence of human serum. The subject method may be employed to provide the subject polypeptides and/or a full-length mature TspB in a vesicle (e.g. for use as a vesicle vaccine). Where the method is used to provide polypeptides in vesicles, the vesicles produced can contain one, two, three, or more different types of the polypeptides described above. The vesicles may also include full-length mature TspB alone or in addition to any of polypeptides described above. The host cells used may optionally have a disruption in endogenous TspB production, as described above. Production methods can be used to produce outer membrane vesicles (OMV) and/or microvesicles (MV), which can be used in immunogenic compositions either alone or in combination in vesicle-based vaccines. Vesicle vaccines may be found in US Pat Pub No. 20080248065, disclosure of which is incorporated herein by reference. Exemplary host cell culture conditions are discussed below.

By simulating the conditions under which bacteremia manifests in the human blood stream, production of the subject proteins and full-length mature TspB is improved. Thus, when producing subject polypeptides and/or full-length mature TspB in a host cell, the host cell is cultured in chemically defined media supplemented with one or more components of human blood. By "chemically defined media" is intended a media in which most components used in the media are known, and thus contain no significant amounts or detectable amounts of components that are related to unidentified animal serum or unidentified complex natural sources. The chemically defined media (or "CDM") used to produce the subject polypeptides is deficient of non-human animal byproducts, and is supplemented with one or more components of human blood, such as plasma, serum, clotting factors, human complement, and the like. Components of human blood include those found in human Cohn Fraction IV serum (e.g. α-globulins and/or β-globulins). Human Cohn Fraction IV is a fractionation of human plasma and can be obtained from commercial sources, such as SIGMA-ALDRICH® (catalogue no. G3637). The chemically defined media for culturing *Neisseria* bacteria employed as host cells contain all the necessary components suitable for expression of the desired antigenic determinant, are deficient of non-human animal byproducts, and contain one or more components of human blood.

Several chemically defined, synthetic media can be utilized for producing the polypeptides of the present disclosure (e.g., for purposes of production and isolation of recombinant protein or production of vesicles having the recombinant protein), as well as for screening antibodies to TspB. Media that may be employed in the subject method include NMFM, Watson-Scherp, Frantz, modified Frantz, NMFM, Catlin, and Catlin 6 cultivation media (Frantz, I. D. Jr., *J. Bact*. (1942) 43:757-761; Catlin, B. W., *J. Inf. Dis*. (1973) 128(2):178-194; Watson et al., Chemical *Nature. J Immunol*. (1958) 81:337-44; Marcelo Fossa da Paz et al., *Braz. J. Microbiol*. 34(1) Sao Paulo January/April 2003). Other synthetic media with various compositional modifications for modulating capsular polysaccharide production in bacteremia agents are well known, and include, but are not limited to: animal free meningococcal polysaccharide fermentation medium, containing soy peptone as a nitrogen source (U.S. Pat. No. 6,933,137), and large scale and serogroup-specific meningococcal media formulations (U.S. Pat. No. 7,491,517). Similarly, chemically defined culture media for other bacteria are well known and can be employed in the subject methods (See, e.g., "*Handbook of media for clinical microbiology*," Ronald M. Atlas and James W. Snyder, 2nd Edition, CRC Press, 2006). The same is true for mammalian cells (See, e.g., "*Towards chemically-defined, serum-free media for mammalian cell culture*," H R Maurer, In Animal Cell Culture: A Practical Approach, Oxford University Press, USA, 1986; Hesse et al., (2000) *Trends in Biotechnology* 18(4):173-180; and Zhang et al. (2005) *J Cytotechnology* 48(1-3):59-74)

As noted above, the media in which host cells are cultured include supplements such as Cohn Fraction IV serum and/or other components of human blood. Components of human blood include, but are not limited to, plasma, plasma with leukocytes (buffy coat), serum and the like. Additional components can be added alone or in various combinations to the media in order to modify one or more parameters of the screening and/or evaluating conditions.

As noted above, the host cells may be genetically modified to express (e.g. overexpress) the polypeptides of the present disclosure. Methods for introduction of genetic material into host cells include, for example, transformation, electroporation, conjugation, calcium phosphate methods and the like. The method for transfer can be selected so as to provide for stable expression of the introduced nucleic acid encoding a polypeptide of the present disclosure. The polypeptide-encoding nucleic acid can be provided as an inheritable episomal element (e.g., plasmid) or can be genomically integrated. Genetic transformation can also be carried out using a polypeptide-encoding nucleic acid tagged with DNA uptake sequence (DUS), as described in Ambur et al. 2007 (*J. Bacteriology* 189:2077-2085) and Bakkali M et al. 2007 (PLoS ONE 2: e741). Homologous recombination may also be employed to transfer a whole construct into a host cell (e.g. an *Neisseria* strain).

Vectors can provide for extrachromosomal maintenance in a host cell or can provide for integration into the host cell genome. A variety of appropriate vectors for use in production of a polypeptide of interest are available commercially (e.g. pET as used in the Example Section). The expression vector provides transcriptional and translational regulatory sequences, and may provide for inducible or constitutive expression, where the coding region is operably linked under the transcriptional control of the transcriptional initiation region, and a transcriptional and translational termination region. In general, the transcriptional and translational regulatory sequences may include, but are not limited to, leader peptide sequences (e.g. pelB), promoter sequences, ribosomal binding sites, transcriptional start and stop sequences, translational start and stop sequences, and enhancer or activator sequences. The subject polypeptide can be expressed by a gene under the control of a promoter that may be heterologous to the nucleic acid encoding TspB. The promoter can provide for constitutive expression (e.g. the promoter of RmpM (reduction modifiable protein), a PorA promoter, etc.), transient expression, and/or expression in the presence of human serum. For example, promoters can be either constitutive or inducible, and can be a strong constitutive promoter (e.g., T7, PorA, RmpM, and the like).

An example of a vector that can be used to produce the subject polypeptide is a pET plasmid as described in the examples and also known in the art. The plasmid can have a pelB leader peptide, followed by nucleic acid encoding the subject polypeptide. The polypeptide-encoding nucleic acid may encode any of the subject polypeptides described above (e.g. IGB, followed by proline-rich domain, which is followed by the membrane anchor domain). The polypeptide-encoding nucleic acid can also followed by any tag that would facilitate protein detection and/or purification (e.g. his tag).

Expression constructs generally have convenient restriction sites located near the promoter sequence to provide for the insertion of nucleic acid sequences encoding proteins of interest. A selectable marker operative in the expression host may be present to facilitate selection of cells containing the vector (e.g. erythromycin selectable marker). The selectable marker may precede the promoter (e.g. a PorA promoter). In addition, the expression construct may include additional elements. For example, the expression vector may have one or two replication systems, thus allowing it to be maintained in organisms, for example in mammalian or insect cells for expression and in a prokaryotic host for cloning and amplification. In addition the expression construct may contain a selectable marker gene to allow the selection of transformed host cells. Selectable genes are well known in the art and will vary with the host cell used.

Isolation and purification of a polypeptide can be accomplished according to methods known in the art. For example, a polypeptide can be isolated from a lysate of cells genetically modified to express the polypeptide, or from a synthetic reaction mixture, by immunoaffinity purification, which generally involves contacting the sample with an anti-polypeptide antibody, washing to remove non-specifically bound material, and eluting the specifically bound polypeptide. The isolated polypeptide can be further purified by dialysis and other methods normally employed in protein purification methods. In one embodiment, the polypeptide may be isolated using metal chelate chromatography methods.

The subject polypeptides may be prepared in substantially pure or isolated form (e.g., free from other polypeptides). In certain embodiments, the polypeptide is present in a composition that is enriched for the polypeptide relative to other components that may be present (e.g., other polypeptides or other host cell components). Purified polypeptide may be provided such that the polypeptide is present in a composition that is substantially free of other expressed polypeptides, e.g., less than 90%, usually less than 60% and more usually less than 50% of the composition is made up of other expressed polypeptides.

As for the preparation of the subject polypeptides with conjugates, coupling may be achieved using a bifunctional coupling agent, such as maleimidobenzoyl sulfosuccinimide ester (conjugation through cysteine residues), N-hydroxysuccinimide (through lysine residues), carbodiimide, glutaraldehyde, succinic anhydride, and the like. Alternatively, or in addition, the antigen and carrier protein may be generated as a fusion protein, described above.

Nucleic Acids

As discussed above, the subject polypeptide may be generated using recombinant techniques to manipulate nucleic acids of different TspB known in the art to provide constructs encoding a polypeptide of interest. It will be appreciated that provided an amino acid sequence, the ordinarily skilled artisan will immediately recognize a variety of different nucleic acids encoding such amino acid sequence in view of the knowledge of the genetic code.

For production of subject polypeptides derived from naturally-occurring polypeptides, it is noted that nucleic acids encoding a variety of different TspBs of *Neisseria* bacteria are known and available in the art. Examples of TspB polypeptides and their nucleic acids are described in, for example, U.S. Pat. No. 6,861,507; Robinson K et al. 2005 *Infect. and Immun.* 73:4684-4692; Bille E et al. 2005 *J. Exp. Med.* 201: 1905-1913; and Bille E et al. 2008 *PLoS One* 3:e3885, disclosures of which are incorporated here by reference.

Nucleic acid (and amino acid sequences) for various TspB are also provided in GenBank as accession nos., such as: Gene ID: NMA0776, protein access. no. A1IQJ2 (from *N. meningitidis* serogroup A); Gene ID: NMA1173, protein access. no. A1IRJ0 (from *N. meningitidis* serogroup A); Gene ID: NMA1797, protein access. no. A1IT08 (from *N. meningitidis* serogroup A); Gene ID: NMA2005, protein access. no. A1ITJ3 (from *N. meningitidis* serogroup A); Gene ID: NMC0025, protein access. no. A1KR75 (from *N. meningitidis* serogroup C, serotype 2a); Gene ID: NMC0283, protein access. no. A1KRW7 (from *N. meningitidis* serogroup C, serotype 2a); Gene ID: NMC0956 protein access. no. A1KTP2 (from *N. meningitidis* serogroup C, serotype 2a); Gene ID: NMC1668, protein access. no. A1KVE8 (from *N. meningitidis* serogroup C, serotype 2a); Gene ID: NMC1715, protein access. no. A1KVI9 (from *N. meningitidis* serogroup C, serotype 2a); Gene ID: NMC1866, protein access. no. A1KVX5 (from *N. meningitidis* serogroup C, serotype 2a); Gene ID: NMCC_0151, protein access. no. A9M0A8 (from *N. meningitidis* serogroup C); Gene ID: NMCC_0919, protein access. no. A9M243 (from *N. meningitidis* serogroup C); Gene ID: NGK_1481, protein access. no. B4RJA5 (from *N. gonorrhoeae*); Gene ID: NGK_2027, protein access. no. B4RNK3 (from *N. gonorrhoeae*); Gene ID: NGO1140, protein access. no. Q5F7B3 (from *N. gonorrhoeae*); Gene ID: NGO1167, protein access. no. Q5F7K4 (from *N. gonorrhoeae*); Gene ID: NMB0480, protein access. no. Q7DDP6 (from *N. meningitidis* serogroup B); Gene ID: NMB1747, protein access. no. Q9JY49 (from *N. meningitidis* serogroup B); Gene ID: NMB1628, protein access. no. Q9JYD9 (from *N. meningitidis* serogroup B); and Gene ID: NMB1548, protein access. no. Q9JYK0 (from *N. meningitidis* serogroup B). Some of the sequences above along with others are also provided with the corresponding gene names in FIGS. 5, 7, and 8.

It will be appreciated that the nucleotide sequences encoding the subject polypeptide may be modified so as to optimize the codon usage to facilitate expression in a host cell of interest (e.g., *E. coli, N. meningitidis*, human (as in the case of a DNA-based vaccine), and the like). Methods for production of codon optimized sequences are known in the art. The nucleic acid sequences may also be modified to express any of the polypeptide of interest described above. Examples include a TspB with both the leader peptide sequence and the N-terminal variable domain truncated, or a segment of the TspB containing the IGB domain. Where the nucleic acids are used in host cells to provide polypeptides in a vesicle (e.g. vesicle-based vaccine), the nucleic acids may also encode a full-length mature TspB, any subject polypeptides described above, or a combination of both.

Formulations

"Antigen composition", "antigenic composition" or "immunogenic composition" is used herein as a matter of convenience to refer generically to compositions comprising a polypeptide that binds to Fc region of human Ig as disclosed herein, in which the subject polypeptide may be optionally conjugated and/or provided in combination to enhance immunogenicity. Compositions useful for eliciting anti-*N. meningitidis* antibodies in a human are specifically contemplated by the present disclosure.

Antigenic compositions can contain 2, 3, 4, 5, 6 or more different polypeptides as described herein, where each subject polypeptide may differ in amino acid sequence.

Additional antigens, e.g., polypeptide antigens that can elicit anti-Neisserial antibodies in addition to or other than TspB may be optionally included in the subject composition. For example, the polypeptides can be provided in combination with polypeptides comprising amino acid sequences of a v.1, v.2, and/or v.3 factor H binding protein (fHbp), e.g., to provide for production of antibodies that bind other proteins associated with the Neisserial diseases, and the like.

In one embodiment, the subject polypeptides are administered in combination with (i.e., in the same or different formulations) with a composition including one or more of the Neisserial antigens fHbp, GNA2132, NadA, GNA2091 and GNA1030, or an antigenic fragment or fusion protein thereof. Exemplary combinations include fHbp, GNA2132 and NadA; and fHbp, GNA2132, Nad A, GNA2091 and GNA1030. In one embodiment, the polypeptide of the present disclosure is provided in combination with the 5 component recombinant protein vaccine as described in Giuliani et al. 2006 *Proc Natl Acad Sci USA* 103:10834-9.

The subject polypeptides can be provided in combination with any of a variety of compositions containing *N. meningitidis* vesicles (e.g., microvesicles and/or outer membrane vesicles), which are produced from an *N. meningitidis* strain expressing fHbp, particularly a v.1 and/or v.2 fHbp and/or v.3 fHbp. A variety of such vesicle compositions are known in the art, and their methods of preparation from a variety of different strains well known.

Antigenic compositions generally comprise an immunologically effective amount of a subject polypeptide, and may further include other compatible components, as may be desired. By "immunologically effective amount" is meant that the administration of that amount to an individual, either in a single dose, or as part of a series of the same or different antigenic compositions, is effective to elicit and/or potentiate an antibody response effective for treatment or prevention of a symptom of, or disease caused by, for example, infection by *Neisseria*, particularly *N. meningitidis*. This amount varies depending upon the health and physical condition of the individual to be treated, age, the capacity of the individual's immune system to produce antibodies, the degree of protection desired, the formulation of the vaccine, the treating clinician's assessment of the medical situation, and other relevant factors. It is expected that the amount will fall in a relatively broad range that can be determined through routine trials.

The concentration of the subject polypeptides in a formulation can vary widely (e.g., from less than about 0.1%, usually at or at least about 2% to as much as 20% to 50% or more by weight) and will usually be selected primarily based on fluid volumes, viscosities, and patient-based factors in accordance with the particular mode of administration selected and the patient's needs.

Polypeptide compositions can be provided in a pharmaceutically acceptable excipient, which can be a solution such as a sterile aqueous solution, often a saline solution, or they can be provided in powder form. Such excipients can be substantially inert, if desired.

The polypeptide compositions can include an adjuvant. Examples of known suitable adjuvants that can be used in humans include, but are not necessarily limited to, alum, aluminum phosphate, aluminum hydroxide, MF59 (4.3% weight/volume squalene, 0.5% weight/volume Tween 80™, 0.5% weight/volume Span 85), CpG-containing nucleic acid (where the cytosine is unmethylated), QS21, MPL, 3DMPL, extracts from Aquilla, ISCOMS, LT/CT mutants, poly(D,L-lactide-co-glycolide) (PLG) microparticles, Quil A, interleukins, and the like. For experimental animals, one can use Freund's, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dip-almitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion. The effectiveness of an adjuvant may be determined by measuring the amount of antibodies directed against the immunogenic antigen or antigenic epitope thereof.

Further exemplary adjuvants to enhance effectiveness of the composition include, but are not limited to: (1) oil-in-water emulsion formulations (with or without other specific immunostimulating agents such as muramyl peptides (see below) or bacterial cell wall components), such as for example (a) MF59™ (WO 90/14837; Chapter 10 in Vaccine design: the subunit and adjuvant approach, eds. Powell & Newman, Plenum Press 1995), containing 5% Squalene, 0.5% Tween 80, and 0.5% Span 85 (optionally containing MTP-PE) formulated into submicron particles using a microfluidizer, (b) SAF, containing 10% Squalane, 0.4% Tween 80, 5% pluronic-blocked polymer L121, and thr-MDP either microfluidized into a submicron emulsion or vortexed to generate a larger particle size emulsion, and (c) RIBI™ adjuvant system (RAS), (Ribi Immunochem, Hamilton, Mont.) containing 2% Squalene, 0.2% Tween 80, and one or more bacterial cell wall components such as monophosphorylipid A (MPL), trehalose dimycolate (TDM), and cell wall skeleton (CWS), preferably MPL+CWS (Detox™); (2) saponin adjuvants, such as QS21 or Stimulon™ (Cambridge Bioscience, Worcester, Mass.) may be used or particles generated therefrom such as ISCOMs (immunostimulating complexes), which ISCOMS may be devoid of additional detergent e.g WO 00/07621; (3) Complete Freund's Adjuvant (CFA) and Incomplete Freund's Adjuvant (IFA); (4) cytokines, such as interleukins (e.g. IL-1, IL-2, IL-4, IL-5, IL-6, IL-7, IL-12 (WO99/44636), etc.), interferons (e.g. gamma interferon), macrophage colony stimulating factor (M-CSF), tumor necrosis factor (TNF), etc.; (5) monophosphoryl lipid A (MPL) or 3-O-deacylated MPL (3dMPL) e.g. GB-2220221, EP-A-0689454, optionally in the substantial absence of alum when used with pneumococcal saccharides e.g. WO 00/56358; (6) combinations of 3dMPL with, for example, QS21 and/or oil-in-water emulsions e.g. EP-A-0835318, EP-A-0735898, EP-A-0761231; (7) oligonucleotides comprising CpG motifs (Krieg Vaccine 2000, 19, 618-622; Krieg Curr opin Mol Ther 2001 3:15-24; Roman et al., Nat. Med, 1997, 3, 849-854; Weiner et al., PNAS USA, 1997, 94, 10833-10837; Davis et al, J. Immunol, 1998, 160, 810-876; Chu et al., J. Exp. Med, 1997, 186, 1623-1631; Lipford et al, Ear. J. Immunol., 1997, 27, 2340-2344; Moldoveami et al., Vaccine, 1988, 16, 1216-1224, Krieg et al., Nature, 1995, 374, 546-549; Klinman et al., PNAS USA, 1996, 93, 2879-2883; Ballas et al, J. Immunol, 1996, 157, 1840-1845; Cowdery et al, J Immunol, 1996, 156, 4570-4575; Halpern et al, Cell Immunol, 1996, 167, 72-78; Yamamoto et al, Jpn. J. Cancer Res., 1988, 79, 866-873; Stacey et al, J. Immunol., 1996, 157, 2116-2122; Messina et al, J. Immunol, 1991, 147, 1759-1764; Yi et al, J. Immunol, 1996, 157, 4918-4925; Yi et al, J. Immunol, 1996, 157, 5394-5402; Yi et al, J. Immunol, 1998, 160, 4755-4761; and Yi et al, J. Immunol, 1998, 160, 5898-5906; International patent applications WO 96/02555, WO 98/16247, WO 98/18810, WO 98/40100, WO 98/55495, WO 98/37919 and WO 98/52581, i.e. containing at least one CG dinucleotide, where the cytosine is unmethylated; (8) a polyoxyethylene ether or a polyoxyethylene ester e.g WO 99/52549; (9) a polyoxyethylene sorbitan ester surfactant in combination with an octoxynol (WO 01/21207) or a polyoxyethylene alkyl ether or ester surfactant in combination with at least one additional non-ionic surfactant such as an octoxynol (WO 01/21152); (10) a saponin and an immunostimulatory oligonucleotide (e.g. a CpG oligonucleotide) (WO 00/62800); (11) an immunostimulant and a particle of metal salt e.g WO 00/23105; (12) a saponin and an oil-in-water emulsion e.g. WO 99/11241; (13) a saponin (e.g QS21)+ 3dMPL+IM2 (optionally+a sterol) e.g WO 98/57659; (14) other substances that act as immunostimulating agents to enhance the efficacy of the composition. Muramyl peptides include N-acetyl-muramyl-L-threonyl-D-isoglutamine (thr-MDP), N-25 acetyl-normuramyl-L-alanyl-D-isoglutamine (nor-MDP), N-acetylmuramyl-L-alanyl-D-isoglutarninyl-L-alanine-2-(1'-2'-dipalmitoyl-sn-glycero-3-hydroxyphosphoryloxy)-ethylamine MTP-PE, etc. Adjuvants suitable for administration to a human are of particular interest.

The polypeptide compositions may comprise other components, such as pharmaceutical grades of mannitol, lactose, starch, magnesium stearate, sodium saccharin, talcum, cellulose, glucose, sucrose, magnesium, carbonate, and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

The polypeptide-containing formulations can be provided in the form of a solution, suspension, tablet, pill, capsule, powder, gel, cream, lotion, ointment, aerosol or the like. It is recognized that oral administration can require protection of the compositions from digestion. This can be accomplished either by association of the composition with an agent that renders it resistant to acidic and enzymatic hydrolysis or by packaging the composition in an appropriately resistant carrier molecule. Means of protecting from digestion are well known in the art.

The polypeptide-containing formulations may be provided so as to enhance serum half-life of the subject polypeptide following administration. For example, where isolated polypeptides are formulated for injection, the polypeptide may be provided in a liposome formulation, prepared as a colloid, or other conventional techniques for extending serum half-life. A variety of methods are available for preparing liposomes, as described in, e.g., Szoka et al. 1980 Ann. Rev. Biophys. Bioeng. 9:467, U.S. Pat. Nos. 4,235,871, 4,501,728 and 4,837,028. The preparations may also be provided in controlled release or slow-release forms.

Combination Vaccines

As noted above, the subject polypeptides can be provided in combination with any of a variety of antigenic compositions for use in eliciting an immune response against *N. meningitidis* in a subject. "Combination" as used herein is meant to include compositions that are formulated separately for separate administration (e.g., as may be provided in a kit), as well as for administration in a single formulation (i.e., "co-formulated").

In view of the above, exemplary antigenic compositions include one or more of the polypeptides of the present disclosure together with recombinant vaccines that include a different Neisserial protein or fragment thereof may be provided as an isolated protein and/or may be provided in a vesicle vaccine. The various components described herein that may be included in an antigenic composition of the present disclosure may be combined together in vitro, ex vivo, and/or be already provided by the host cells used in the subject method. One of ordinary skill in the art may make the combination using any method of choice.

As mentioned above, the antigenic compositions can include elements described above that can be fused to the polypeptides of the present disclosure or as a separate component in the composition. An example of a component that may be included in the composition in addition to the subject polypeptides is the "r3C" vaccine, which contains a recombinant fHbp v.1 (encoded by gene from strain MC58), GNA2132 (encoded by gene from strain NZ98/254), and NadA (encoded by the gene from strain 2996). In certain embodiments, the vesicles may be combined with the 5 component recombinant protein vaccine (5C or rSCV). The 5 component recombinant protein vaccine (rSCv) refers to a recombinant protein vaccine containing GNA2091 fused with fHbp v. 1, GNA2132 (from NZ98/254) fused with GNA1030, and NadA and is described in Giuliani et al. 2006 *Proc Natl Acad Sci USA* 103:10834-9.

Immunization

The polypeptides described herein can be generally administered in an immunogenic composition to a human subject that is at risk of acquiring a Neisserial disease so as to prevent or at least partially arrest the development of disease and its complications. An amount adequate to accomplish this is defined as a "therapeutically effective dose." Amounts effective for use will depend on, e.g., the immunogenic composition, the manner of administration, the weight and general state of health of the patient, and the judgment of the prescribing physician. Single or multiple doses of the immunogenic compositions may be administered depending on the dosage and frequency required and tolerated by the patient, and route of administration.

The polypeptides described herein are generally administered in an amount effective to elicit a humoral immune response in the host. As noted above, amounts for immunization will vary, and can generally range from about 1 µg to 100 µg per 70 kg patient, usually 5 µg to 50 µg/70 kg. Substantially higher dosages (e.g. 10 mg to 100 mg or more) may be suitable, and may be administered parenterally (e.g., by injection or topical administration) or by oral or nasal routes. The initial administration can be followed by booster immunization of the same of different polypeptide-containing antigenic composition. Usually vaccination involves at least one booster, more usually two boosters.

In general immunization can be accomplished by administration by any suitable route, including administration of the composition orally, nasally, nasopharyngeally, enterically, topically, transdermally, subcutaneously, intramuscularly, in tablet, solid, powdered, liquid, aerosol form, locally or systemically, with or without added excipients as may be suitable for the desired route of administration. Actual methods for preparing parenterally administrable compositions will be known or apparent to those skilled in the art and are described in more detail in such publications as Remington's Pharmaceutical Science, 15th ed., Mack Publishing Company, Easton, Pa. (1980).

An immune response can be assessed by known methods (e.g. by obtaining serum from the individual before and after the initial immunization, and demonstrating a change in the individual's immune status, for example an immunoprecipitation assay, or an ELISA, or a bactericidal assay, or a Western blot, or flow cytometric assay, or the like).

In one embodiment, the antigenic compositions can be administered to a human subject, which subject may be immunologically naive with respect to *Neisseria meningitidis*. In a particular embodiment, the subject is a human child about five years or younger, and preferably about two years old or younger, and the antigenic compositions are administered at any one or more of the following times: two weeks, one month, 2, 3, 4, 5, 6, 7, 8, 9, 10, or 11 months, or one year or 15, 18, or 21 months after birth, or at 2, 3, 4, or 5 years of age.

It may be generally desirable to initiate immunization prior to the first sign of disease symptoms, or at the first sign of possible or actual exposure to infection or disease (e.g., due to exposure or infection by *Neisseria*).

Screening Assays

The present disclosure also features methods of screening for effective vaccines, and screening for candidate agents (e.g. antibodies), nucleic acid encoding the same, or immunogens effective for eliciting antisera.

For example, the methods can be used to assess antibody binding, both in terms of via the Fc portion of an antibody and binding of the antigen-specific portion (i.e, the ability of the antibody to bind to TspB through an antigen-binding region). Such assay methods find use in screening candidate agents which can inhibit binding of TspB to human Ig, in which the binding is independent of the antigen-specificity (e.g., by binding to the Fc region). Methods can encompass screening antibodies to identify those that inhibit the function of a Neisserial protein (e.g. binding of TspB to human IgG). For example, a candidate agent that would bind to TspB with an avidity of at least about 30, at least about 40, at least about 50, or at least about 100, up to about 1000-fold or more relative to the affinity a human Ig or fragment thereof (e.g. Fc portion) (e.g. 50 nM vs 50 pM), would be chosen as a candidate used to inhibit the binding of TspB to human Ig.

The subject method involves: analyzing a candidate agent (e.g., an antibody) that may be a candidate for inhibiting binding of TspB to human Ig, in which the binding is independent of the antigen specificity of the Ig (e.g. by binding in the Fc region). Optionally, the method may involve immunizing a non-human animal with a vaccine (e.g., a polypeptide containing an epitope of TspB), collecting serum antibodies from such immunized animals, and screening the serum for the ability to inhibit TspB binding to Ig.

The term "candidate agent" as used herein describes any molecule, e.g. protein or small molecule compound. Accordingly, candidate agents encompass numerous chemical classes, though typically they are organic molecules, preferably small organic compounds having a molecular weight of more than 50 and less than about 2,500 daltons. Candidate agents include functional groups to facilitate structural interaction with proteins, e.g., hydrogen bonding, and can include an amine, carbonyl, hydroxyl, or carboxyl group. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogs or combinations thereof. Candidate agents can be obtained from a wide variety of sources including libraries of synthetic or natural compounds. For example, numerous means are available for random and directed synthesis of a wide variety of organic compounds and biomolecules, including expression of randomized oligonucleotides and oligopeptides.

Alternatively, libraries of natural compounds in the form of bacterial, fungal, plant and animal extracts (including extracts from human tissue to identify endogenous factors affecting the function of TspB) are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

As noted above, analysis of candidate agents may be carried out by assessing the ability of TspB to bind to human Ig or a fragment thereof (e.g. Fc fragment) in the presence of a candidate agent, either in a cell-free or cell-based assay. Serial dilution experiments can be carried out to select for candidates that exhibit many fold increase of affinity to TspB relative to human Ig or a fragment thereof (e.g. Fc fragment). The TspB used in the assay may include full-length or fragment thereof, isolated from Neisserial bacteria, synthetically made, recombinantly made, and/or present on the cell surface of Neisserial bacteria. The candidate agent may also be assessed for its ability to facilitate bactericidal activity using methods known in the art and described in the Examples below.

Depending on the assay format used, a polypeptide containing human Ig (or fragment thereof), the TspB protein, and/or the subject polypeptides, may be labeled in the subject screening method. The TspB, the subject polypeptides, and/or a polypeptide containing human Ig or a fragment thereof (e.g. Fc portion) can optionally be immobilized on a support through covalent or non-covalent attachment. An exemplary screening assay may be a competitive binding assay, in which a polypeptide containing a human Ig or a fragment thereof (e.g. Fc region) can be detectably labeled and bound to immobilized TspB. Displacement of this detectably labeled reagent from the bound TspB is then assessed in the presence of the candidate agent.

Detectable label includes those that provide for directly detectable signal (e.g., fluorophore) or indirectly detectable signal (e.g., use of a secondary antibody having a detectable label). E.g., a radioactive label, a fluorescent label, chemiluminescers, enzymes, specific binding molecules, particles, e.g. magnetic particles, and the like. Additional elements can be provided to facilitate isolation (e.g., biotin tag, an HA tag, a poly-Histidine tag, an immunologically detectable tag) through various methods (e.g., affinity capture, etc.). Specific binding molecules include pairs, such as biotin and streptavidin, digoxin and antidigoxin etc. For the specific binding members, the complementary member would normally be labeled with a molecule that provides for detection, in accordance with known procedures.

The candidate agent may be also assessed for its affinity for a bacterial cell of interest. Bacterial cells for screening can be selected from *Escherichia coli* K1, *Escherichia coli* K92, any Neisserial bacteria (e.g. *Neisseria meningitidis* Serogroup B, *Neisseria meningitidis* Serogroup C, *Neisseria meningitidis* Serogroup X, *Neisseria meningitidis* Serogroup Y, *Neisseria meningitidis* Serogroup W-135, and the like).

Where the candidate agent is an antibody is provided in an antibody population, and the method can involve isolating one or more antibodies from the antibody population that bind bacterial cell, bind TspB, and/or inhibit binding of TspB to human Ig. The isolated antibodies identified by such screening can facilitate bactericidal activity against the bacterial cell, e.g., by facilitating complement-mediated bactericidal activity and/or opsonophagocytotic activity capable of decreasing the viability of the bacteria in human blood.

When producing TspB or the subject polypeptide in bacteria to be used in the subject method, the bacterial cell is cultured in chemically defined media supplemented with one or more components of human blood. Chemically defined media that are supplemented with human serum are employed in the subject screening methods for conditions under which the bacterial cells are cultured and/or for conditions under which candidate agent binding (e.g. antibody binding) is performed. Accordingly, the screening methods of the present disclosure is carried out under conditions that simulate bacteremia, and/or neoplasia in humans.

"Chemically defined media" as used in connection with the subject screening assays described herein is intended to be a media that is deficient of non-human animal byproducts. The chemically defined media for *Neisseria meningitidis* employed in the present disclosure contain known components suitable for expression of the desired antigenic determinant, is deficient of non-human animal byproducts, and is further supplemented with one or more components of human blood.

Components of human blood include but are not limited to plasma, plasma with leukocytes, complement, clotting factors such fibrinogen, fibronectin, fibrin, plasminogen, α-globulins, β-globulins, and the like. Where the human blood component is plasma, the plasma is heat-inactivated in order to inactivate intrinsic complement activity. Where the assay involves detecting binding to a particular human antibody, the plasma is depleted of that particular antibody or class of antibody (e.g., IgG). The plasma is also obtained from a donor that lacks intrinsic bacteriocidal activity against the *N. meningitidis* cell of interest. As noted above, an example of human blood component is human Cohn Fraction IV serum, which can be obtained from commercial sources.

The screening and/or evaluating may further include the step of: comparing binding of a candidate agent (e.g. antibody) to a bacterial cell grown in an undefined media, such as a media containing one or more non-human animal byproducts, such as bovine serum and the like. Many undefined media suitable for this purpose are known. For instance, examples of undefined media for supporting growth and/or viability of a *Neisseria meningitidis* cell include, but are not limited to, Mueller-Hinton media and the like. As can be appreciated, the order of steps of the subject methods in which comparing agent binding to a bacterial cell cultured in chemically defined and/or undefined media can be varied, and thus chosen by the user for a given end use.

The present disclosure also provides isolated antibody produced by the above methods, as well as an isolated cell line capable of producing an isolated antibody produced according to the method. Isolation and production in a cell line can be carried out by any number of procedures known in the art.

The present disclosure further provides methods to screen candidate agents (e.g. antibodies) effective in inhibiting TspB Ig binding by detecting the effect of the candidate agent on formation of polymeric structures of TspB (e.g. IGB domain thereof, such as that of NmB 1628). Where the candidate agents are antibodies, the antibodies may be elicited by administration of candidate antigen. The methods make use of the tendency of TspB polypeptides to aggregate into polymeric structures and their ability to be dispersed when contacted with antibodies that inhibit Ig-binding activity of TspB. For example, the methods involve contacting a candidate agent (e.g. antibody in an antiserum) with TspB and detecting the presence and/or amounts of polymeric structure in the reaction mixture formed after such contacting. Detection of polymeric structures can be accomplished by any suitable means, e.g., detection of aggregates in a reaction mixture using a light microscope. The reaction mixture can be provided in an aqueous solution and/or in a gel. Where the candidate agent disperses and/or inhibits aggregation of the present polypeptides relative to aggregation in the absence of the candidate agent, the candidate agent is identified as a candidate for inhibition of Ig-binding activity of TspB.

Kits

Also provided by the subject invention are kits for using the compositions disclosed herein and for practicing the methods, as described above. The kits may be provided for administration of a vaccine (e.g., prophylactic or therapeutic) against *N. meningitidis*. The kit can include one or more of the polypeptides disclosed herein or encoding-nucleic acids, which may be provided in a sterile container, and can be provided in formulation with a pharmaceutically acceptable excipient for administration to a subject. The polypeptides can be provided with a formulation of an anti-*N. meningitidis* vaccine that provides for production of anti-TspB antibodies (e.g., a formulation containing recombinant fragment of TspB, vesicles from a TspB-expressing strain cultured with human serum, and the like), where the polypeptides of the present disclosure may be formulated separately or in combination with such vaccine.

In addition to above-mentioned components, the kits can further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging), etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Materials and Methods

The following methods and materials were used in the Examples below.

Preparation of Catlin 6 Media.

The composition of the Catlin 6 media (CDM) was adapted from Fossa da Paz (Fossa da Paz et al. 2003 *Brazil. J. Micro.* 34:27-32). Media was prepared fresh prior to each experiment by combining pre-made stock solutions of the amino acids, salts, glucose and iron. The CDM was supplemented with five percent IgG depleted sera that was heat inactivated at 56° C. (CDM-dHuS) prepared as described below. It was observed that adding 2M glutamine (UCSF cell culture facility) decreased the doubling time of some Nm strains cultured in CDM and was, therefore, included in the preparation of CDM. Cysteine was excluded from the Catlin 6 formulation because it was found that Catlin media without cysteine resulted in more consistent growth rates for most Nm strains than media with cysteine.

Preparation of IgG-Depleted Human Complement.

A 5 ml Protein G column (HiTrap Protein G HP, GE Healthcare Bio-sciences, Piscataway N.J.) was fitted with sterilized luer lock valves and two 10 ml syringes on the top and bottom of the column 25 ml of sterile filtered Dulbeccos buffered saline with Ca+ and Mg+, 0.5% glucose (DPBS+glu) was used to wash the column which was then chilled for 20 minutes at 4° C. Serum was removed from −80° C. storage and thawed on ice. 5.5 mls of serum was loaded onto the column and was placed at 4° C. for 5 minutes. DPBS+glu was then applied to the column to displace IgG depleted serum. Approximately 5 mls of the depleted serum was collected and immediately placed on ice. An additional 5 mls of DPBS+glu was applied to the column until the flow through was completely clear. The Protein G bound IgG was eluted from the column with 0.1M histidine acetate, pH 2.7, 0.02% Tween 20. The first 1.5 mls of the flow through were discarded. The following 15 mls were collected and buffer exchanged for 2 mM histidine, pH 6, containing 0.002% Tween 20 and 24 mM sucrose using a PD 10 size exclusion column (GE Healthcare Bio-Sciences) and subsequently lyophilized Detection of Human IgG Binding to Nm Strains by Flow Cytometry.

Meningococcal strains (group W135 strain A22, group B strain NMB, group C strain 4243) were grown to an $OD_{620nm}$ of ~0.6 in Mueller-Hinton (MH; BD) media containing 0.25% (weight/volume) glucose, Catlin 6 (CDM) media (9), or Catlin 6 media supplemented with 5% (volume/volume) human (HuS) or mouse serum (MoS). The serum from human donors was heat inactivated by incubating the serum at 56° C. for 30 minutes (HuS) and depleted of IgG (dHuS) by passing the serum over a Protein G column as described above. The cells were pelleted, washed, and resuspended in 80% of the original volume in blocking buffer (PBS buffer containing 1% bovine serum albumin (Sigma)). The mixture of cells was incubated at 4° C. for 1 hr with periodic gentle agitation. The cells were pelleted and resuspended in 200 µl of a 1:200 dilution in blocking buffer of fluorescein isothiocyanate (FITC)-conjugated goat anti-human secondary antibodies. FITC-conjugated antibodies against IgG(H+L) F(ab')$_2$ and IgM (Jackson ImmunoResearch, West Grove, Pa.). After the secondary antibody was added, the tubes were incubated for 1 hr at 4° C. with periodic gentle agitation. The cells were pelleted and resuspended in 400 µl of PBS containing 0.5% formaldehyde (weight/volume), freshly made and filtered (Steriflip, Millipore, Billerica, Mass.). The samples were immediately analyzed by flow cytometry (BD FACSCalibur System, BD Biosciences, San Jose, Calif.).

Collection of Mice Antisera.

Groups of CD1 mice (6-8 wk old, Charles River Laboratories, Wilmington, Mass.) were immunized with 1, 5, 10 or 252 µg or 10 µg of total of TspB-IGB (i.e. TspB-IGB vaccine) in 50% saline/50% Freund's complete adjuvant (Pierce) emulsion, or 3.25 mg/ml alhydrogel (alum) (Brenntag Biosector, Frederikssund, Denmark) or saline alone by ip injection. Blood samples were obtained by lancet of the facial vein 40 days after each injection and tested by ELISA.

Booster doses were given at post 28 days with incomplete Freund's adjuvant (Pierce), alum or saline alone and titers of antisera obtained 14 days post immunization were evaluated. Antisera titers were determined by ELISA. The antisera from individual mice were pooled and all further experiments were done with the pooled antisera. ELISA plates are were prepared by diluting each TspB-IGB 1:200 to 10 µg/ml in PBS and adding 100 µl per well to a 96-well microtiter plate (Immulon II HB). The plates were stored overnight at 4° C. before use. The plates were washed with PBS buffer 5 times and blocked with PBS buffer containing 1% (weight/volume) of BSA (Blocking buffer) for one hour at ambient temperature. The antisera were added in Blocking buffer at 1:100 dilution, followed by serial 3-fold dilutions (in duplicate). After overnight incubation at 4° C., the plates were washed with PBS buffer 5 times and rabbit anti-mouse-alkaline phosphatase conjugate antibody (Zymed) diluted 1:3000 in Blocking buffer was added. After incubating one additional hour at ambient temperature, the plates were washed (5x) with PBS buffer and the bound antibody was detected by adding 1 mg/ml p-nitrophenyl phosphate substrate (Sigma-Aldrich) in 50 mM sodium carbonate buffer, pH 9, containing 1 mM MgCl$_2$. The absorbance at 405 nm after 30 minutes incubation at ambient temperature was measured using a Molecular Devices SpectraMax 340 microtiter plate reader. Antisera were tested against the TspB-IGB.

Purification of TspB IGB and IGB Pro Under Native Conditions.

Frozen cell pellets from 250 ml of cell culture were thawed and resuspended in 0.5% (weight/volume) octyl glucopyranoside (Calbiochem, San Diego, Calif.) dissolved in 20 ml of 50 mM Tris.HCl, 150 mM sodium chloride, pH 7.5 (TBS) and 20 ml of PBS containing 0.1 mM phenylmethanesulfonyl fluoride (PMSF) and 10 µg/ml DNAse (Sigma-Aldrich). The mixture was homogenized using a syringe fitted with an 18 G needle and a length of Teflon tubing by repeatedly forcing the solution back and forth through the needle. The homogenized solution was agitated at ambient temperature on a rocking platform for 20 min then centrifuged at 20,000×g for 10 minutes. The supernatant was discarded and the pellet was suspended in 0.5% (volume/volume) EmpigenTT (Calbiochem) dissolved in 10 ml of TBS and 10 ml of PBS containing 0.1 mM PMSF and 10 µg/ml DNAse. The homogenized solution was agitated at ambient temperature on a rocking platform for 20 min then centrifuged as above. The resulting supernatant was transferred to new tube, while the pellet was extracted a second time in 0.5% EmpigenTT containing solution and agitated at ambient temperature on a rocking platform for 5 min before pelleting again. The resulting supernatant was combined with the supernatant from the first EmpigenTT extraction, solid imidazole was added to a final concentration of 10 mM, and the solution was filtered through a 0.2µ filter (Steriflip, Millipore, Billerica, Mass.). The filtered solution was then passed through a 5 ml Ni Sepharose H isTrap high performance HP column (GE BioScience, Piscataway, N.J.) equilibrated with Lysis Buffer (50 mM sodium phosphate, pH 8, containing 300 mM NaCl, 10 mM imidazole, and 1% (volume/volume) EmpigenTT). The column was washed with 50 ml of Wash Buffer (50 mM sodium phosphate, pH 8, containing 300 mM NaCl, 20 mM imidazole and 1% (volume/volume) EmpigenTT) and TspB protein was eluted stepwise with Elution Buffer (50 mM sodium phosphate, pH 8, containing 300 mM NaCl, and 1% (volume/volume) EmpigenTT) containing first 125 mM imidazole (14 ml) then 250 mM imidazole (16 ml). 2 ml fractions were collected and analyzed by SDS-PAGE. Fractions containing purified TspB derivatives were combined, dialyzed against 0.9% NaCl and concentrated to 0.2 to 2 mg/ml protein using a YM-10 concentrator (Millipore).

Example 1

Detecting Human IgG Binding by Meningococcal Strains Cultured in the Presence of Human Serum Flow cytometry experiments were carried out to identify the growing conditions of bacterial cells that might affect the binding of human IgG to the surface of *Neisseria meningitidis* group W135 (NmW135) strain A22. In addition to binding experiments in which purified human IgG were added to certain samples, control cases included no addition and the addition of mouse serum.

The results for NmW135 strain A22 are shown in FIG. 1. The filled histograms show results for the test conditions indicated and the unfilled histograms are the negative controls without additives. When A22 cells were grown in MH media or CDM alone and purified human IgG from a donor (Donor 1) who lacks intrinsic serum bactericidal activity against the test strain was added during the binding experiment, no binding or slight binding of IgG was detected (FIG. 1A,B, respectively). The result shows that there are no antigens expressed by the bacteria under either culture condition that are reactive with antibodies purified from the serum. Again, when the bacteria were cultured in MH (FIG. 1C) supplemented with dHuS from the same donor source (Donor 1) of purified IgG, slight IgG binding was observed. However, when the bacteria were cultured in CDM supplemented with dHuS the fluorescence of a subpopulation of cells is shifted to the right (FIG. 1D) showing the presence of bound human IgG even though >99% of the IgG had been removed from the serum ([IgG]>2 µg/ml after depletion and dilution). The much lower population of IgG-positive cells for cells cultured in MH/dHuS (row C) compared to CDM/dHuS (row D) suggests that human serum induced expression of Ig binding activity is suppressed in MH media. Cells cultured in CDM supplemented with mouse serum (CDM/MoS) showed no binding of mouse IgG (FIG. 1E). Also, if the bacteria were cultured in the presence of MoS and purified human IgG was added, no binding of human IgG was observed (FIG. 1F). The result shows that factors in human serum eliciting the expression of Ig binding activity are not present in mouse serum. However, if the bacteria were cultured in the presence of human serum and then incubated with mouse serum, binding of mouse IgG was observed but the fluorescence is weaker (FIG. 1G). Thus, the Ig binding activity is not entirely specific for human IgG but requires human serum factors to trigger expression of Ig binding activity.

To show that the observed Ig binding activity is not the result of immune IgG recognizing an antigen only expressed when the bacteria are cultured in the presence of human serum, the bacteria were grown in CDMHuS supplemented with purified human Fc fragments (prepared from polyclonal human IgG) modified with a fluorescent tag (HuFc-FITC, obtained from Jackson ImmunoResearch Laboratories, West Grove, Pa.). As shown in FIG. 1H, the bacteria bind to the Fc domain alone. Binding is weaker since the Fc domain is competing with intact human IgG present in the culture media or may be weaker because the Fc domain does not represent the entire epitope, but it is clearly increased relative to the negative control of bacteria grown in CDM without dHuS (open histogram) in the presence of HuFc-FITC. Since the Fc fragment lacks a combining site, the observed binding cannot be the result of antibody binding to an antigen but rather an antigen binding the Fc domain. Further, evidence for an Ig binding is provided below in Example 2 where the protein is identified and it is shown that a recombinant subdomain (that is, the IGB domain described above) of the protein binds human and mouse IgA, IgG and IgM.

FIG. 2A shows the results of binding experiments using dHuS from two donors (Donor 1 and Donor 3) and human IgG binding by genetically and antigenically diverse group B (NMB) and C (4243) strains in addition to group W135 strains A22, M9262, and 4383 (FIG. 2B). The result shows that the HuS-dependent expression of the IgG binding protein is not unique to a specific donor and that IgG binding protein expression is not limited to strain A22. Given the genetic and antigenic diversity of the strains and the unlikely exposure of the donors and especially the mice to invasive Nm strains, it is unlikely that the donor sera contain antibodies reactive with a common antigen that is only expressed when the bacteria are cultured in the presence of human serum.

Example 2

Affinity Purification and Identification of a Human IgG Binding Protein Expressed by *Neisseria meningitidis* Bacteria Affinity purification of human IgG binding protein. NmW135 strain A22 cells were grown in MH or CDMHuS at 37° C. For each culture condition, 5 cultures of 7 mLs were started at an $OD_{620nm}$ 0.15 (MH) or 0.2 (CDMHuS). When the $OD_{620nm}$ reached ~0.6, the 5 cultures were combined and an additional 65 mL of the respective culture media was added for a total of 100 mL, and the incubation was continued until $OD_{620nm}$=0.6. The cells were centrifuged at 10,000×g for 30 minutes to pellet the cells. The cell pellets were washed (resuspended in buffer and centrifuged) two times in 10 mL of filtered (Steriflip, Millipore) PBS buffer. After the final wash, the cells in 2 mL aliquots were pelleted and frozen on dry ice.

One 2 mL aliquot of cells was defrosted and washed twice with PBS. After washing, the cell pellet was resuspended in 2 mL solubilization buffer (10 mM Tris, pH 7.8, containing 10 mM EDTA, 150 mM NaCl, 1% (weight/volume) Triton X-100, 0.2% (weight/volume) sodium deoxycholic acid, and 0.1% (weight/volume) sodium dodecylsulfate) and incubated at 37° C. for 60 minutes. The samples were centrifuged at 45,000×g for 60 minutes at 20° C. The supernatants were transferred to microfuge tubes (1 mL per immunoprecipitation) containing Protein A or G Sepharose CL-4B beads (Sigma) (Protein A: 3-4 mg beads preswollen in 50 µL of PBS, Protein G: used 50 µL of beads washed 3 times in PBS). The mixture of sample and beads were incubated overnight with rocking at 4° C. The beads were washed 5 times with solubilization buffer with 2 minute centrifugation to pellet the beads after each wash. After the final wash, the beads were suspended in 75 µL of sample buffer without 2-mercaptoethanol, and incubated at 100° C. for 5 minutes to release bound immunoglobulin and proteins. The samples were centrifuged as above for 3 minutes to pellet the beads and the supernatant was transferred to a new tube. 2 µL of 2-mercaptoethanol was added and the supernatant was heated to 100° C. for 5 minutes. The proteins eluted from the beads were resolved on 4%-12% SDS-PAGE gels (Novex precast gels from Invitrogen), which were stained with GelCode Blue (Pierce Chemical Co., Rockford, Ill.) following the manufacturers instructions and the bands in the gel were detected using a LI-COR Odyssey IR imager (Lincoln, Nebr.) as shown in FIG. 3.

Identification of the *Neisseria* Human IgG Binding Protein by MALDI-TOF Mass Finger Print Analysis.

Portions of GelCode Blue stained SDS-PAGE gels containing IgG-binding antigens immunoprecipitated as described above were excised using a clean razor blade and minced in siliconized tubes (Fisher Scientific). Stain was removed from the gel pieces by washing with 200 mM $NH_4HCO_3$ buffer containing 40% (volume/volume) acetonitrile three times for 10 minutes with agitation on a vortexer. The gel pieces were dried under vacuum for 30 min then rehydrated in a minimal amount of 25 mM $NH_4HCO_3$ buffer containing trypsin (12 ng/µl, Worthington, Lakewood, N.J.) and incubated at 37° C. overnight. The buffer solution and tryptic peptides extracted from in the gel pieces with 0.1% (volume/volume) trifluoroacetic acid (TFA) in 50% (volume/volume) acetonitrile were combined. After drying the eluted peptide solution in a spin-vac (Savant, Thermo-Fisher), the residue was resuspended in 4 µl of 0.1% TFA/50% acetonitrile. 1 µl of this solution was added to 3 µl of 0.1% TFA/50% acetonitrile saturated with α-cyano-4-hydroxycinnamic acid (Bruker Daltonics, Fremont, Calif.). 0.5 µl of the sample/matrix solution was spotted onto a stainless steel target plate (Bruker Daltonics, Billerica, Mass.) for MALDI-TOF analysis. MALDI-TOF (Autoflex, Bruker Daltonics) was performed in the positive ion reflector mode (30 shots $N_2$ laser). The mass spectrum was calibrated using external peptide standards (Bruker Daltonics). The error of the observed masses is estimated to be 0.1%. The set of observed peptide masses was analyzed using Mascot (matrixscience.com; Perkins D N et al. 1999 *Electrophoresis* 20:3551-3567). Once proteins were identified, expected masses of the proteolytic fragments were calculated using PeptideMass (Wilkins M R et al. 1997 *Electrophoresis* 20:3551-3567).

Figure 3:
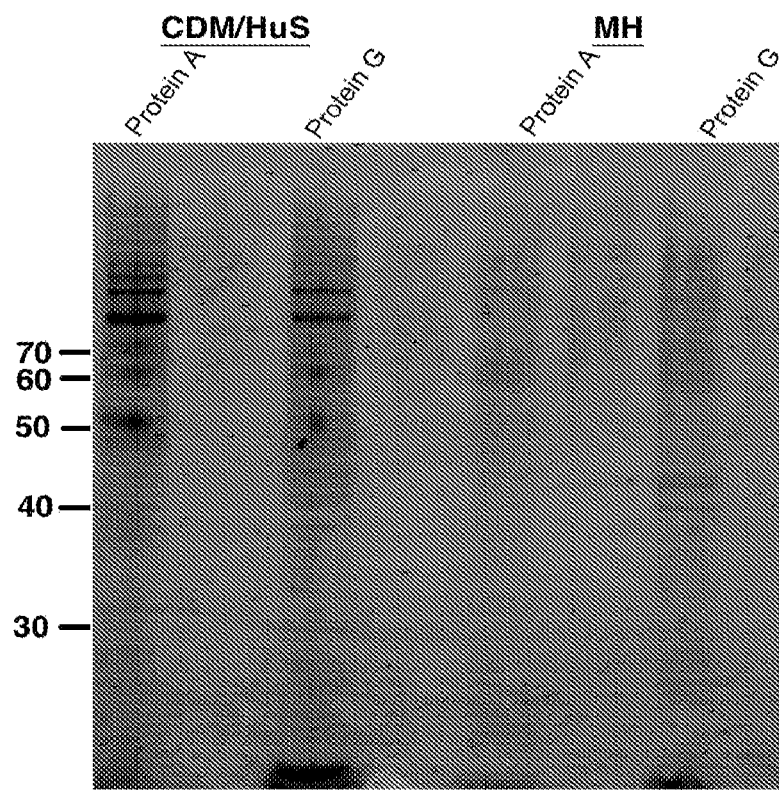
FIG. 3 is an image of a SDS-PAGE gel stained to detect proteins purified from MenW135 strain A22 when cultured in CDM supplemented with human serum (CDM/HuS) or in Mueller-Hinton media that contain IgG-binding activity that were eluted from Protein A or Protein G beads as indicated.

As shown in FIG. 3, proteins having a range of molecular mass were eluted from the Protein A and G beads incubated with solubilized cells grown in CDM/dHuS but not MH. However, when the tryptic peptides from each protein band isolated from the gel were analyzed by MALDI-TOF mass spectroscopy, all of them contained a similar set of masses indicating the presence of a single protein migrating in the gel with variable mobility (FIG. 3). The identity of the protein determined by mass finger print analysis using Mascot (FIG. 4) was found to be that encoded by NmA strain Z2491 gene NMA0776 with a probability based Mowse score of 64 (values >50 are significant) and corresponding expectation value of 0.0026 (values <0.05 are significant). NMA0776 and a homologous gene, NMA1797, from the NmA strain Z2491 genome share sequence homology with T and B cell stimulating protein B identified by Ala'Aldeen and coworkers (Kizil G I et al. 1999 *Infect. Immun.* 67:3533-3541; U.S. Pat. No. 6,861,507) and Orf6 identified by Bille E et al. 2005 *J. Exp. Med.* 201:1905-1913 and Bille E et al. 2008 PLoS One 3:e3885.

Example 3

Sequence Analysis and Structural Model of *Neisseria* Human IgG Binding Protein

Using the translated protein sequence of NMA0776 and the BLAST sequence homology search of 13 Neisseriaceae genomes available at NCBI (ncbi.nlm.nih.gov/sutils/genom_table.cgi), homologous protein sequences were found in invasive meningococcal group A (Z2491), B (MC58), and C (FAM18) and *Neisseria gonorrhoeae* (FA1090) strains and non-invasive *Neisseria lactamica* (ATCC 23970) strains. The number of genes encoding putative TspB/Orf6 proteins ranged from 1 partial sequence (lactamica strain ATCC 23970) to 4 full length sequences (meningococcal group B MC58 group C FAM18 and *N. gonorrhoeae* strain FA1090). When the translated protein sequences from group A, B, and C strains were compared, a pattern emerged.

As shown in FIG. 5, the sequences of the amino and carboxyl terminal ends of the proteins are divergent but there is a core region that is relatively conserved. The variable amino terminal sequences are potentially functional leader peptide sequences that direct the nascent protein to be transported out of the cell. At the carboxyl terminal end of the proteins, the variable sequences are generally hydrophobic membrane spanning segments that may not have to have the same sequence to be functionally equivalent. As for the conserved internal domains, there is a typical globular domain that is made up mainly of beta sheet structure based on secondary structure prediction followed by a proline-rich segment. Proline-rich segments are known to adopt extended helical structures (Butcher D J et al. 1996 *Biochemistry* 35:698-703).

According to the analysis, at least some TspB/Orf6 genes encode a protein that can be exported to the bacterial surface. The protein contains a highly variable N-terminal domain followed by globular domain extending out from the membrane at the end of the proline-rich helical segment that is anchored to the membrane by a variable membrane spanning segment. Based on this structural model, it is apparent that the globular and/or proline-rich segments have some functional activity since they are highly conserved while the variable N-terminal domain serves as a dispensable "disguise" for subverting antibody responses. Accordingly, a vaccine designed to elicit antibodies targeting TspB/Orf6 may contain only one or both conserved domains.

Example 4

Cloning and Expression of Various Ig Binding Constructs Containing the Constant Region Domain of *Neisseria* Human IgG Binding Protein The conserved globular domain (CR) was cloned as described below (referred to herein as TspB-IGB). Genomic DNA was prepared from strain MC58 using a Qiagen genomic DNA isolation kit (Qiagen, Valencia, Calif.) following the manufacturers instructions. DNA encoding TspB-IGB was amplified by PCR using the following primers: 5'-CATGGATCCATCAGTTTCCCG-3' (SEQ ID NO: 49) and 5'-CATAAGCTTTGCTTCCGCGCTTC-3' (SEQ ID NO: 50). PCR consisted of 30 cycles of denaturation at 95° C., annealing at 50° C., and elongation at 72° C. with an Idaho Technology (Salt Lake City, Utah) RapidCycle thermocycler, employing the Pfx DNA polymerase, nucleotides and the buffers from Invitrogen (Carlsbad, Calif.). The PCR fragment was purified using a QIAquick PCR purification kit following the manufacturers instructions and ligated into plasmid pCR2.1 (Invitrogen) using T4 DNA ligase (New England Biolabs, Ipswich, Mass.) overnight at 20° C. The ligation reaction products were used to transform *E. coli* strain BL21 (DE3) (Invitrogen). The transformed *E. coli* were plated on LB agar plates containing 100 µg/ml ampicillin (Sigma) and Blue White Select screening reagent (Sigma). Plasmid was prepared from white colonies using a Qiagen mini-plasmid prep kit and the presence of the TspB-IGB DNA fragment was confirmed as described below.

The plasmid was first digested with Eco RI (New England Biolabs) to confirm the size of the inert. Fragment used in cloning was treated with the restriction endonucleases Hind III followed by Bam HI (New England Biolabs). The resulting fragment was isolated by electrophoresis in a 1% (weight/volume) agarose (Promega, Madison, Wis.) gel containing 0.5 µg/ml ethidium bromide in TBE buffer (Gibco). The band corresponding to the expected size of the TspB-IGB DNA fragment was isolated by excision from the gel and purified using a Qiagen QIAquick Gel Extraction kit. The Hind III/BamHI TspB-IGB DNA fragment was ligated as before into expression plasmids pQE31 (Qiagen) and pET21b(+) (Novagen now EMD, Gibbstown, N.J.) that were previously digested with the same restriction endonucleases, treated with shrimp alkaline phosphatase (USB, Cleveland, Ohio) and purified by agarose gel electrophoresis as described above. DNA products from the ligation reaction was used to transform strain BL21(DE3), which was plated on LB agar/ampicillin plates as described above. Plasmid DNA was prepared from transformants and the presence of the correct insert was confirmed by restriction endonuclease digestion and DNA sequencing.

The plasmid pQE31 allowed for a high level of intracellular expression of TspB-IGB with a His tag (that is a segment containing six histidine residues) at the amino terminus. On the other hand, expression from plasmid pET22b(+) would incorporate a His tag at the carboxyl terminus of TspB-IGB and a pelB leader peptide at the amino terminus of TspB-IGB, which directs the protein for secretion into the periplasm. The advantage of plasmid pQE31 includes very high levels of protein expression while plasmid pET22b(+) allows for native folding in the extracellular periplasmic space. The TspB-IGB containing plasmid constructs were transformed into *E. coli* strain BL21(DE3) (Invitrogen). Individual colonies were grown overnight in 50 ml of LB media containing 100 µg/ml ampicillin at 37° C. in a shaking incubator. The next day, the overnight cultures were used to inoculate 500 ml of 2×YT media at 37° C. in a shaking incubator. When the $OD_{620nm}$ was between 0.5 and 1 for cells containing the pQE31-TspB-IGB construct, IPTG (Sigma) was added to a final concentration of 1 mM and amplicillin to 200 µg/ml. The culture was continued for 3 hrs and the cells harvested by centrifugation at 8000×g for 20 minutes, the supernatant was discarded and the cell pellet frozen at −80° C. until processed as described below. The culture of BL21(DE3) containing the pET22b(+)-TspB-IGB plasmid was cooled to 22° C. when the OD$_{620nm}$ was approximately 0.6. IPTG and ampicillin were added to 1 mM and 200 µg/ml final concentrations, respectively, and the culture was continued at 22° C. overnight. The cells were recovered by centrifugation and frozen until used as described below.

Based on the methods described above, several constructs for expressing recombinant TspB were made. NmB strain MC58 has three TspB genes: NMB1548, NMB1628, and NMB1747. The NMB1628 and NMB1747 TspB genes encode polypeptides having identical amino acid sequences. Sequence derived from NMB1628 was cloned in the pQE vector (with an N-terminal HisTag) and the sequences derived from NMB1548 were cloned into both the pQE vector and the pET vector (with a C-terminal HisTag).

Additional versions of constructs that were made included: 1) NMB1628 constant region and proline repeat, referred to herein as IGBPro and full length NMB1628 in both pQE and pET vectors. See details below.

1) TspB from NMB1628 Containing IGBpro:

A DNA fragment spanning the conserved globular domain followed by the conserved proline-rich repeat of NMB1628 was cloned as described below (referred to herein as TspB-IGBpro). Genomic DNA was prepared from strain MC58 using the Qiagen genomic DNA isolation kit (Qiagen, Valencia, Calif.) following the manufacturers instructions. DNA encoding TspB-IGBpro (NMB1628) was amplified by PCR using the following primers: 5'-CATGGATCCAT-CAGTTTCCCGCGCCGCCGTCTT-3' (SEQ ID NO: 51) and 5'-CATAAGCTTGTTCTCAAAGCTGAACGCG-3' (SEQ ID NO: 52). PCR consisted of 5 cycles of denaturation at 95° C., annealing at 48° C., and elongation at 72° C., followed by 25 cycles of denaturation at 95° C., annealing at 52° C., and elongation at 72° C., with an Idaho Technology (Salt Lake City, Utah) RapidCycle thermocycler, employing the Taq DNA polymerase, nucleotides and reaction buffers from New England Biolabs (Ipswich, Mass.). The PCR fragment was purified using a QIAquick PCR purification kit (Qiagen) following the manufacturers instructions. Using the TOPO-TA cloning kit (Invitrogen) as per manufacturers instructions, the PCR products were ligated into plasmid pCR2.1 (Invitrogen) and ligation reaction products were used to transform E. coli strain TOP 10 (Invitrogen). The transformed E. coli cells were plated on LB agar plates containing 100 µg/ml ampicillin (Sigma) and X-Gal (bromo-chloro-indolyl-galactopyranoside, Gold Biotechnology). To screen for white colonies carrying plasmid DNA with the correct insert, ruling out amplification and integration of TspB-IGBpro from the other two genomic loci (NMB1548 and NMB1747), colony PCR using verification primers 5'-GCCGCCGTCT-TGTCAGGAGTC-3' (SEQ ID NO: 53) and 5'-ATCAAGCA-CAGTCACTGTGAA-3' (SEQ ID NO: 54) was performed. Plasmid DNA was then prepared from chosen transformants using a Qiagen mini-plasmid prep kit and the correct sequence encoding TspB-IGBpro was verified by DNA sequencing.

The insert-carrying plasmid pCR2.1 was digested with restriction endonucleases Bam HI and Hind III (New England Biolabs). The resulting fragment was isolated by electrophoresis in a 1.5% (weight/volume) agarose (Promega, Madison, Wis.) gel in TAE buffer (40 mM Tris acetate, 1 mM EDTA). After electrophoresis DNA bands were visualized by submerging the agarose gel in 0.5% ethidium bromide solution (Gibco). The band corresponding to the expected size of the TspB-IGBpro DNA fragment was isolated by excision from the gel and purification using a Qiagen QIAquick Gel Extraction kit. The Bam HI/Hind III TspB-IGBpro DNA fragment was ligated into expression plasmid pQE31 (Qiagen) that was previously digested with the same restriction endonucleases and treated with shrimp alkaline phosphatase (USB, Cleveland, Ohio). The ligation reaction was then used to transform strain BL21(DE3) (Invitrogen), which was plated on LB agar/ampicillin plates as described above. To select colonies carrying plasmid DNA with the correct insert colony PCR using verification primers 5'-GCCGC-CGTCTTGTCAGGAGTC-3' (SEQ ID NO: 53) and 5'-AT-CAAGCACAGTCACTGTGAA-3' (SEQ ID NO: 54) was performed. DNA was then prepared from chosen transformants and the correct sequence encoding TspB-IGBpro was verified by DNA sequencing.

2) Full-Length TspB from NMB1628 (TspB-FL)

The full length open reading frame (start to stop codon) of NMB1628 was cloned as described below (referred to herein as TspB-FL). Genomic DNA was prepared from strain MC58 using the Qiagen genomic DNA isolation kit (Qiagen, Valencia, Calif.) following the manufacturers instructions. DNA encoding TspB-FL was amplified by PCR using primer pair 5'-AGCATATGTTGGGGATGTTTTCGGT-3' (SEQ ID NO: 55) and 5'-AGAAGCTTGACTTCACGAGATACTGTGC-3' (SEQ ID NO: 56) for cloning into plasmid pET22b(+), and 5'-ACGGATCCTTGGGGATGTTTTCGGTTAA-3' (SEQ ID NO: 57) and 5'-AGAAGCTTCTAGACTTCAC-GAGATACTG-3' (SEQ ID NO: 58) for cloning into plasmid pQE30. PCR for both amplification reactions consisted of 5 cycles of denaturation at 95° C., annealing at 48° C., and elongation at 72° C., followed by 25 cycles of denaturation at 95° C., annealing at 52° C., and elongation at 72° C., with an Idaho Technology (Salt Lake City, Utah) RapidCycle thermocycler, employing the Taq DNA polymerase, nucleotides and reaction buffers from New England Biolabs (Ipswich, Mass.). The PCR fragments were purified using a QIAquick PCR purification kit (Qiagen) following the manufacturers instructions. Using the TOPO-TA cloning kit (Invitrogen) as per manufacturers instructions, the PCR products were ligated into plasmid pCR2.1 (Invitrogen) and ligation reaction products were used to transform E. coli strain TOP 10 (Invitrogen). The transformed E. coli cells were plated on LB agar plates containing 100 µg/ml ampicillin (Sigma) and X-Gal (Gold Biotechnology). Plasmids were prepared from white colonies that generated PCR products during colony PCR with the primers used for initial amplification of TspB-FL fragments using a Qiagen mini-plasmid prep kit. Correct TspB-FL insert sequences were confirmed via DNA sequencing.

The plasmids were digested with the restriction endonucleases Nde I and Hind III, or Bam HI and Hind III (New England Biolabs) to liberate the fragments used for cloning into vectors pET22b(+) and pQE30, respectively. The resulting fragments were isolated by electrophoresis in a 1.5% (weight/volume) agarose (Promega, Madison, Wis.) gel in TAE buffer (40 mM Tris acetate, 1 mM EDTA). After electrophoresis DNA bands were visualized by submerging the agarose gel in 0.5% ethidium bromide solution (Gibco). The bands corresponding to the expected sizes of the TspB-FL DNA fragment were isolated by excision from the gel and purified using a Qiagen QIAquick Gel Extraction kit. The Nde I/Hind III and Bam HI/Hind III TspB-FL DNA fragments were ligated into the expression plasmids pET22b(+) and pQE30 (Qiagen), respectively, which were previously digested with the same restriction endonucleases and treated with shrimp alkaline phosphatase (USB, Cleveland, Ohio). DNA products from the ligation reactions were used to transform E. coli strain TOP 10 F' cells (Invitrogen), which were plated on LB agar/ampicillin plates as described above. Plasmids were prepared from transformants that generated PCR products during colony PCR, as described above, using a Qiagen mini-plasmid prep kit. Correct TspB-FL insert sequences were again confirmed via DNA sequencing.

3) TspB IGB from NMA 0776 and 1797:

The conserved globular domains TspB-IGB encoded by NMA0776 and NMA1797 were cloned as described above for the TspB-IGBpro encoded by NMB1628 in MC58. Genomic DNA was prepared from strain Z2491 using a Qiagen genomic DNA isolation kit (Qiagen, Valencia, Calif.) following the manufacturers instructions. DNA encoding TspB-IGB of NMA0776 was amplified by PCR using the following primers: 5'-CATGGATCCATCAGTATC-CCGCGCCG-3' (SEQ ID NO: 59) and 5'-CAT-AAGCTTTGCTTCTGCGCTTCCG-3' (SEQ ID NO: 60), while DNA encoding TspB-IGB of NMA1797 was amplified by PCR using the following primers: 5'-CATGGATCCAT-CAGTTTCCCGCGCCG-3' (SEQ ID NO: 61) and 5'-CAT-AAGCTTTGCTTCCGCGCTTC-3' (SEQ ID NO: 62). PCR for both amplification reactions consisted of 5 cycles of denaturation at 95° C., annealing at 48° C., and elongation at 72° C., followed by 25 cycles of denaturation at 95° C., annealing at 52° C., and elongation at 72° C., with an Idaho Technology (Salt Lake City, Utah) RapidCycle thermocycler, employing the Taq DNA polymerase, nucleotides and reaction buffers from New England Biolabs (Ipswich, Mass.). The PCR fragments were purified using a QIAquick PCR purification kit (Qiagen) following the manufacturers instructions. Using the TOPO-TA cloning kit (Invitrogen) as per manufacturers instructions, the PCR products were ligated into plasmid pCR2.1 (Invitrogen) and ligation reaction products were used to transform E. coli strain TOP 10 (Invitrogen). The transformed E. coli were plated on LB agar plates containing 100 μg/ml ampicillin (Sigma) and X-Gal (Gold Biotechnology). Plasmids were prepared from white colonies that generated PCR products during colony PCR with the primers used for initial amplification of TspB-IGB encoded by NMA0776 and NMA1797 using a Qiagen mini-plasmid prep kit. Correct TspB-IGB insert sequences were confirmed via DNA sequencing.

Plasmids carrying both TspB-IGB insertions sequences were digested with restriction endonucleases Bam HI and Hind III (New England Biolabs) to liberate the two fragments used in cloning. The resulting fragments were isolated by electrophoresis in a 1.5% (weight/volume) agarose (Promega, Madison, Wis.) gel in TAE buffer (40 mM Tris acetate, 1 mM EDTA). After electrophoresis DNA bands were visualized by submerging the agarose gel in 0.5% ethidium bromide solution (Gibco). The bands corresponding to the expected sizes of the TspB-IGB DNA fragments were isolated by excision from the gel and purified using a Qiagen QIAquick Gel Extraction kit. The Hind III/BamHI TspB-IGB DNA fragments were ligated into expression plasmid pQE31 (Qiagen) that was previously digested with the same restriction endonucleases and treated with shrimp alkaline phosphatase (USB, Cleveland, Ohio). The ligation reactions were used to transform E. coli strain TOP 10 F' (Invitrogen), which was plated on LB agar/ampicillin plates as described above. Plasmid DNA was prepared from colonies that generated PCR products during colony PCR with the primers used for initial amplification of the two TspB-IGB fragments using a Qiagen mini-plasmid prep kit. Correct TspB-IGB insert sequences were confirmed via DNA sequencing.

Example 5

Purification of Recombinant TspB-IGB

Figure 6:
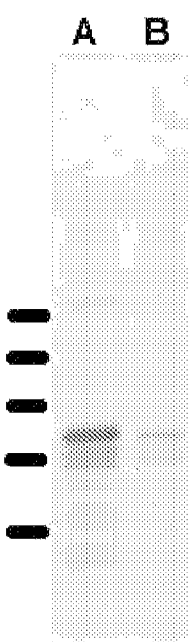
FIG. 6 shows the purification products from expressing TspB-IGB from pQE31 purified under denaturing conditions (lane A) and pET22b(+) purified under native conditions from the periplasm (lane B).

Purification of the TspB-IGB proteins was performed using a 5 ml Ni Sepharose HisTrap high performance HP column (GE BioScience, Piscataway, N.J.) under denaturing conditions for pQE31-TspB-IGB expression plasmid or native conditions for pET22b(+)-TspB-IGB expression plasmid, as described in the Qiaexpressionist Handbook 5$^{th}$ Edition (2003, Qiagen). Fractions from the column were analyzed by SDS-PAGE using precast gels from Invitrogen followed by staining with SimplyBlue SafeStain (Invitrogen) and documented by scanning the gel with on Odyssey IR scanner (LI-COR). Fractions containing TspB-IGB purified under denaturing conditions were combined (6 ml total) diluted to 30 ml in 100 mM $NaH_2PO_4$ buffer, pH 8.0, containing 10 mM Tris.HCl, and 8M urea and dialyzed (1 kDa cutoff Spectropor membrane, Fisher) in PBS buffer (1 L total) at ambient temperature by adding 25 ml of PBS buffer at a time over the course of 1 day. Finally, the refolded TspB protein was dialyzed in 4 L of 2 mM histidine, pH 6, containing 0.002% Tween 20 and 24 mM sucrose and lyophilized TspB-IGB purified under native conditions (pET22b(+)-TspB-IGB construct) was dialyzed in 4 L of 2 mM histidine, pH 6, containing 0.002% Tween 20 and 24 mM sucrose and lyophilized As shown in FIG. 6, the purification products expressed from either the pQE31 or the pET22b(+) plasmids demonstrated that both methods described above can produce TspB-IGB polypeptides of high purity. FIG. 6, lane A shows TspB-IGB expressed from pQE31 and purified under denaturing conditions and refolded. FIG. 6, lane B shows TspB-IGB expressed from pET21b(+) purified under native conditions from the periplasm.

Example 6

Ig Binding Activity of Recombinant TspB-IGB

TspB-IGB polypeptides produced and purified under denaturing conditions then refolded or purified under native conditions were evaluated by solid phase ELISA assay for their abilities to bind to IgG from various sources. TspB-IGB (100 μl/well at a concentration of 10 μg/ml in PBS) was adsorbed to microtiter plates (Immulon 2; Dynatech Laboratories, Inc., Chantilly, Va.) overnight at 4° C. After washing three times with PBS, the plates were blocked with 250 μl of blocking buffer (PBS containing 1% bovine serum albumin and 0.1% sodium azide, pH 7.4) for 30 to 60 minutes at room temperature. After washing the plates three times with PBS, human serum from four different donors (Donors 1, 3, 4, and 5), IgG purified from Donor 3 and Donor 1 serum, purified human IgG, IgM, and IgA from Jackson ImmunoResearch Laboratories (West Grove, Pa.), purified human IgG1, IgG2, IgG3 and IgG4 obtained from myeloma cell lines (BioDesign International, Saco, Me.) and produced in CHO cells (mAb DA2 from our lab), mouse serum from four mice and from Zymed (South San Francisco, Calif.), and purified mouse IgG1, IgG2a, IgG2b, IgG3 and IgM mAbs obtained from mouse myeloma (all from Southern Biotech, Birmingham, Ala.) and hybridoma (SEAM 12) a cell line was added to the wells and serially diluted in blocking buffer. On the following day, the wells were washed five times with PBS and were incubated for one hour at ambient temperature with 100 μl/well of alkaline phosphatase-conjugated anti-human (Jackson ImmunoResearch, West Grove, Pa.) or anti-mouse polyclonal antibody (IgA+IgG+IgM; Zymed, South San Francisco, Calif.) diluted 1:3000 in blocking buffer. The plates were then washed with PBS, and 100 μl of freshly prepared substrate (p-Nitrophenyl phosphate; Sigma) diluted to 1 mg/ml in substrate buffer (50 mM $Na_2CO_3$, 1 mM $MgCl_2$, pH 9.8) was added to each well. Absorbance values at 405 nm were measured after approximately 60 minutes. The IgG antibody concentration in each sample was determined by capture ELISA (Southern Biotech for mouse and Immunological Consultants for human). Table 1 below summarizes the binding data.

TABLE 1

Antibody binding to recombinant TspB-IGB by ELISA

| Human | | Mouse | |
|---|---|---|---|
| Antibody (source) | BC (μg/ml)* | Antibody (source) | BC (μg/ml)* |
| Donor 4 serum | 10 | MoS#1 serum | 19 |
| Donor 5 serum | 4 | MoS#2 serum | 16 |
| Donor 1 serum | 2.3 | MoS#3 serum | 21 |
| Donor 3 serum | 1.4 | MoS#4 serum | 5 |
| Purified Donor 1 IgG | 4.5 | MoS (serum, Zymed) | 33 |
| Purified Donor 3 IgG | 1.1 | | |
| Purified IgG (Jackson ImmunoResearch) | 1.4 | | |
| IgG1 (myeloma) | >50 | IgG1 (myeloma) | >100 |
| IgG2 (myeloma) | >50 | IgG2a (myeloma) | >100 |
| IgG3 (myeloma) | >50 | IgG2b (myeloma) | >100 |
| IgG4 (myeloma) | 50 | IgG3 (myeloma) | >100 |
| IgM (myeloma) | 0.6 | IgM (myeloma) | >100 |
| IgA (serum) | 22 | | |
| DA2 (IgG1) | 33 | SEAM 12 (IgG2a) | 0.4 |

*BC, concentration of antibody giving an $OD_{405\,nm}$ of 0.5 after 60 min development with substrate. Antibody concentrations in stock solutions were measured by capture ELISA except for Ig standards, which were provided by the manufacturer. DA2 was produced in CHO cells and SEAM 12 in a hybridoma cell line. Negative control was BSA, which was the same as secondary only at data point dilution.

All of the polyclonal human antibody preparations whether in serum or purified show binding to both native and refolded TspB-IGB compared to the negative control BSA alone (Table 1). However, binding by the human and mouse IgG standard mAbs obtained from commercial sources that were produced in myeloma cell lines showed little or no binding except for a human IgM paraprotein obtained from Jackson ImmunoResearch. In contrast, binding was observed for a humanized IgG1 mAb produced in CHO cells (DA2) and a mouse IgG2a mAb produced in a hybridoma cell line (SEAM 12). The results show that the recombinant TspB-IGB contains at least a portion of the IgG binding functional activity of full length TspB and that TspB-IGB can bind both human and mouse IgG. There may be a preference for human Ig as the concentrations of Ig giving equivalent ELISA readings were 5-10-fold lower for human Ig. Also, the fluorescence of cells in the presence of mouse Ig was lower than in the presence of human Ig (compare FIG. 1, D and G). The reasons for the apparent lack of reactivity with some of the commercially obtained isotype standards is unclear but may have to do with differences in Fc glycoforms that occur in myelomas (Farooq M et al. 1997 *Glycoconj J.* 14:489-492). Alternatively, other domains of the full length TspB protein that are absent in TspB-IGB may contribute to binding. For example, the proline-rich segment may promote the formation of multimers that would be expected to exhibit greater avidity than monomeric forms.

Binding to Human IgG by NMB1628-Encoded TspB v. NMB1548-Encoded TspB

Binding of purified human IgG to recombinant TspB1628IGB and TspB1548IGB. TspB IGB proteins encoded by NMB1628 and NMB1548, expressed from the pQE plasmid with a HisTag at the amino terminus, and purified under native conditions were adsorbed (100 μl of 10 μg/ml) to the wells of a microtiter plate as described above. After blocking with Blocking Buffer, serial dilutions of purified human IgG in Blocking Buffer were added to the wells and left at 4° C. overnight. The plates were washed and bound IgG was detected as described above. As a control, antisera to refolded TspB1628IGB (rfTspB1628IGB), which binds equally well to TspB1628IGB and TspB1548IGB was used to show that equivalent amounts of protein were coated on the plates.

FIG. 11 shows that TspB IGB encoded by NMB1628 bound strongly to purified human IgG while TspB IGB encoded by NMB1548 bound human IgG poorly.

Solutions of purified TspB1628IGB were observed to have a gel like precipitate while solutions of purified TspB1548IGB appeared not to contain a similar gel-like material. The respective solutions were spotted onto a microscope slide, covered with a glass cover slip and allowed to dry overnight. When the slide were examined the next day, the TspB1628IGB sample was observed under a microscope (Zeiss Axioplan) to contain an extensive network of distinctive polymeric structures. In contrast, only a few shorter polymeric structures were observed for the TspB1548IGB sample. The differing ability of the two derivatives to form polymeric structures may be related to their differing ability to bind human IgG. FIG. 12 shows that TspB IGB encoded by NMB1628 (FIG. 12, panel A) aggregated to form distinctive polymeric structures while TspB IGB encoded by NMB1548 (FIG. 12, panel B) formed limited polymeric structures or not at all. Thus, the ability of TspB IGB derivatives to form polymeric structures can be associated with the ability to bind human IgG.

Example 7

Selection of Bacteria that Express TspB

Figure 13:
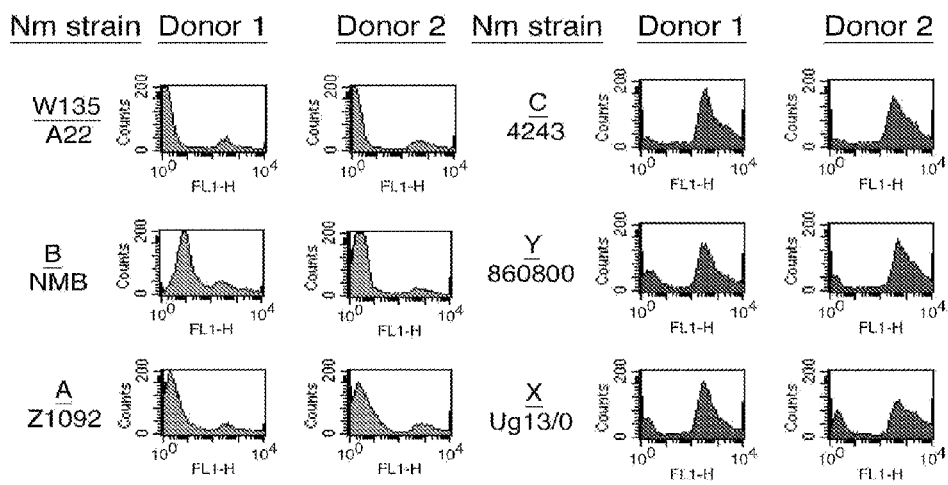
FIG. 13 are flow cytometry experiments showing binding of various *Neisseria* bacteria strains to human IgG from Donor 1 and Donor 2 sera.
Figure 14:
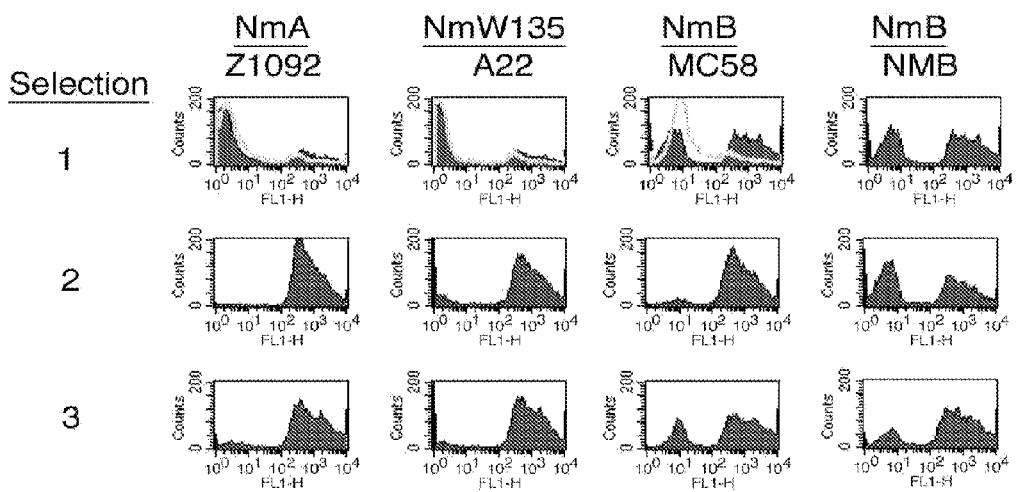
FIG. 14 are flow cytometry experiments monitoring the selection of various strains of *Neisseria* bacteria for the IgG-binding ability.

FIG. 13 shows the ability of several *N. meningitidis* strains from different capsular groups to bind human IgG from two different donor sera (Donor 1 and Donor 2) as determined by flow cytometry (Example 1). Some of the strains (e.g. NmC strain 4243) bound to IgG strongly while other (e.g. NmW135 stain A22) had little or no binding. Strains A22, NMB, and Z1092, which showed little or no IgG binding were subjected to selection in the presence of human complement as follows.

Bacterial colonies growing on chocolate agar (Remel, Lenexa, Kans.) were used to inoculate a 5 ml culture of Catlin 6 media containing 5% (volume/volume) heat inactivated IgG depleted human serum (CDMHuS) (prepared as described in Materials and Methods) to an $OD_{620nm}$ of 0.18 and were grown at 37° C. to an $OD_{620nm}$ of 0.72. The culture was centrifuged to collect the bacteria, which were suspended in the same volume of culture media. A portion of bacterial solution was diluted 1:80,000 in 1 ml of CDM containing 20% (volume/volume) human complement. The bacteria were grown overnight at 37° C. The next morning, the bacteria were diluted to an $OD_{620nm}$ of 0.18 in 5 ml of CDMHuS and grown again to an $OD_{620nm}$ of 0.72. The procedure was repeated two times and the bacteria obtained after each round of overnight selection in 20% human complement were analyzed for IgG binding by flow cytometry.

As shown in FIG. 14, the fraction of cells that were positive for IgG binding increased with each round of selection. For reference in FIG. 14, IgG binding to the strain before selection (FIG. 13) is shown in the unfilled histogram. Expression of IgG binding activity could be variable in bacteria that were not grown in the presence of human serum factors. However, IgG binding was restored by repeated culture in human serum containing active complement. Bacteria used for measuring binding and to be used for bactericidal activity (BCA) of anti-TspB-IGB antibodies described in the Examples below were selected using the methods described in this Example. The bacteria were stored for future use by suspending the bacteria grown in 5 ml of CDMHuS in 200 µl of whole human serum then freezing 20 µl aliquots on dry ice. The bacterial aliquots were stored at −80° C. until used.

Example 8

Evaluating Binding of Antisera to *Neisseria meningitidis* Bacteria

Antisera were collected from immunized mice as described above in the Materials and Methods section. Mice was immunized with the following:
1) NMB1628IGB expressed in pQE purified under denaturing and native conditions (rfTspB1628IGB)
2) NMB1628 IGBPro produced from pQE and purified under native conditions (nTspB1628IGB); and
3) NMB1548 produced from pET and purified under native conditions (nTspB1548IGB).

The ability of the TspB-IGB-based vaccines to elicit antibodies that bind to *Neisseria* was tested by flow cytometry. The *Neisseria* strains were grown to an O.D.$_{620}$ of ~0.6 in CDM or CDMHuS so that cells were induced to express TspB/Orf6 can be compared to uninduced cells. The cells were pelleted, washed, and resuspended in 80% of the original volume in blocking buffer. The bacterial suspension was then added to the reaction mixture such that the final concentrations will be 50% bacterial suspension, 10% antiserum, and 40% blocking buffer. The mixture was incubated at 4° C. for 2 hr with periodic gentle agitation. The cells were pelleted by centrifugation and resuspended in 100 µl of a 1:300 dilution in blocking buffer of fluorescein isothiocyanate (FITC)-conjugated goat anti-mouse secondary antibodies. FITC-conjugated antibodies against IgG(H+L) F(ab')$_2$ and IgM (Jackson ImmunoResearch, West Grove, Pa.) as well as IgG1, IgG2a, IgG2b, and IgG3 (Bethyl Laboratories, Montgomery, Tex.) was used. After the secondary antibody was added, the tubes were incubated for one hour at 4° C. with periodic gentle agitation. The cells were pelleted and resuspended in 450 µl of PBS containing 0.5% formaldehyde (weight/volume), freshly made and filtered. The samples were then analyzed by flow cytometry (BD FACSCalibur System, BD Biosciences, San Jose, Calif.).

Figure 15:
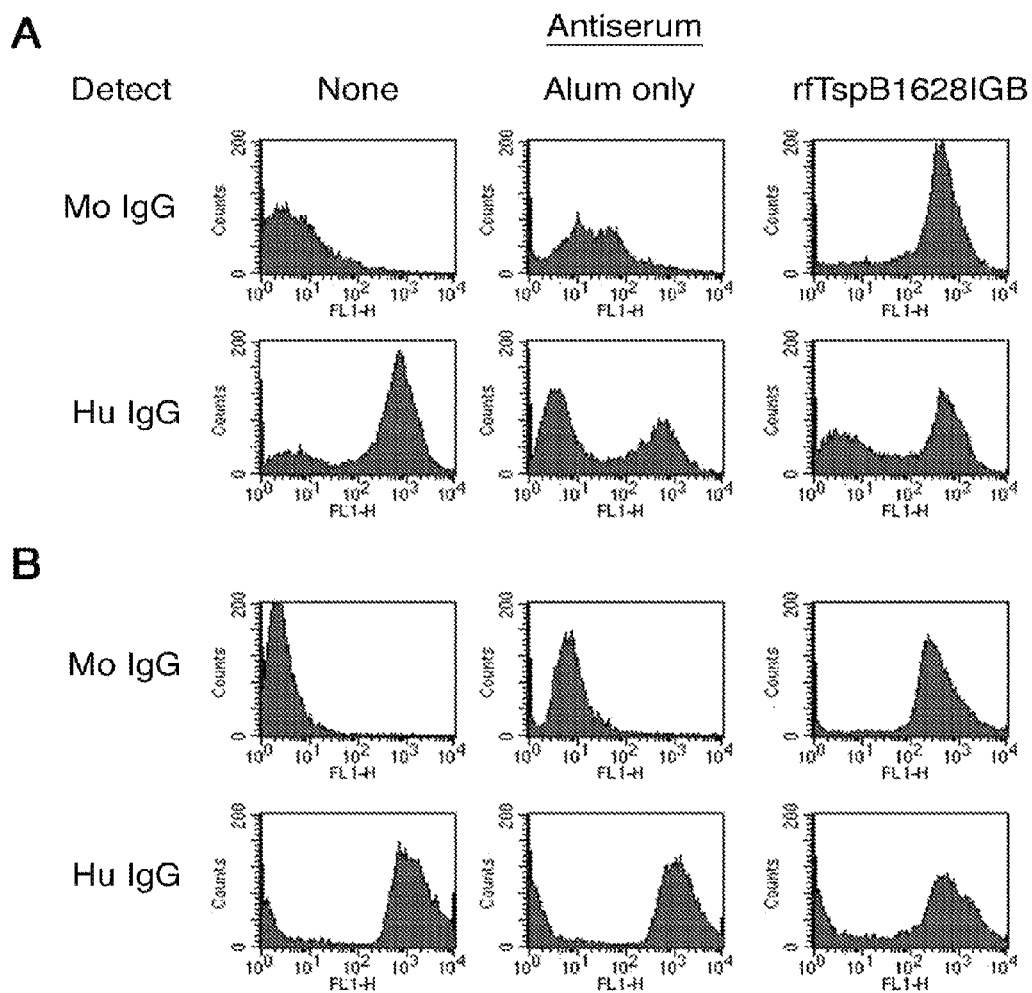
FIG. 15 shows the binding of sera from mice immunized with partially denatured TspB1628IGB to NmB strain MC58 (panel A) and to NmA strain Z2491 (panel B).

FIG. 15 shows flow cytometry experiments of anti-1628IGB binding to NmB strain MC58 (FIG. 15, panel A) or to NmA strain Z2491 (FIG. 15, panel B). Controls included no added antiserum or adjuvant only control serum. In both panels, graphs shifted to the right, which corresponded to increased fluorescence of the anti-1628IGB. Hence, antibodies elicited by the vaccine bound strongly to both NmA and NmB strains.

The lower panels in FIG. 15, panels A and B show binding of human IgG to each strain. Levels of binding of human IgG to the bacteria were decreased in the presence of antisera to rfTspB1628IGB, suggesting that the antisera inhibited binding of human IgG to the bacteria.

Figure 16:
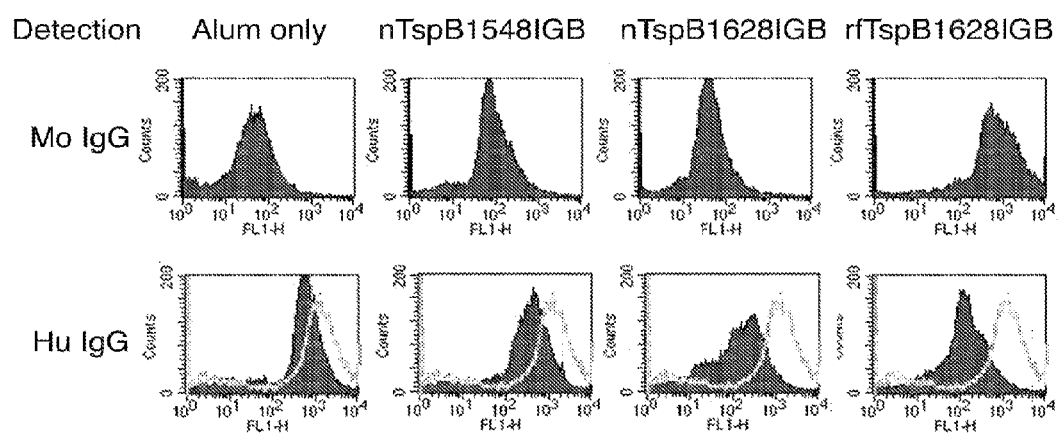
FIG. 16 shows binding experiments similar to FIG. 15 with additional sera from mice immunized with natively-folded TspB1548IGB (nTspB1548IGB), natively-folded TspB1628IGB (nTspB1628IGB), or partially-denatured TspB1628IGB (rfTspB1628IGB).

FIG. 16 shows a similar binding experiment with NmB strain MC58 in which the binding of antibodies elicited by the following immunogens were compared 1) alum adjuvant alone
2) TspB1548IGB
3) TspB1628IGB purified under native conditions
4) TspB1628IGB purified under denaturing conditions and refolded (rfTspBIGB1628).

In each experiment, the cells were grown in CDM+5% Cohn FIV+1% purified human IgG and a 1 to 200 dilution of the indicated antiserum. After the cells reached an OD620 nm of 0.6, they were divided into two equal fractions. One fraction was treated with the anti-mouse IgG-FITC and the other with the anti-human IgG-FITC secondary antibodies to detect binding of the respective IgG. The results show that rfTspB1628IGB elicted IgG antibodies that bind the most strongly to NmB strain MC58. Also, antibodies elicited by the three TspBIGB proteins were able to inhibit human IgG binding with anti-rfTspB1628IGB being the most effective in blocking human IgG binding. TspB, particularly the IGB domain, was found to be the protein expressed by Nm strains that mediates human IgG binding activity. Therefore, antibodies elicited by a TspBIGB-based vaccine can block human IgG binding, which is an important mechanism for survival of Nm strains in human blood.

Example 9

Testing for Protein Deposition in Complement Activation

The ability of antibodies elicited by immunization with TspB IGB vaccine to activate deposition of human complement components on *Neisseria meningitidis* bacteria representative of groups B, C, X, Y, and W135 bacteria can be determined as described below.

The TspB-IGB vaccine used to elicit antibodies may contain TspB-IGB polypeptide combined with any adjuvant (e.g. aluminum hydroxide, aluminum phosphate, MF59, Freund's adjuvant, etc.). Complement activation by the antisera of the vaccine may be determined as described by Welsch et al (Welsch et al, 2003 *J. Infec. Dis.* 188:1730). Briefly, the *Neisseria* cells are grown to an OD$_{620}$ of ~0.6 in CDM/dHuS. The cells are pelleted, washed with Dulbecco's PBS (Invitrogen, Carlsbad, Calif.) containing 1% (weight/volume) BSA (Sigma-Aldrich) (D-BSA), and resuspended in half the volume D-BSA of the original growth media. The bacteria (30 μl) are combined with the pooled antisera from mice immunized with either 2 μg or 10 μg diluted to 1:20 or 1:200 in D-BSA. Human complement from a donor tested for the absence of antibodies to *Neisseria* cells is added to a concentration of 5% (volume/volume) in a total volume of 200 μl. The reaction is allowed to proceed for 30 minutes at ambient temperature with occasional agitation. The cells are pelleted and washed with 200 μl of D-BSA and FITC-conjugated sheep anti-human C3c antibody (BioDesign International, Saco, Me.) is added in D-BSA. After 30 minutes incubation on ice with occasional agitation, the cells are pelleted, resuspended in sterile filtered PBS buffer containing 0.5% (weight/volume) formaldehyde and analyzed by flow cytometery (BD FACSCalibur System, BD Biosciences, San Jose, Calif.).

Deposition of complement components on the cell surface increases the fluorescence of the cells and may be indicated by the shift in fluorescence peak to the right of a graph. The antibody activation may be indicated by the lack of fluorescence of cells alone with active complement or antisera with heat-inactivated complement. The bacteria from flow cytometry are analyzed further by microscopy using a Zeiss Axioplan (Carl Zeiss, Inc.) fluorescence microscope. Activation of complement factor deposition on the cell surface of NmB bacteria is correlated with protection against disease caused by *Neisseria meningitidis* (Welsch et al. 2003 *J. Infec. Dis.* 188:1730).

Example 10

Serum Bactericidal Assays

Complement-Mediated Bactericidal Antibody Activity.

The ability of anti-TspB IGB antiserum to mediate bacteriolysis in the presence of human complement can be measured by the serum bactericidal assay (SBA). The bactericidal assay is performed as previously described (Moe G. R. et al. 2002 *Infect Immun* 70: 6021-31) using mid-log phase bacteria grown overnight on chocolate agar plates then cultured in CDM/dHuS, or for comparison to cells not induced to express TspB IGB, Mueller Hinton media broth supplemented with 0.25% glucose will be used. Cells taken from the chocolate agar plates will be diluted in media to $OD_{620nm}$ of ~0.18 to start the culture then grown to an $OD_{620nm}$ of ~0.62. The bacteria will be pelleted and then washed in Dulbeccos buffered saline with Ca+ and Mg+ (DBS; Mediatech. Manassas Va.), with or without 1% BSA (Equitech). The human complement sources used in each assay are evaluated for intrinsic SBA against test strains in the presence of 60% complement.

The final reaction mixture contains different dilutions of test sera, and 20% (volume/volume) human complement. The buffer is Dulbecco's phosphate buffered saline (Sigma-Aldrich) containing 0.9 mM CaCl2×2 H2O, 0.5 mM MgCl2×6 H2O and 1% (weight/volume) BSA.

The complement source is human serum from a healthy adult with no detectable intrinsic bactericidal activity (Granoff et al. J 1998 *Immunol* 160:5028-36; Welsch et al. 2003 *J. Infec. Dis.* 188:1730). Serum bactericidal titers are defined as the serum dilution resulting in a 50% decrease in CFU per ml after 60 minutes of incubation of bacteria in the reaction mixture, as compared with control CFU per ml at time 0. Typically, bacteria incubated with the negative control antibody and complement show a 150 to 200% increase in CFU/mL during the 60 minutes of incubation.

Example 11

Infant Rat Protection

Passive Protection in Infant Rats.

Anti-TspB-IGB antisera can be tested for passive protection against bacteremia as described below. The results of this experiment can determine the ability of a vaccine based on TspB-IGB to protect against invasive disease in humans.

Infant (4-6 days) Wistar rats are taken from their mothers and randomly divided into groups of 5 rats each. Each pup is given 100 μl of antiserum diluted 1:10 in sterile PBS containing 1% BSA (PBS-BSA) intraperitoneally and then returned to their mothers while the challenge bacteria are prepared. NmB strain M986 or NmC strain 4243 are grown to $O.D._{620}$=~0.6 in CDM-/dHuS, washed, resuspended in PBS-BSA, and diluted to $10^4$ CFU/ml. Each rat pup is then given 100 μl of bacteria, so that the final challenge dose is ~1000 CFU/rat. The pups are then returned to their mothers. The next day, the pups are anesthetized with isoflurane and blood obtained by cardiac puncture using a heparanized needle. The animals are euthanized by $CO_2$ anoxia, and 100 μl, 10 μl, and 1 μl of the blood will be plated on chocolate agar (Remel). After incubating the plates overnight at 37° C., 5% $CO_2$ the colonies will be counted.

Example 12

Passive Protection in an Ex Vivo Human Blood Model of Meningococcal Bacteremia

As an alternative approach to evaluating the ability of antibodies elicited by a vaccine to protect against disease caused by *Neisseria meningitidis* is to determine whether the antisera can lyse or inhibit the growth of *Neisseria meningitidis* group B ex vivo in human blood. Antisera tested are pooled antisera from CD1 mice immunized with TspB-IGB-based vaccines as described above) and the test bacteria (approximately 1000 CFU of a *Neisseria* strain freshly grown in CDM/dHuS media as described above) are combined in freshly obtained human blood from a donor who lacks antibodies to the test strain in sterile glass vials and prepared and tested as described below.

Ex-Vivo Passive Protection Assay (PPA).

Fresh blood from a healthy adult is obtained using a syringe containing recombinant hirudin (lepirudin, 27.8 μg/ml final concentration) as the anti-coagulant. The blood donor may be the same person whose serum was used for complement to measure serum bactericidal activity described above. To each well of the microtiter plate, 65 μl of blood are added, 25 μl of test sera, and 10 μl of PBS buffer containing 15% heated-complement and 1% Bovine Serum Albumin, (Equitech) and approximately 4000 CFU. The positive controls may include a relevant anti-PorA mAb (NIBSC, P1.4 or P1.12) and human serum samples with high, medium or low opsonophagocytic killing activity (Plested and Granoff 2008 *Clin Vaccine Immunol* 15: 799-804) and serum bactericidal activity against the respective test strains. Negative control sera may be heat-inactivated serum from the complement donor or buffer alone. The microtiter plates are incubated for 90 minutes at 37° C. in 5% $CO_2$ with agitation on a MS 3 digital minishaker (IKA, Wilmington, N.C.) at 500 oscillations per minute to completely mix the components. Samples are removed from the wells and quantitative cultures performed on chocolate agar plates, which are incubated at 37° C. in 5% $CO_2$.

The following day CFU/ml is ascertained and the results are calculated as $\log_{10}$ change in CFU/ml at 90 minutes compared to that at time 0 with negative control test sera. Based on reproducibility of replicate assays performed on different days, a positive passive protection activity may be defined as a serum giving ≥0.5 $\log_{10}$ decrease in CFU/ml, as compared to that at time 0 (i.e., about 70% decrease in CFU/ml).

What is claimed is:

1. An isolated polypeptide comprising a contiguous amino acid sequence having at least 90% amino acid sequence identity to SEQ ID NO: 28, wherein the length of said isolated polypeptide is less than the length of full-length mature amino acid sequence of Neisserial T-cell stimulating protein B (TspB).

2. The isolated polypeptide of claim 1, wherein said contiguous amino acid sequence comprises SEQ ID NO: 48.

3. The isolated polypeptide of claim 1, wherein said contiguous amino acid sequence comprises SEQ ID NO: 47.

4. The isolated polypeptide of claim 1, wherein said contiguous amino acid sequence comprises SEQ ID NO: 14 or SEQ ID NO: 17.

5. The isolated polypeptide of claim 1, wherein said isolated polypeptide comprises a variant group peptide ($V^N$) comprising at least 90% amino acid sequence identity to an amino acid sequence set forth in SEQ ID NO: 13, 14, 15, 16, 17, 18, 19, 20, 21, or 22, wherein the variant group peptide is immediately C-terminal to the contiguous amino acid sequence.

6. The isolated polypeptide of claim 1, wherein said polypeptide is conjugated to a carrier protein.

7. The isolated polypeptide of claim 1, wherein said polypeptide is conjugated to an antigen.

8. A nucleic acid encoding a polypeptide according to claim 1.

9. An immunogenic composition comprising:
the isolated polypeptide according to claim 1; and
a pharmaceutically acceptable excipient.

10. The immunogenic composition of claim 9, wherein said composition comprises membrane vesicles.

11. A method of inducing an immune response to *Neisseria meningitidis* in subject, comprising:
administering an immunogenic composition according to claim 9 to a subject in an amount effective to elicit production of antibodies in the subject.

12. The method of claim 11, wherein said subject is human.

13. A method for producing the polypeptide of claim 1, the method comprising:
culturing in a chemically defined medium host cells expressing the polypeptide of claim 1,
wherein said chemically defined media comprises a human blood component, and said culturing is under conditions to provide for production of the polypeptide.

14. The method of claim 13, wherein said human blood component comprises human Cohn Fraction IV.

15. The method of claim 13, wherein said human blood component comprises human serum.

16. The method of claim 13, wherein said host cells are Neisserial bacteria.

17. The isolated polypeptide of claim 1, wherein said isolated polypeptide is at least partially denatured.

18. The isolated polypeptide of claim 1, wherein said contiguous amino acid sequence is selected from one of SEQ ID NOS: 23-34.

19. The isolated polypeptide of claim 1, wherein said polypeptide comprises an amino acid sequence fused to the N-terminus of the polypeptide, wherein the amino acid sequence is heterologous to the contiguous amino acid sequence.

20. The isolated polypeptide of claim 1, wherein said polypeptide comprises an amino acid sequence fused to the C-terminus of the polypeptide, wherein the amino acid sequence is heterologous to the contiguous amino acid sequence.

21. The isolated polypeptide of claim 1, wherein said contiguous amino acid sequence has 95% amino acid sequence identity to SEQ ID NO: 28.

22. The isolated polypeptide of claim 1, wherein said contiguous amino acid sequence has 95% amino acid sequence identity to SEQ ID NO: 30.

23. The isolated polypeptide of claim 1, wherein said contiguous amino acid sequence is SEQ ID NO: 28.

24. The isolated polypeptide of claim 1, wherein said contiguous amino acid sequence is SEQ ID NO: 30.

25. The isolated polypeptide of claim 1, wherein said polypeptide is up to 150 amino acids in length.

26. The isolated polypeptide of claim 1, wherein said polypeptide is up to 200 amino acids in length.

27. The isolated polypeptide of claim 1, wherein said polypeptide is up to 300 amino acids in length.

28. The isolated polypeptide of claim 1, wherein said polypeptide is up to 400 amino acids in length.

29. The immunogenic composition of claim 10, wherein the membrane vesicles are produced from a Neisserial bacteria.

* * * * *

SEQUENCE LISTING

```
<160> NUMBER OF SEQ ID NOS: 70

<210> SEQ ID NO 1
<211> LENGTH: 543
<212> TYPE: PRT
<213> ORGANISM: Neisseria meningitidis
```

```
<400> SEQUENCE: 1

Met Phe Leu Ile Leu Gly Arg Asn Phe Leu Lys Ile Leu Cys Phe
  1               5                  10                  15

Ser Phe Phe Val Ser Lys Phe Ala Leu Ala Ser Val Asn Val Pro Gly
             20                  25                  30

Lys Phe Asp Arg Val Glu Val Tyr Asp Asp Gly Arg Tyr Leu Gly Ile
             35                  40                  45

Arg Gly Ser Asp Asp Lys Arg Arg Val Trp Glu Gly Val Phe Asp
         50                  55                  60

Lys Glu Ser Gly Arg Tyr Leu Asn Ser Glu Ala Gln Asp Leu Thr Val
 65                  70                  75                  80

Arg His Val Ser Thr Gly Ala Ser Ser Thr Gly Lys Val Ser Ala Val
                 85                  90                  95

Val Ser Ser Ser Val Ser Arg Ala Gly Val Leu Ala Gly Val Gly Lys
                100                 105                 110

Leu Ala Arg Leu Gly Ala Lys Phe Ser Thr Arg Ala Val Pro Tyr Val
            115                 120                 125

Gly Thr Ala Leu Leu Ala His Asp Val Tyr Glu Thr Phe Lys Glu Asp
130                 135                 140

Ile Gln Ala Gln Gly Tyr Gln Tyr Asp Pro Glu Thr Asp Lys Phe Val
145                 150                 155                 160

Lys Gly Tyr Glu Tyr Ser Asn Cys Leu Trp Tyr Glu Asp Glu Arg Arg
                165                 170                 175

Ile Asn Arg Thr Tyr Gly Cys Tyr Gly Val Asp Ser Ser Ile Met Arg
            180                 185                 190

Leu Met Ser Asp Tyr Ser Arg Phe Pro Glu Val Lys Glu Leu Met Glu
            195                 200                 205

Ser Gln Met Tyr Arg Leu Ala Arg Pro Phe Trp Asn Trp His Lys Glu
            210                 215                 220

Glu Leu Asn Lys Leu Ser Ser Leu Asp Trp Asn Asn Phe Val Leu Asn
225                 230                 235                 240

Arg Cys Thr Phe Asp Trp Asn Gly Gly Asp Cys Val Val Asn Lys Gly
                245                 250                 255

Asp Asp Tyr Arg Asn Gly Ala Asn Phe Ser Leu Ser Arg Asn Pro Lys
            260                 265                 270

Tyr Lys Glu Glu Met Asp Ala Lys Lys Leu Glu Glu Ile Leu Ser Leu
            275                 280                 285

Lys Val Asp Ala Asn Pro Asp Lys Tyr Ile Lys Ala Thr Gly Tyr Pro
            290                 295                 300

Gly Tyr Ser Glu Lys Val Glu Val Ala Pro Gly Thr Lys Val Asn Met
305                 310                 315                 320

Gly Pro Val Thr Asp Arg Asn Gly Asn Pro Val Gln Val Val Ala Thr
                325                 330                 335

Phe Gly Arg Asp Ser Gln Gly Asn Thr Thr Val Asp Val Gln Val Ile
            340                 345                 350

Pro Arg Pro Asp Leu Thr Pro Gly Ser Ala Glu Ala Pro Asn Ala Gln
            355                 360                 365

Pro Leu Pro Glu Val Ser Pro Ala Glu Asn Pro Ala Asn Asn Pro Ala
            370                 375                 380

Pro Asn Glu Asn Pro Gly Thr Arg Pro Asn Glu Pro Asp Pro Asp
385                 390                 395                 400

Leu Asn Pro Asp Ala Asn Pro Asp Thr Asp Gly Gln Pro Gly Thr Arg
                405                 410                 415
```

```
Pro Asp Ser Pro Ala Val Pro Asp Arg Pro Asn Gly Arg His Arg Lys
        420                 425                 430

Glu Arg Lys Glu Gly Glu Asp Gly Gly Leu Leu Cys Lys Phe Phe Pro
        435                 440                 445

Asp Ile Leu Ala Cys Asp Arg Leu Pro Glu Pro Asn Pro Ala Glu Asp
450                 455                 460

Leu Asn Leu Pro Ser Glu Thr Val Asn Val Glu Phe Gln Lys Ser Gly
465                 470                 475                 480

Ile Phe Gln Asp Ser Ala Gln Cys Pro Ala Pro Val Thr Phe Thr Val
                485                 490                 495

Thr Val Leu Asp Ser Ser Arg Gln Phe Ala Phe Ser Phe Glu Asn Ala
            500                 505                 510

Cys Thr Ile Ala Glu Arg Leu Arg Tyr Met Leu Leu Ala Leu Ala Trp
        515                 520                 525

Ala Val Ala Ala Phe Phe Cys Ile Arg Thr Val Ser Arg Glu Val
        530                 535                 540

<210> SEQ ID NO 2
<211> LENGTH: 519
<212> TYPE: PRT
<213> ORGANISM: Neisseria meningitidis

<400> SEQUENCE: 2

Met Ala Ser Val Asn Val Pro Gly Lys Phe Asp Arg Val Glu Val Tyr
1               5                   10                  15

Asp Asp Gly Arg Tyr Leu Gly Ile Arg Gly Ser Asp Asp Lys Arg Arg
            20                  25                  30

Arg Val Trp Glu Gly Val Phe Asp Lys Glu Ser Gly Arg Tyr Leu Asn
        35                  40                  45

Ser Glu Ala Gln Asp Leu Thr Val Arg His Val Ser Thr Gly Ala Ser
    50                  55                  60

Ser Thr Gly Lys Val Ser Ala Val Val Ser Ser Ser Val Ser Arg Ala
65                  70                  75                  80

Gly Val Leu Ala Gly Val Gly Lys Leu Ala Arg Leu Gly Ala Lys Phe
                85                  90                  95

Ser Thr Arg Ala Val Pro Tyr Val Gly Thr Ala Leu Leu Ala His Asp
            100                 105                 110

Val Tyr Glu Thr Phe Lys Glu Asp Ile Gln Ala Gln Gly Tyr Gln Tyr
        115                 120                 125

Asp Pro Glu Thr Asp Lys Phe Val Lys Gly Tyr Glu Tyr Ser Asn Cys
    130                 135                 140

Leu Trp Tyr Glu Asp Glu Arg Arg Ile Asn Arg Thr Tyr Gly Cys Tyr
145                 150                 155                 160

Gly Val Asp Ser Ser Ile Met Arg Leu Met Ser Asp Tyr Ser Arg Phe
                165                 170                 175

Pro Glu Val Lys Glu Leu Met Glu Ser Gln Met Tyr Arg Leu Ala Arg
            180                 185                 190

Pro Phe Trp Asn Trp His Lys Glu Glu Leu Asn Lys Leu Ser Ser Leu
        195                 200                 205

Asp Trp Asn Asn Phe Val Leu Asn Arg Cys Thr Phe Asp Trp Asn Gly
    210                 215                 220

Gly Asp Cys Val Val Asn Lys Gly Asp Asp Tyr Arg Asn Gly Ala Asn
225                 230                 235                 240

Phe Ser Leu Ser Arg Asn Pro Lys Tyr Lys Glu Glu Met Asp Ala Lys
                245                 250                 255
```

```
Lys Leu Glu Glu Ile Leu Ser Leu Lys Val Asp Ala Asn Pro Asp Lys
            260                 265                 270

Tyr Ile Lys Ala Thr Gly Tyr Pro Gly Tyr Ser Glu Lys Val Glu Val
        275                 280                 285

Ala Pro Gly Thr Lys Val Asn Met Gly Pro Val Thr Asp Arg Asn Gly
    290                 295                 300

Asn Pro Val Gln Val Ala Thr Phe Gly Arg Asp Ser Gln Gly Asn
305                 310                 315                 320

Thr Thr Val Asp Val Gln Val Ile Pro Arg Pro Asp Leu Thr Pro Gly
                325                 330                 335

Ser Ala Glu Ala Pro Asn Ala Gln Pro Leu Pro Glu Val Ser Pro Ala
            340                 345                 350

Glu Asn Pro Ala Asn Pro Ala Pro Asn Glu Asn Pro Gly Thr Arg
        355                 360                 365

Pro Asn Pro Glu Pro Asp Pro Asp Leu Asn Pro Asp Ala Asn Pro Asp
    370                 375                 380

Thr Asp Gly Gln Pro Gly Thr Arg Pro Asp Ser Pro Ala Val Pro Asp
385                 390                 395                 400

Arg Pro Asn Gly Arg His Arg Lys Glu Arg Lys Glu Gly Glu Asp Gly
                405                 410                 415

Gly Leu Leu Cys Lys Phe Phe Pro Asp Ile Leu Ala Cys Asp Arg Leu
            420                 425                 430

Pro Glu Pro Asn Pro Ala Glu Asp Leu Asn Leu Pro Ser Glu Thr Val
        435                 440                 445

Asn Val Glu Phe Gln Lys Ser Gly Ile Phe Gln Asp Ser Ala Gln Cys
    450                 455                 460

Pro Ala Pro Val Thr Phe Thr Val Thr Val Leu Asp Ser Ser Arg Gln
465                 470                 475                 480

Phe Ala Phe Ser Phe Glu Asn Ala Cys Thr Ile Ala Glu Arg Leu Arg
                485                 490                 495

Tyr Met Leu Leu Ala Leu Ala Trp Ala Val Ala Ala Phe Phe Cys Ile
            500                 505                 510

Arg Thr Val Ser Arg Glu Val
        515

<210> SEQ ID NO 3
<211> LENGTH: 548
<212> TYPE: PRT
<213> ORGANISM: Neisseria meningitidis

<400> SEQUENCE: 3

Met Lys Gln Asn Val Met Phe Ile Ile Leu Gly Arg Asn Phe Leu Lys
1               5                   10                  15

Ile Ile Leu Cys Phe Ser Phe Phe Val Ser Lys Phe Ala Leu Ala Ser
            20                  25                  30

Val Asn Ala Pro Gly Lys Phe Asp Arg Val Glu Val Tyr Asp Asp Gly
        35                  40                  45

Arg Tyr Leu Gly Ile Arg Gly Ser Asp Lys Arg Arg Ile Trp
    50                  55                  60

Lys Gly Val Phe Asp Arg Glu Ser Gly Arg Tyr Leu Thr Ser Glu Ala
65                  70                  75                  80

Gln Asp Leu Lys Val Arg His Val Ser Thr Gly Ala Ser Ser Thr Gly
                85                  90                  95

Lys Val Ser Ser Val Val Ser Ser Ser Val Ser Arg Ala Gly Val Leu
            100                 105                 110
```

```
Ala Gly Val Gly Lys Leu Ala Arg Leu Gly Ala Lys Leu Ser Thr Arg
            115                 120                 125

Ala Val Pro Tyr Val Gly Thr Ala Leu Leu Ala His Asp Val Tyr Glu
        130                 135                 140

Thr Phe Lys Glu Asp Ile Gln Ala Gln Gly Tyr Gln Tyr Asp Pro Glu
145                 150                 155                 160

Thr Asp Lys Phe Val Lys Gly Tyr Glu Tyr Ser Asn Cys Leu Trp Tyr
                165                 170                 175

Glu Asp Lys Arg Arg Ile Asn Arg Thr Tyr Gly Cys Tyr Gly Val Asp
            180                 185                 190

Ser Ser Ile Met Arg Leu Met Ser Asp Ser Arg Phe Pro Glu Val
        195                 200                 205

Lys Glu Leu Met Glu Ser Gln Met Tyr Arg Leu Ala Arg Pro Phe Trp
        210                 215                 220

Asn Trp His Lys Glu Glu Leu Asn Lys Leu Ser Ser Leu Asp Trp Asn
225                 230                 235                 240

Asn Phe Val Leu Asn Ser Cys Thr Phe Asp Trp Asn Gly Gly Asp Cys
                245                 250                 255

Val Val Asn Lys Gly Asp Phe Arg Asn Gly Ala Asp Phe Ser Leu
            260                 265                 270

Ile Arg Asn Ser Lys Tyr Lys Glu Glu Met Asp Ala Lys Lys Leu Glu
        275                 280                 285

Glu Ile Leu Ser Leu Lys Val Asp Ala Asn Pro Asp Lys Tyr Ile Lys
290                 295                 300

Ala Thr Gly Tyr Pro Gly Tyr Ser Glu Lys Val Glu Val Ala Pro Gly
305                 310                 315                 320

Thr Lys Val Asn Met Gly Pro Val Thr Asp Arg Asn Gly Asn Pro Val
                325                 330                 335

Gln Val Val Ala Thr Phe Gly Arg Asp Ser Gln Gly Asn Thr Thr Val
            340                 345                 350

Asp Val Gln Val Ile Pro Arg Pro Asp Leu Thr Pro Gly Ser Ala Glu
        355                 360                 365

Ala Pro Asn Ala Gln Pro Leu Pro Glu Val Ser Pro Ala Glu Asn Pro
        370                 375                 380

Ala Asn Asn Pro Asn Pro Asn Glu Asn Pro Gly Thr Ser Pro Asn Pro
385                 390                 395                 400

Glu Pro Asp Pro Asp Leu Asn Pro Asp Ala Asn Pro Asp Thr Asp Gly
                405                 410                 415

Gln Pro Gly Thr Arg Pro Asp Ser Pro Ala Val Pro Gly Arg Thr Asn
            420                 425                 430

Gly Arg Asp Gly Lys Asp Gly Lys Asp Gly Lys Asp Gly Gly Leu Leu
        435                 440                 445

Cys Lys Phe Phe Pro Asp Ile Leu Ala Cys Asp Arg Leu Pro Glu Ser
        450                 455                 460

Asn Pro Ala Glu Asp Leu Asn Leu Pro Ser Glu Thr Val Asn Val Glu
465                 470                 475                 480

Phe Gln Lys Ser Gly Ile Phe Gln Asp Ser Ala Gln Cys Pro Ala Pro
                485                 490                 495

Val Thr Phe Thr Val Thr Val Leu Asp Ser Ser Arg Gln Phe Ala Phe
            500                 505                 510

Ser Phe Glu Asn Ala Cys Thr Ile Ala Glu Arg Leu Arg Tyr Met Leu
        515                 520                 525

Leu Ala Leu Ala Trp Ala Val Ala Ala Phe Phe Cys Ile Arg Thr Val
```

```
                530                 535                 540
Ser Arg Glu Val
545

<210> SEQ ID NO 4
<211> LENGTH: 538
<212> TYPE: PRT
<213> ORGANISM: Neisseria meningitidis

<400> SEQUENCE: 4

Met Lys Gln Asn Val Met Phe Leu Ile Leu Gly Arg Asn Phe Leu Lys
  1               5                  10                  15

Ile Ile Leu Cys Phe Ser Phe Val Pro Lys Phe Ala Leu Ala Ser
             20                  25                  30

Val Asn Val Pro Gly Lys Phe Asp Arg Val Glu Val Tyr Asp Asp Gly
             35                  40                  45

Arg Tyr Leu Gly Ile Arg Gly Ser Asp Lys Arg Arg Ile Trp
 50                  55                  60

Lys Gly Val Phe Asp Arg Glu Ser Gly Arg Tyr Leu Thr Ser Glu Ala
 65                  70                  75                  80

Gln Asp Leu Lys Val Arg His Val Ser Thr Gly Ala Ser Ser Thr Gly
                 85                  90                  95

Lys Val Ser Ser Val Val Ser Ser Val Ser Arg Ala Gly Val Leu
                100                 105                 110

Ala Gly Val Gly Lys Leu Ala Arg Leu Gly Ala Lys Phe Ser Thr Arg
            115                 120                 125

Ala Val Pro Tyr Val Gly Thr Ala Leu Leu Ala His Asp Val Tyr Glu
            130                 135                 140

Thr Phe Lys Glu Asp Ile Gln Ala Gln Gly Tyr Gln Tyr Asp Pro Glu
145                 150                 155                 160

Thr Asp Lys Phe Val Lys Gly Tyr Glu Tyr Ser Asn Cys Leu Trp Tyr
                165                 170                 175

Glu Asp Glu Arg Arg Ile Asn Arg Thr Tyr Gly Cys Tyr Gly Val Asp
            180                 185                 190

Ser Ser Ile Met Arg Leu Met Ser Asp Tyr Ser Arg Phe Pro Glu Val
            195                 200                 205

Lys Glu Leu Met Glu Ser Gln Met Glu Arg Leu Ala Arg Pro Tyr Trp
    210                 215                 220

Glu Lys Leu Arg Asn Arg Pro Asp Met Tyr Tyr Phe Lys Asn Tyr Asn
225                 230                 235                 240

Phe Lys Arg Cys Tyr Phe Gly Leu Asn Gly Gly Asp Cys Leu Val Ala
                245                 250                 255

Lys Gly Asp Asp Gly Arg Thr Phe Ile Ser Phe Ser Leu Gln Gly Asn
            260                 265                 270

Ser Lys Tyr Lys Glu Glu Met Asp Ala Lys Lys Glu Glu Ile Leu Ser
            275                 280                 285

Leu Lys Val Asp Ala Asn Pro Asp Lys Tyr Ile Lys Ala Thr Gly Tyr
    290                 295                 300

Pro Gly Tyr Ser Glu Lys Val Glu Val Ala Pro Gly Thr Lys Val Asn
305                 310                 315                 320

Met Gly Pro Val Thr Asp Arg Asn Gly Asn Pro Val Gln Val Val Ala
                325                 330                 335

Thr Phe Gly Arg Asp Ser Gln Gly Asn Thr Thr Val Asp Val Gln Val
            340                 345                 350

Ile Pro Arg Pro Asp Leu Thr Pro Gly Ser Ala Glu Ala Pro Asn Ala
```

```
                    355                 360                 365
Gln Pro Leu Pro Glu Val Ser Pro Ala Glu Asn Pro Ala Asn Pro
        370                 375                 380

Ala Pro Asn Glu Asn Pro Gly Thr Arg Pro Asn Pro Glu Pro Asp Pro
385                 390                 395                 400

Asp Leu Asn Pro Asp Ala Asn Pro Asp Thr Asp Gly Gln Pro Gly Thr
                405                 410                 415

Ser Pro Asp Ser Pro Ala Val Pro Asp Arg Pro Asn Gly Arg Asp Gly
            420                 425                 430

Lys Asp Gly Gly Leu Leu Cys Lys Phe Phe Pro Asp Ile Leu Ala Cys
435                 440                 445

Asp Arg Leu Pro Glu Pro Asn Pro Ala Glu Asp Leu Asn Leu Pro Ser
        450                 455                 460

Glu Thr Val Asn Val Glu Phe Lys Lys Ser Gly Ile Phe Gln Asp Ser
465                 470                 475                 480

Ala Gln Cys Pro Ala Pro Val Thr Phe Thr Ile Thr Val Leu Asp Ser
                485                 490                 495

Ser Lys Gln Phe Ala Phe Ser Phe Glu Asn Ala Cys Thr Ile Ala Glu
            500                 505                 510

Arg Leu Arg Tyr Met Leu Leu Ala Leu Ala Trp Ala Val Ala Ala Phe
        515                 520                 525

Phe Cys Ile Arg Thr Val Ser Arg Glu Val
        530                 535

<210> SEQ ID NO 5
<211> LENGTH: 501
<212> TYPE: PRT
<213> ORGANISM: Neisseria meningitidis

<400> SEQUENCE: 5

Met Tyr Ala Leu Ser Glu Lys Tyr Asn Asp Asn Gly Phe Lys Ala Tyr
1               5                   10                  15

Lys Val Leu Gly Glu Gly Gly Ile Tyr Thr Glu Tyr Asn Tyr Lys
            20                  25                  30

Phe Asp Lys Ser Leu Asn Leu Asn Val Leu Glu Ser Ser Thr Gly Ala
        35                  40                  45

Arg Ser Leu Glu Lys Val Pro Val Lys Phe Thr Ala Ser Val Ser Arg
    50                  55                  60

Ala Gly Val Leu Ala Gly Val Gly Lys Leu Ala Arg Leu Gly Ala Lys
65                  70                  75                  80

Phe Ser Thr Arg Ala Val Pro Tyr Val Gly Thr Ala Leu Leu Ala His
                85                  90                  95

Asp Val Tyr Glu Thr Phe Lys Glu Asp Ile Gln Ala Arg Gly Tyr Gln
            100                 105                 110

Tyr Asp Pro Glu Thr Asp Lys Phe Val Lys Gly Tyr Glu Tyr Ser Asn
        115                 120                 125

Cys Leu Trp Tyr Glu Asp Glu Arg Arg Ile Asn Arg Thr Tyr Gly Cys
    130                 135                 140

Tyr Gly Val Asp Ser Ser Ile Met Arg Leu Met Ser Asp Tyr Ser Arg
145                 150                 155                 160

Phe Pro Glu Val Lys Glu Leu Met Glu Ser Gln Met Glu Arg Leu Ala
                165                 170                 175

Arg Pro Tyr Trp Glu Lys Leu Arg Asn Arg Pro Asp Met Tyr Tyr Phe
            180                 185                 190

Lys Asn Tyr Asn Phe Lys Arg Cys Tyr Phe Gly Leu Asn Gly Gly Asp
```

```
                195                 200                 205
Cys Leu Val Ala Lys Gly Asp Asp Gly Arg Thr Phe Ile Ser Phe Ser
210                 215                 220

Leu Gln Gly Asn Ser Lys Tyr Lys Glu Glu Met Asp Ala Lys Lys Leu
225                 230                 235                 240

Glu Glu Ile Leu Ser Leu Lys Val Asp Ala Asn Pro Asp Lys Tyr Ile
            245                 250                 255

Lys Ala Thr Gly Tyr Pro Gly Tyr Ser Glu Lys Val Glu Val Ala Pro
            260                 265                 270

Gly Thr Lys Val Asn Met Gly Pro Val Thr Asp Arg Asn Gly Asn Pro
        275                 280                 285

Val Gln Val Val Ala Thr Phe Gly Arg Asp Ser Gln Gly Asn Thr Thr
290                 295                 300

Val Asp Val Gln Val Ile Pro Arg Pro Asp Leu Thr Pro Gly Ser Ala
305                 310                 315                 320

Glu Ala Pro Asn Ala Gln Pro Leu Pro Glu Val Ser Pro Ala Glu Asn
            325                 330                 335

Pro Ala Asn Asn Pro Ala Pro Asn Glu Asn Pro Gly Thr Arg Pro Asn
        340                 345                 350

Pro Glu Pro Asp Pro Asp Leu Asn Pro Asp Ala Asn Pro Asp Thr Asp
            355                 360                 365

Gly Gln Pro Gly Thr Arg Pro Asp Ser Pro Ala Val Pro Asp Arg Pro
370                 375                 380

Asn Gly Arg His Arg Lys Glu Arg Lys Glu Gly Glu Asp Gly Gly Leu
385                 390                 395                 400

Leu Cys Lys Phe Phe Pro Asp Ile Leu Ala Cys Asp Arg Leu Pro Glu
            405                 410                 415

Pro Asn Pro Ala Glu Asp Leu Asn Leu Pro Ser Glu Thr Val Asn Val
        420                 425                 430

Glu Phe Gln Lys Ser Gly Ile Phe Gln Asp Ser Ala Gln Cys Pro Ala
            435                 440                 445

Pro Val Thr Phe Thr Val Thr Val Leu Asp Ser Ser Arg Gln Phe Ala
450                 455                 460

Phe Ser Phe Glu Asn Ala Cys Thr Ile Ala Glu Arg Leu Arg Tyr Met
465                 470                 475                 480

Leu Leu Ala Leu Ala Trp Ala Val Ala Ala Phe Phe Cys Ile Arg Thr
            485                 490                 495

Val Ser Arg Glu Val
            500

<210> SEQ ID NO 6
<211> LENGTH: 479
<212> TYPE: PRT
<213> ORGANISM: Neisseria meningitidis

<400> SEQUENCE: 6

Met Ser Leu Ile Phe Leu Leu Gly Ser Gln Lys Lys Met Glu Lys Phe
1               5                   10                  15

Arg Met Asn Leu Phe Thr Arg Asn Phe Leu Ile Ala Thr Pro Ile Leu
            20                  25                  30

Met Cys Cys Ser Leu Ser Phe Ala Glu Pro Ala Arg Ile Asp Asp Arg
        35                  40                  45

Ile Ile Lys Phe Arg Pro Ser Lys Ser Lys Phe Phe Glu Ser Thr Gly
    50                  55                  60

Tyr Arg Lys Ile Asn Asn Glu Phe Ser Lys Phe Thr Glu Ala Ala Asn
```

```
            65                  70                  75                  80
Val Glu His Ile Pro Thr Gly Ala Lys Ala Arg Ile Asn Ala Lys Ile
                        85                  90                  95

Thr Ala Ser Val Ser Arg Ala Ala Val Leu Ser Gly Val Gly Lys Leu
                100                 105                 110

Val Arg Arg Ile Asn Arg Thr Tyr Gly Cys Tyr Gly Val Asp Ser Ser
            115                 120                 125

Ile Met Arg Leu Met Ser Asp Tyr Ser Arg Phe Pro Glu Val Lys Glu
        130                 135                 140

Leu Met Glu Ser Gln Met Glu Arg Leu Ala Arg Pro Tyr Trp Glu Lys
145                 150                 155                 160

Leu Arg Asn Arg Pro Asp Met Tyr Tyr Phe Lys Asn Tyr Asn Phe Lys
                165                 170                 175

Arg Cys Tyr Phe Gly Leu Asn Gly Gly Asp Cys Leu Val Ala Lys Gly
            180                 185                 190

Asp Asp Gly Arg Thr Phe Ile Ser Phe Ser Leu Gln Gly Asn Ser Lys
        195                 200                 205

Tyr Lys Glu Glu Met Asp Ala Lys Lys Leu Glu Glu Ile Leu Ser Leu
    210                 215                 220

Lys Val Asp Ala Asn Pro Asp Lys Tyr Ile Lys Ala Thr Gly Tyr Pro
225                 230                 235                 240

Gly Tyr Ser Glu Lys Val Glu Val Ala Pro Gly Thr Lys Val Asn Met
                245                 250                 255

Gly Pro Val Thr Asp Arg Asn Gly Asn Pro Val Gln Val Ala Thr
            260                 265                 270

Phe Gly Arg Asp Ser Gln Gly Asn Thr Thr Val Asp Val Gln Val Ile
        275                 280                 285

Pro Arg Pro Asp Leu Thr Pro Gly Ser Ala Glu Ala Pro Asn Ala Gln
    290                 295                 300

Pro Leu Pro Glu Val Ser Pro Ala Glu Asn Pro Ala Asn Asn Pro Ala
305                 310                 315                 320

Pro Asn Glu Asn Pro Gly Thr Arg Pro Asn Pro Glu Pro Asp Pro Asp
                325                 330                 335

Leu Asn Pro Asp Ala Asn Pro Asp Thr Asp Gly Gln Pro Gly Thr Arg
            340                 345                 350

Pro Asp Ser Pro Ala Val Pro Asp Arg Pro Asn Gly His Arg Lys
        355                 360                 365

Glu Arg Lys Glu Gly Gly Asp Gly Gly Leu Leu Cys Lys Phe Phe Pro
    370                 375                 380

Asp Ile Leu Ala Cys Asp Arg Leu Pro Glu Pro Asn Pro Ala Glu Asp
385                 390                 395                 400

Leu Asn Leu Pro Ser Glu Thr Val Asn Val Glu Phe Gln Lys Ser Gly
                405                 410                 415

Ile Phe Gln Asp Ser Ala Gln Cys Pro Ala Pro Val Thr Phe Thr Val
            420                 425                 430

Thr Val Leu Asp Ser Ser Arg Gln Phe Ala Phe Ser Phe Glu Asn Ala
        435                 440                 445

Cys Thr Ile Ala Glu Arg Leu Arg Tyr Met Leu Leu Ala Leu Ala Trp
    450                 455                 460

Ala Val Ala Ala Phe Phe Cys Ile Arg Thr Val Ser Arg Glu Val
465                 470                 475

<210> SEQ ID NO 7
<211> LENGTH: 517
```

<212> TYPE: PRT
<213> ORGANISM: Neisseria meningitidis

<400> SEQUENCE: 7

```
Met Leu Gly Met Phe Ser Val Asn Ser Tyr Ala Glu Arg Phe Lys Tyr
  1               5                  10                  15

Pro Ile Gly Asn Ser Asp Val Arg Leu Asp Ile Asp His Lys Lys Ser
             20                  25                  30

Val Val Thr Asp Phe Arg Val Asp Gly Gln Arg Phe Ser Gly Arg Ile
         35                  40                  45

Ile Glu Pro Ser Ile Ile Glu His Val Pro Thr Gly Ala Arg Ser Leu
     50                  55                  60

Glu Lys Val Pro Val Lys Phe Thr Ala Ser Val Ser Arg Ala Ala Val
 65                  70                  75                  80

Leu Ser Gly Val Gly Lys Leu Ala Arg Leu Gly Ala Lys Leu Ser Thr
                 85                  90                  95

Arg Ala Val Pro Tyr Val Gly Thr Ala Leu Leu Ala His Asp Val Tyr
                100                 105                 110

Glu Thr Phe Lys Glu Asp Ile Gln Ala Gln Gly Tyr Gln Tyr Asp Pro
            115                 120                 125

Glu Thr Asp Lys Phe Val Lys Gly Tyr Glu Tyr Ser Asn Cys Leu Trp
        130                 135                 140

Tyr Glu Asp Lys Arg Arg Ile Asn Arg Thr Tyr Gly Cys Tyr Gly Val
145                 150                 155                 160

Asp Ser Ser Ile Met Arg Leu Met Ser Asp Ser Arg Phe Pro Glu
                165                 170                 175

Val Lys Glu Leu Met Glu Ser Gln Met Tyr Arg Leu Ala Arg Pro Phe
                180                 185                 190

Trp Asn Trp His Lys Glu Glu Leu Asn Lys Leu Ser Ser Leu Asp Trp
            195                 200                 205

Asn Asn Phe Val Leu Asn Arg Cys Thr Phe Asn Trp Asn Gly Gly Asp
        210                 215                 220

Cys Leu Val Asn Lys Gly Asp Asp Phe Arg Asn Gly Ala Asp Phe Ser
225                 230                 235                 240

Leu Ile Arg Asn Ser Lys Tyr Lys Glu Glu Met Asp Ala Lys Lys Leu
                245                 250                 255

Glu Glu Ile Leu Ser Leu Lys Val Asp Ala Asn Pro Asp Lys Tyr Ile
            260                 265                 270

Lys Ala Thr Gly Tyr Pro Gly Tyr Ser Glu Lys Val Glu Val Ala Pro
        275                 280                 285

Gly Thr Lys Val Asn Met Gly Pro Val Thr Asp Arg Asn Gly Asn Pro
    290                 295                 300

Val Gln Val Val Ala Thr Phe Gly Arg Asp Ser Gln Gly Asn Thr Thr
305                 310                 315                 320

Val Asp Val Gln Val Ile Pro Arg Pro Asp Leu Thr Pro Gly Ser Ala
                325                 330                 335

Glu Ala Pro Asn Ala Gln Pro Leu Pro Glu Val Ser Pro Ala Glu Asn
            340                 345                 350

Pro Ala Asn Asn Pro Asn Pro Asn Glu Asn Pro Gly Thr Ser Pro Asn
        355                 360                 365

Pro Glu Pro Asp Pro Asp Leu Asn Pro Asp Ala Asn Pro Asp Thr Asp
    370                 375                 380

Gly Gln Pro Gly Thr Arg Pro Asp Ser Pro Ala Val Pro Gly Arg Thr
385                 390                 395                 400
```

-continued

```
Asn Gly Arg Asp Gly Lys Asp Gly Lys Asp Gly Gly Leu
                405             410             415

Leu Cys Lys Phe Phe Pro Asp Ile Leu Ala Cys Asp Arg Leu Pro Glu
            420             425             430

Ser Asn Pro Ala Glu Asp Leu Asn Leu Pro Ser Glu Thr Val Asn Val
            435             440             445

Glu Phe Gln Lys Ser Gly Ile Phe Gln Asp Ser Ala Gln Cys Pro Ala
            450             455             460

Pro Val Thr Phe Thr Val Thr Val Leu Asp Ser Ser Arg Gln Phe Ala
465             470             475             480

Phe Ser Phe Glu Asn Ala Cys Thr Ile Ala Glu Arg Leu Arg Tyr Met
            485             490             495

Leu Leu Ala Leu Ala Trp Ala Val Ala Ala Phe Phe Cys Ile Arg Thr
            500             505             510

Val Ser Arg Glu Val
            515

<210> SEQ ID NO 8
<211> LENGTH: 509
<212> TYPE: PRT
<213> ORGANISM: Neisseria gonorrheae

<400> SEQUENCE: 8

Met Met Tyr Ser Phe Glu Ala Asn Ala Asn Ala Val Lys Ile Ser Glu
1               5                   10                  15

Thr Leu Ser Val Asp Thr Gly Gln Gly Ala Lys Val His Lys Phe Val
                20                  25                  30

Pro Lys Ser Ser Asn Ile Tyr Ser Ser Asp Leu Thr Lys Ala Val Asp
            35                  40                  45

Leu Thr His Ile Pro Thr Gly Ala Lys Ala Arg Ile Asn Ala Lys Ile
        50                  55                  60

Thr Ala Ser Val Ser Arg Ala Gly Val Leu Ser Gly Val Gly Lys Leu
65                  70                  75                  80

Val Arg Gln Gly Ala Lys Phe Gly Thr Arg Ala Val Pro Tyr Val Gly
                85                  90                  95

Thr Ala Leu Leu Ala His Asp Val Tyr Glu Thr Phe Lys Glu Asp Ile
            100                 105                 110

Gln Ala Arg Gly Cys Arg Tyr Asp Pro Glu Thr Asp Lys Phe Val Lys
        115                 120                 125

Gly Tyr Glu Tyr Ala Asn Cys Leu Trp Tyr Asp Glu Arg Arg Ile
130                 135                 140

Asn Arg Thr Tyr Gly Cys Tyr Gly Val Asp Ser Ser Ile Met Arg Leu
145                 150                 155                 160

Met Pro Asp Arg Ser Arg Phe Pro Glu Val Lys Gln Leu Met Glu Ser
                165                 170                 175

Gln Met Tyr Arg Leu Ala Arg Pro Phe Trp Asn Trp Arg Lys Glu Glu
            180                 185                 190

Leu Asn Lys Leu Ser Ser Leu Asp Trp Asn Asn Phe Val Leu Asn Arg
        195                 200                 205

Cys Thr Phe Asp Trp Asn Gly Gly Cys Ala Val Asn Lys Gly Asp
    210                 215                 220

Asp Phe Arg Ala Gly Ala Ser Phe Ser Leu Gly Arg Asn Pro Lys Tyr
225                 230                 235                 240

Lys Glu Glu Met Asp Ala Lys Lys Pro Glu Glu Ile Leu Ser Leu Lys
                245                 250                 255
```

Val Asp Ala Asp Pro Asp Tyr Pro Lys Tyr Ile Glu Ala Thr Gly Tyr
                260                 265                 270

Pro Gly Tyr Ser Glu Lys Val Glu Val Ala Pro Gly Thr Lys Val Asn
            275                 280                 285

Met Gly Pro Val Thr Asp Arg Asn Gly Asn Pro Val Gln Val Ala Ala
290                 295                 300

Thr Phe Gly Arg Asp Ala Gln Gly Asn Thr Thr Ala Asp Val Gln Val
305                 310                 315                 320

Ile Pro Arg Pro Asp Leu Thr Pro Ala Ser Ala Glu Ala Pro His Ala
                325                 330                 335

Gln Pro Leu Pro Glu Val Ser Pro Ala Glu Asn Pro Ala Asn Asn Pro
            340                 345                 350

Asp Pro Asp Glu Asn Pro Gly Thr Arg Pro Asn Pro Glu Pro Asp Pro
        355                 360                 365

Asp Leu Asn Pro Asp Ala Asn Pro Asp Thr Asp Gly Gln Pro Gly Thr
    370                 375                 380

Ser Pro Asp Ser Pro Ala Val Pro Asp Arg Pro Asn Gly Arg His Arg
385                 390                 395                 400

Lys Glu Arg Lys Glu Gly Glu Asp Gly Gly Leu Ser Cys Asp Tyr Phe
                405                 410                 415

Pro Glu Ile Leu Ala Cys Gln Glu Met Gly Lys Pro Ser Asp Arg Met
            420                 425                 430

Phe His Asp Ile Ser Ile Pro Gln Val Thr Asp Lys Thr Trp Ser
435                 440                 445

Ser His Asn Phe Leu Pro Ser Asn Gly Val Cys Pro Gln Pro Lys Thr
    450                 455                 460

Phe His Val Phe Gly Arg Gln Tyr Arg Ala Ser Tyr Glu Pro Leu Cys
465                 470                 475                 480

Val Phe Ala Glu Lys Ile Arg Phe Ala Val Leu Leu Ala Phe Ile Ile
                485                 490                 495

Met Ser Ala Phe Val Val Phe Gly Ser Leu Gly Gly Glu
            500                 505

<210> SEQ ID NO 9
<211> LENGTH: 526
<212> TYPE: PRT
<213> ORGANISM: Neisseria gonorrheae

<400> SEQUENCE: 9

Met Val Thr Lys His Thr Asn Leu Asn Phe Ala Lys Leu Ser Ile Ile
1               5                   10                  15

Ala Ile Leu Met Met Tyr Ser Phe Glu Ala Asn Ala Asn Ala Val Lys
            20                  25                  30

Ile Ser Glu Thr Leu Ser Val Asp Thr Gly Gln Gly Ala Lys Val His
        35                  40                  45

Lys Phe Val Pro Lys Ser Ser Asn Ile Tyr Ser Ser Asp Leu Thr Lys
    50                  55                  60

Ala Val Asp Leu Thr His Ile Pro Thr Gly Ala Lys Ala Arg Ile Asn
65                  70                  75                  80

Ala Lys Ile Thr Ala Ser Val Ser Arg Ala Gly Val Leu Ser Gly Val
                85                  90                  95

Gly Lys Leu Val Arg Gln Gly Ala Lys Phe Gly Thr Arg Ala Val Pro
            100                 105                 110

Tyr Val Gly Thr Ala Leu Leu Ala His Asp Val Tyr Glu Thr Phe Lys
        115                 120                 125

Glu Asp Ile Gln Ala Arg Gly Cys Arg Tyr Asp Pro Glu Thr Asp Lys
            130                 135                 140

Phe Val Lys Gly Tyr Glu Tyr Ala Asn Cys Leu Trp Tyr Glu Asp Glu
145                 150                 155                 160

Arg Arg Ile Asn Arg Thr Tyr Gly Cys Tyr Gly Val Asp Ser Ser Ile
                165                 170                 175

Met Arg Leu Met Pro Asp Arg Ser Arg Phe Pro Glu Val Lys Gln Leu
            180                 185                 190

Met Glu Ser Gln Met Tyr Arg Leu Ala Arg Pro Phe Trp Asn Trp Arg
        195                 200                 205

Lys Glu Glu Leu Asn Lys Leu Ser Ser Leu Asp Trp Asn Asn Phe Val
210                 215                 220

Leu Asn Arg Cys Thr Phe Asp Trp Asn Gly Gly Cys Ala Val Asn
225                 230                 235                 240

Lys Gly Asp Asp Phe Arg Ala Gly Ala Ser Phe Ser Leu Gly Arg Asn
                245                 250                 255

Pro Lys Tyr Lys Glu Glu Met Asp Ala Lys Lys Pro Glu Glu Ile Leu
            260                 265                 270

Ser Leu Lys Val Asp Ala Asp Pro Asp Lys Tyr Ile Glu Ala Thr Gly
        275                 280                 285

Tyr Pro Gly Tyr Ser Glu Lys Val Glu Val Ala Pro Gly Thr Lys Val
290                 295                 300

Asn Met Gly Pro Val Thr Asp Arg Asn Gly Asn Pro Val Gln Val Ala
305                 310                 315                 320

Ala Thr Phe Gly Arg Asp Ala Gln Gly Asn Thr Thr Ala Asp Val Gln
                325                 330                 335

Val Ile Pro Arg Pro Asp Leu Thr Pro Ala Ser Ala Glu Ala Pro His
            340                 345                 350

Ala Gln Pro Leu Pro Glu Val Ser Pro Ala Glu Asn Pro Ala Asn Asn
        355                 360                 365

Pro Asp Pro Asp Glu Asn Pro Gly Thr Arg Pro Asn Pro Glu Pro Asp
370                 375                 380

Pro Asp Leu Asn Pro Asp Ala Asn Pro Asp Thr Asp Gly Gln Pro Gly
385                 390                 395                 400

Thr Ser Pro Asp Ser Pro Ala Val Pro Asp Arg Pro Asn Gly Arg His
                405                 410                 415

Arg Lys Glu Arg Lys Glu Gly Glu Asp Gly Gly Leu Ser Cys Asp Tyr
            420                 425                 430

Phe Pro Glu Ile Leu Ala Cys Gln Glu Met Gly Lys Pro Ser Asp Arg
        435                 440                 445

Met Phe His Asp Ile Ser Ile Pro Gln Val Thr Asp Asp Lys Thr Trp
450                 455                 460

Ser Ser His Asn Phe Leu Pro Ser Asn Gly Val Cys Pro Gln Pro Lys
465                 470                 475                 480

Thr Phe His Val Phe Gly Arg Gln Tyr Arg Ala Ser Tyr Glu Pro Leu
                485                 490                 495

Cys Val Phe Ala Glu Lys Ile Arg Phe Ala Val Leu Leu Ala Phe Ile
            500                 505                 510

Ile Met Ser Ala Phe Val Val Phe Gly Ser Leu Gly Gly Glu
        515                 520                 525

<210> SEQ ID NO 10
<211> LENGTH: 507
<212> TYPE: PRT
<213> ORGANISM: Neisseria gonorrheae

<400> SEQUENCE: 10

```
Met Met Tyr Ser Phe Glu Ala Asn Ala Asn Ala Val Lys Ile Ser Glu
 1               5                  10                  15

Thr Leu Ser Val Asp Thr Gly Gln Gly Ala Lys Val His Lys Phe Val
             20                  25                  30

Pro Lys Ser Ser Asn Ile Tyr Ser Ser Asp Leu Thr Lys Ala Val Asp
         35                  40                  45

Leu Thr His Ile Pro Thr Gly Ala Lys Ala Arg Ile Asn Ala Lys Ile
     50                  55                  60

Thr Ala Ser Val Ser Arg Ala Gly Val Leu Ser Gly Val Gly Lys Leu
 65                  70                  75                  80

Val Arg Gln Gly Ala Lys Phe Gly Thr Arg Ala Val Pro Tyr Val Gly
                 85                  90                  95

Thr Ala Leu Leu Ala His Asp Val Tyr Glu Thr Phe Lys Glu Asp Ile
            100                 105                 110

Gln Ala Arg Gly Cys Arg Tyr Asp Pro Glu Thr Asp Lys Phe Val Lys
        115                 120                 125

Gly Tyr Glu Tyr Ala Asn Cys Leu Trp Tyr Asp Glu Arg Arg Ile
130                 135                 140

Asn Arg Thr Tyr Gly Cys Tyr Gly Val Asp Ser Ser Ile Met Arg Leu
145                 150                 155                 160

Met Pro Asp Arg Ser Arg Phe Pro Glu Val Lys Gln Leu Met Glu Ser
                165                 170                 175

Gln Met Tyr Arg Leu Ala Arg Pro Phe Trp Asn Trp Lys Glu Glu
        180                 185                 190

Leu Asn Lys Leu Ser Ser Leu Asp Trp Asn Asn Phe Val Leu Asn Arg
        195                 200                 205

Cys Thr Phe Asp Trp Asn Gly Gly Cys Ala Val Asn Lys Gly Asp
        210                 215                 220

Asp Phe Arg Ala Gly Ala Ser Phe Ser Leu Gly Arg Asn Pro Lys Tyr
225                 230                 235                 240

Lys Glu Glu Met Asp Ala Lys Pro Glu Glu Ile Leu Ser Leu Lys
                245                 250                 255

Val Asp Ala Asp Pro Asp Lys Tyr Ile Glu Ala Thr Gly Tyr Pro Gly
                260                 265                 270

Tyr Ser Glu Lys Val Glu Val Ala Pro Gly Thr Lys Val Asn Met Gly
        275                 280                 285

Pro Val Thr Asp Arg Asn Gly Asn Pro Val Gln Val Ala Ala Thr Phe
        290                 295                 300

Gly Arg Asp Ala Gln Gly Asn Thr Thr Ala Asp Val Gln Val Ile Pro
305                 310                 315                 320

Arg Pro Asp Leu Thr Pro Ala Ser Ala Glu Ala Pro His Ala Gln Pro
                325                 330                 335

Leu Pro Glu Val Ser Pro Ala Glu Asn Pro Ala Asn Pro Asp Pro
        340                 345                 350

Asp Glu Asn Pro Gly Thr Arg Pro Asn Pro Glu Pro Asp Pro Asp Leu
        355                 360                 365

Asn Pro Asp Ala Asn Pro Asp Thr Asp Gly Gln Pro Gly Thr Ser Pro
        370                 375                 380

Asp Ser Pro Ala Val Pro Asp Arg Pro Asn Gly Arg His Arg Lys Glu
385                 390                 395                 400

Arg Lys Glu Gly Glu Asp Gly Gly Leu Ser Cys Asp Tyr Phe Pro Glu
                405                 410                 415
```

```
Ile Leu Ala Cys Gln Glu Met Gly Lys Pro Ser Asp Arg Met Phe His
            420                 425                 430

Asp Ile Ser Ile Pro Gln Val Thr Asp Asp Lys Thr Trp Ser Ser His
            435                 440                 445

Asn Phe Leu Pro Ser Asn Gly Val Cys Pro Gln Pro Lys Thr Phe His
450                 455                 460

Val Phe Gly Arg Gln Tyr Arg Ala Ser Tyr Glu Pro Leu Cys Val Phe
465                 470                 475                 480

Ala Glu Lys Ile Arg Phe Ala Val Leu Leu Ala Phe Ile Ile Met Ser
            485                 490                 495

Ala Phe Val Val Phe Gly Ser Leu Gly Gly Glu
            500                 505

<210> SEQ ID NO 11
<211> LENGTH: 501
<212> TYPE: PRT
<213> ORGANISM: Neisseria meningitidis

<400> SEQUENCE: 11

Met Tyr Ala Leu Ser Glu Lys Tyr Asn Asp Asn Gly Phe Lys Ala Tyr
1               5                   10                  15

Lys Val Leu Gly Glu Gly Gly Ile His Thr Glu Tyr Asn Tyr Lys
            20                  25                  30

Phe Asp Lys Ser Leu Asn Leu Asn Val Leu Glu Ser Ser Thr Gly Ala
            35                  40                  45

Arg Ser Leu Glu Lys Val Pro Val Lys Val Thr Ala Ser Val Ser Arg
50                  55                  60

Ala Ala Val Leu Ser Gly Val Gly Lys Leu Ala Arg Leu Gly Ala Lys
65                  70                  75                  80

Leu Ser Thr Arg Ala Val Pro Tyr Val Gly Thr Ala Leu Leu Ala His
            85                  90                  95

Asp Val Tyr Glu Thr Phe Lys Glu Asp Ile Gln Ala Gln Gly Tyr Gln
            100                 105                 110

Tyr Asp Pro Glu Thr Asp Lys Phe Val Lys Gly Tyr Glu Tyr Ser Asn
            115                 120                 125

Cys Leu Trp Tyr Glu Asp Lys Arg Arg Ile Asn Arg Thr Tyr Gly Cys
130                 135                 140

Tyr Gly Val Asp Ser Ser Ile Met Arg Leu Met Ser Asp Asp Ser Arg
145                 150                 155                 160

Phe Pro Glu Val Lys Glu Leu Met Glu Ser Gln Met Tyr Arg Leu Ala
            165                 170                 175

Arg Pro Phe Trp Asn Trp His Lys Glu Glu Leu Asn Lys Leu Ser Ser
            180                 185                 190

Leu Asp Trp Asn Asn Phe Val Leu Asn Arg Cys Thr Phe Asn Trp Asn
            195                 200                 205

Gly Gly Asp Cys Leu Val Asn Lys Gly Asp Phe Arg Asn Gly Ala
            210                 215                 220

Asp Phe Ser Leu Ile Arg Asn Ser Lys Tyr Lys Glu Glu Met Asp Ala
225                 230                 235                 240

Lys Lys Leu Glu Glu Ile Leu Ser Leu Lys Val Asp Ala Asn Pro Asp
            245                 250                 255

Lys Tyr Ile Lys Ala Thr Gly Tyr Pro Gly Tyr Ser Glu Lys Val Glu
            260                 265                 270

Val Ala Pro Gly Thr Lys Val Asn Met Gly Pro Val Thr Asp Arg Asn
            275                 280                 285
```

```
Gly Asn Pro Val Gln Val Ala Thr Phe Gly Arg Asp Ser Gln Gly
        290                 295                 300

Asn Thr Thr Val Asp Val Gln Val Ile Pro Arg Pro Asp Leu Thr Pro
305                 310                 315                 320

Gly Ser Ala Glu Ala Pro Asn Ala Gln Pro Leu Pro Glu Val Ser Pro
            325                 330                 335

Ala Glu Asn Pro Ala Asn Asn Pro Asn Pro Asn Glu Asn Pro Gly Thr
            340                 345                 350

Ser Pro Asn Pro Glu Pro Asp Pro Asp Leu Asn Pro Asp Ala Asn Pro
            355                 360                 365

Asp Thr Asp Gly Gln Pro Gly Thr Arg Pro Asp Ser Pro Ala Val Pro
370                 375                 380

Asp Arg Pro Asn Gly Arg His Arg Lys Glu Arg Lys Glu Gly Glu Asp
385                 390                 395                 400

Gly Gly Leu Leu Cys Asp Tyr Phe Pro Glu Ile Leu Ala Cys Gln Glu
                405                 410                 415

Met Gly Lys Pro Ser Asp Gly Met Phe His Asp Ile Ser Ile Pro Gln
                420                 425                 430

Val Ile Asp Asp Lys Thr Trp Ser His Asn Phe Leu Pro Ser Asn
                435                 440                 445

Gly Val Cys Pro Gln Pro Lys Thr Phe His Val Phe Gly Arg Gln Tyr
            450                 455                 460

Gln Ala Ser Tyr Glu Pro Leu Cys Val Phe Ala Glu Lys Ile Arg Phe
465                 470                 475                 480

Ala Val Leu Leu Ala Phe Ile Ile Met Ser Ala Phe Val Val Phe Gly
                485                 490                 495

Ser Leu Lys Gly Lys
            500

<210> SEQ ID NO 12
<211> LENGTH: 504
<212> TYPE: PRT
<213> ORGANISM: Neisseria meningitidis

<400> SEQUENCE: 12

Met Glu Leu Lys Leu Lys Arg Leu Ile Leu Ile Leu Met Leu Gly Met
1               5                   10                  15

Phe Ser Val Asn Ser Tyr Ala Glu Arg Phe Lys Tyr Pro Ile Gly Asn
                20                  25                  30

Ser Asp Val Arg Leu Asp Ile Asp His Thr Lys Ser Val Val Thr Asp
            35                  40                  45

Phe Arg Val Asp Gly Gln Arg Phe Ser Gly Arg Ile Ile Glu Pro Ser
    50                  55                  60

Ile Ile Glu His Val Pro Thr Gly Ala Arg Ser Leu Glu Lys Ile Pro
65                  70                  75                  80

Val Lys Val Thr Ala Ser Val Ser Arg Ala Gly Val Leu Ala Gly Val
                85                  90                  95

Gly Ala Leu Val Arg Gln Gly Ala Lys Leu Gly Lys Arg Ala Val Pro
            100                 105                 110

Tyr Val Gly Thr Ala Leu Leu Ala Tyr Asp Ile Tyr Glu Thr Phe Lys
        115                 120                 125

Asp Glu Ile Lys Glu Gln Gly Tyr Gln Tyr Asp Pro Glu Thr Asp Lys
    130                 135                 140

Phe Val Lys Gly Tyr Glu Tyr Ser Asn Cys Ile Trp Glu His Ala Glu
145                 150                 155                 160
```

Asn Gly Ile Lys Thr Tyr Gly Cys Tyr Gly Val Asp Ser Ser Ile Met
            165                 170                 175

Arg Leu Met Ser Asp Tyr Ser Arg Phe Pro Glu Val Lys Glu Leu Met
            180                 185                 190

Glu His Gln Met Glu Ile Val Gly Arg Asn Tyr Trp Glu Met Val Arg
            195                 200                 205

Lys Asn Arg Asn Asp Ser Phe Arg Asn Tyr Asn Phe Ser Arg Cys Tyr
        210                 215                 220

Phe Asn Trp Asn Gly Gly Asn Cys Asn Ile Gly Glu Asp Ile Asn Asp
225                 230                 235                 240

Ala Arg Ser Phe Ile Asn Phe Ser Leu Ile Arg Asn Pro Lys Tyr Lys
                245                 250                 255

Glu Glu Met Asp Ala Lys Lys Leu Glu Glu Ile Leu Ala Leu Lys Val
            260                 265                 270

Asp Ala Asn Pro Asp Lys Tyr Ile Gln Ala Thr Gly Tyr Pro Gly Tyr
            275                 280                 285

Ser Glu Lys Val Glu Val Ala Pro Gly Thr Lys Val Asn Met Gly Pro
        290                 295                 300

Val Thr Asp Arg Asn Gly Asn Pro Val Gln Val Ala Thr Phe Gly
305                 310                 315                 320

Arg Asp Ser Gln Gly Asn Thr Thr Val Asp Val Gln Val Ile Pro Arg
                325                 330                 335

Pro Asp Leu Thr Pro Gly Ser Ala Glu Ala Pro Glu Thr Lys Pro Lys
            340                 345                 350

Pro Ala Pro Thr Pro Glu Thr Asn Pro Lys Glu Lys Glu Asn Pro Arg
        355                 360                 365

Glu Glu Asp Gln Asp Asn Pro Lys Pro Thr Pro Thr Pro Gly Glu Thr
            370                 375                 380

Pro Ser Pro Asn Glu Ser Pro Lys Asp Arg Arg Glu Glu Lys Lys Pro
385                 390                 395                 400

Asp Gly Asn Gly Gly Leu Leu Cys Asp Leu Phe Pro Lys Ile Leu Ala
                405                 410                 415

Cys Ala Glu Met Gly Glu Pro Ser Glu Asn Asp Phe Glu Gly Ile Ala
            420                 425                 430

Ile Pro Lys Ala Val Asn Glu Glu Thr Trp Ser Pro Asp Asn Met Phe
        435                 440                 445

Pro Ser Ser Gly Val Cys Pro Lys Asp Lys Thr Phe His Val Phe Gly
450                 455                 460

Lys Ala Phe Ser Val Ser Tyr Gln Pro Leu Cys Thr Leu Met Glu Asn
465                 470                 475                 480

Val Arg Phe Ala Val Ile Ile Gly Phe Ile Ile Met Ser Ala Phe Ile
                485                 490                 495

Thr Phe Gly Ser Leu Arg Lys Glu
            500

<210> SEQ ID NO 13
<211> LENGTH: 59
<212> TYPE: PRT
<213> ORGANISM: Neisseria meningitidis

<400> SEQUENCE: 13

Met Glu Arg Leu Ala Arg Pro Tyr Trp Glu Lys Leu Arg Asn Arg Pro
1               5                   10                  15

Asp Met Tyr Tyr Phe Lys Asn Tyr Asn Phe Lys Arg Cys Tyr Phe Gly
            20                  25                  30

```
Leu Asn Gly Gly Asp Cys Leu Val Ala Lys Gly Asp Gly Arg Thr
            35                  40                  45

Phe Ile Ser Phe Ser Leu Gln Gly Asn Ser Lys
 50                  55
```

<210> SEQ ID NO 14
<211> LENGTH: 62
<212> TYPE: PRT
<213> ORGANISM: Neisseria meningitidis

<400> SEQUENCE: 14

```
Met Tyr Arg Leu Ala Arg Pro Phe Trp Asn Trp His Lys Glu Glu Leu
 1               5                  10                  15

Asn Lys Leu Ser Ser Leu Asp Trp Asn Asn Phe Val Leu Asn Ser Cys
            20                  25                  30

Thr Phe Asp Trp Asn Gly Gly Asp Cys Val Val Asn Lys Gly Asp Asp
            35                  40                  45

Phe Arg Asn Gly Ala Asp Phe Ser Leu Ile Arg Asn Ser Lys
 50                  55                  60
```

<210> SEQ ID NO 15
<211> LENGTH: 62
<212> TYPE: PRT
<213> ORGANISM: Neisseria meningitidis

<400> SEQUENCE: 15

```
Met Tyr Arg Leu Ala Arg Pro Phe Trp Asn Trp His Lys Glu Glu Leu
 1               5                  10                  15

Asn Lys Leu Ser Ser Leu Asp Trp Asn Asn Phe Val Leu Asn Arg Cys
            20                  25                  30

Thr Phe Asp Trp Asn Gly Gly Asp Cys Val Val Asn Lys Gly Asp Asp
            35                  40                  45

Tyr Arg Asn Gly Ala Asn Phe Ser Leu Ser Arg Asn Pro Lys
 50                  55                  60
```

<210> SEQ ID NO 16
<211> LENGTH: 62
<212> TYPE: PRT
<213> ORGANISM: Neisseria meningitidis

<400> SEQUENCE: 16

```
Met Tyr Arg Leu Ala Arg Pro Phe Trp Asn Trp His Lys Glu Glu Leu
 1               5                  10                  15

Asn Lys Leu Ser Ser Leu Asp Trp Asn Asn Phe Val Leu Asn Arg Cys
            20                  25                  30

Thr Phe Asp Trp Asn Gly Gly Asp Cys Val Val Asn Lys Gly Asp Asp
            35                  40                  45

Tyr Arg Asn Gly Ala Asn Phe Ser Leu Ser Arg Asn Pro Lys
 50                  55                  60
```

<210> SEQ ID NO 17
<211> LENGTH: 62
<212> TYPE: PRT
<213> ORGANISM: Neisseria meningitidis

<400> SEQUENCE: 17

```
Met Tyr Arg Leu Ala Arg Pro Phe Trp Asn Trp His Lys Glu Glu Leu
 1               5                  10                  15

Asn Lys Leu Ser Ser Leu Asp Trp Asn Asn Phe Val Leu Asn Arg Cys
            20                  25                  30
```

Thr Phe Asn Trp Asn Gly Gly Asp Cys Leu Val Asn Lys Gly Asp Asp
            35                  40                  45

Phe Arg Asn Gly Ala Asp Phe Ser Leu Ile Arg Asn Ser Lys
    50                  55                  60

<210> SEQ ID NO 18
<211> LENGTH: 62
<212> TYPE: PRT
<213> ORGANISM: Neisseria meningitidis

<400> SEQUENCE: 18

Met Tyr Arg Leu Ala Arg Pro Phe Trp Asn Trp His Lys Glu Glu Leu
1               5                   10                  15

Asn Lys Leu Ser Ser Leu Asp Trp Asn Asn Phe Val Leu Asn Arg Cys
            20                  25                  30

Thr Phe Asn Trp Asn Gly Gly Asp Cys Leu Val Asn Lys Gly Asp Asp
            35                  40                  45

Phe Arg Asn Gly Ala Asp Phe Ser Leu Ile Arg Asn Ser Lys
    50                  55                  60

<210> SEQ ID NO 19
<211> LENGTH: 62
<212> TYPE: PRT
<213> ORGANISM: Neisseria gonorrheae

<400> SEQUENCE: 19

Met Tyr Arg Leu Ala Arg Pro Phe Trp Asn Trp Arg Lys Glu Glu Leu
1               5                   10                  15

Asn Lys Leu Ser Ser Leu Asp Trp Asn Asn Phe Val Leu Asn Arg Cys
            20                  25                  30

Thr Phe Asp Trp Asn Gly Gly Gly Cys Ala Val Asn Lys Gly Asp Asp
            35                  40                  45

Phe Arg Ala Gly Ala Ser Phe Ser Leu Gly Arg Asn Pro Lys
    50                  55                  60

<210> SEQ ID NO 20
<211> LENGTH: 62
<212> TYPE: PRT
<213> ORGANISM: Neisseria gonorrheae

<400> SEQUENCE: 20

Met Tyr Arg Leu Ala Arg Pro Phe Trp Asn Trp Arg Lys Glu Glu Leu
1               5                   10                  15

Asn Lys Leu Ser Ser Leu Asp Trp Asn Asn Phe Val Leu Asn Arg Cys
            20                  25                  30

Thr Phe Asp Trp Asn Gly Gly Cys Ala Val Asn Lys Gly Asp Asp
            35                  40                  45

Phe Arg Ala Gly Ala Ser Phe Ser Leu Gly Arg Asn Pro Lys
    50                  55                  60

<210> SEQ ID NO 21
<211> LENGTH: 62
<212> TYPE: PRT
<213> ORGANISM: Neisseria gonorrheae

<400> SEQUENCE: 21

Met Tyr Arg Leu Ala Arg Pro Phe Trp Asn Trp Arg Lys Glu Glu Leu
1               5                   10                  15

Asn Lys Leu Ser Ser Leu Asp Trp Asn Asn Phe Val Leu Asn Arg Cys
            20                  25                  30

Thr Phe Asp Trp Asn Gly Gly Gly Cys Ala Val Asn Lys Gly Asp Asp
            35                  40                  45

Phe Arg Ala Gly Ala Ser Phe Ser Leu Gly Arg Asn Pro Lys
 50                  55                  60

<210> SEQ ID NO 22
<211> LENGTH: 59
<212> TYPE: PRT
<213> ORGANISM: Neisseria meningitidis

<400> SEQUENCE: 22

Met Glu Ile Val Gly Arg Asn Tyr Trp Glu Met Val Arg Lys Asn Arg
 1               5                  10                  15

Asn Asp Ser Phe Arg Asn Tyr Asn Phe Ser Arg Cys Tyr Phe Asn Trp
            20                  25                  30

Asn Gly Gly Asn Cys Asn Ile Gly Glu Asp Ile Asn Asp Ala Arg Ser
        35                  40                  45

Phe Ile Asn Phe Ser Leu Ile Arg Asn Pro Lys
    50                  55

<210> SEQ ID NO 23
<211> LENGTH: 111
<212> TYPE: PRT
<213> ORGANISM: Neisseria meningitidis

<400> SEQUENCE: 23

Ser Val Ser Arg Ala Gly Val Leu Ala Gly Val Gly Lys Leu Ala Arg
 1               5                  10                  15

Leu Gly Ala Lys Phe Ser Thr Arg Ala Val Pro Tyr Val Gly Thr Ala
            20                  25                  30

Leu Leu Ala His Asp Val Tyr Glu Thr Phe Lys Glu Asp Ile Gln Ala
        35                  40                  45

Gln Gly Tyr Gln Tyr Asp Pro Gly Thr Asp Lys Phe Val Lys Gly Tyr
    50                  55                  60

Glu Tyr Ser Asn Cys Leu Trp Tyr Glu Asp Glu Arg Arg Ile Asn Arg
65                  70                  75                  80

Thr Tyr Gly Cys Tyr Gly Val Asp Ser Ser Ile Met Arg Leu Met Ser
                85                  90                  95

Asp Tyr Ser Arg Phe Pro Glu Val Lys Glu Leu Met Glu Ser Gln
            100                 105                 110

<210> SEQ ID NO 24
<211> LENGTH: 111
<212> TYPE: PRT
<213> ORGANISM: Neisseria meningitidis

<400> SEQUENCE: 24

Ser Val Ser Arg Ala Gly Val Leu Ala Gly Val Gly Lys Leu Ala Arg
 1               5                  10                  15

Leu Gly Ala Lys Phe Ser Thr Arg Ala Val Pro Tyr Val Gly Thr Ala
            20                  25                  30

Leu Leu Ala His Asp Val Tyr Glu Thr Phe Lys Glu Asp Ile Gln Ala
        35                  40                  45

Arg Gly Tyr Gln Tyr Asp Pro Gly Thr Asp Lys Phe Val Lys Gly Tyr
    50                  55                  60

Glu Tyr Ser Asn Cys Leu Trp Tyr Glu Asp Glu Arg Arg Ile Asn Arg
65                  70                  75                  80

Thr Tyr Gly Cys Tyr Gly Val Asp Ser Ser Ile Met Arg Leu Met Ser

```
                        85                  90                  95
Asp Tyr Ser Arg Phe Pro Glu Val Lys Glu Leu Met Glu Ser Gln
                100                 105                 110

<210> SEQ ID NO 25
<211> LENGTH: 111
<212> TYPE: PRT
<213> ORGANISM: Neisseria meningitidis

<400> SEQUENCE: 25

Ser Val Ser Arg Ala Ala Val Leu Ser Gly Val Gly Lys Leu Val Arg
1               5                   10                  15

Gln Gly Ala Lys Phe Ser Thr Arg Ala Val Pro Tyr Val Gly Thr Ala
                20                  25                  30

Leu Leu Ala His Asp Val Tyr Glu Thr Phe Lys Glu Asp Ile Gln Ala
            35                  40                  45

Arg Gly Tyr Gln Tyr Asp Thr Glu Thr Asp Lys Phe Val Lys Gly Tyr
        50                  55                  60

Glu Tyr Ser Asn Cys Leu Trp Tyr Glu Asp Glu Arg Arg Ile Asn Arg
65                  70                  75                  80

Thr Tyr Gly Cys Tyr Gly Val Asp Ser Ser Ile Met Arg Leu Met Ser
                85                  90                  95

Asp Tyr Ser Arg Phe Pro Glu Val Lys Glu Leu Met Glu Ser Gln
                100                 105                 110

<210> SEQ ID NO 26
<211> LENGTH: 111
<212> TYPE: PRT
<213> ORGANISM: Neisseria meningitidis

<400> SEQUENCE: 26

Ser Val Ser Arg Ala Gly Val Leu Ala Gly Val Gly Lys Leu Ala Arg
1               5                   10                  15

Leu Gly Ala Lys Phe Ser Thr Arg Ala Val Pro Tyr Val Gly Thr Ala
                20                  25                  30

Leu Leu Ala His Asp Val Tyr Glu Thr Phe Lys Glu Asp Ile Gln Ala
            35                  40                  45

Gln Gly Tyr Gln Tyr Asp Pro Glu Thr Asp Lys Phe Val Lys Gly Tyr
        50                  55                  60

Glu Tyr Ser Asn Cys Leu Trp Tyr Glu Asp Glu Arg Arg Ile Asn Arg
65                  70                  75                  80

Thr Tyr Gly Cys Tyr Gly Val Asp Ser Ser Ile Met Arg Leu Met Ser
                85                  90                  95

Asp Tyr Ser Arg Phe Pro Glu Val Lys Glu Leu Met Glu Ser Gln
                100                 105                 110

<210> SEQ ID NO 27
<211> LENGTH: 111
<212> TYPE: PRT
<213> ORGANISM: Neisseria meningitidis

<400> SEQUENCE: 27

Ser Val Ser Arg Ala Gly Val Leu Ala Gly Val Gly Lys Leu Ala Arg
1               5                   10                  15

Leu Gly Ala Lys Phe Ser Thr Arg Ala Val Pro Tyr Val Gly Thr Ala
                20                  25                  30

Leu Leu Ala His Asp Val Tyr Glu Thr Phe Lys Glu Asp Ile Gln Ala
            35                  40                  45
```

```
Gln Gly Tyr Gln Tyr Asp Pro Glu Thr Asp Lys Phe Val Lys Gly Tyr
    50                  55                  60

Glu Tyr Ser Asn Cys Leu Trp Tyr Glu Asp Arg Arg Ile Asn Arg
 65                  70                  75                  80

Thr Tyr Gly Cys Tyr Gly Val Asp Ser Ser Ile Met Arg Leu Met Ser
                 85                  90                  95

Asp Tyr Ser Arg Phe Pro Glu Val Lys Glu Leu Met Glu Ser Gln
            100                 105                 110

<210> SEQ ID NO 28
<211> LENGTH: 111
<212> TYPE: PRT
<213> ORGANISM: Neisseria meningitidis

<400> SEQUENCE: 28

Ser Val Ser Arg Ala Ala Val Leu Ser Gly Val Gly Lys Leu Ala Arg
 1               5                  10                  15

Leu Gly Ala Lys Leu Ser Thr Arg Ala Val Pro Tyr Val Gly Thr Ala
                20                  25                  30

Leu Leu Ala His Asp Val Tyr Glu Thr Phe Lys Glu Asp Ile Gln Ala
            35                  40                  45

Gln Gly Tyr Gln Tyr Asp Pro Glu Thr Asp Lys Phe Val Lys Gly Tyr
    50                  55                  60

Glu Tyr Ser Asn Cys Leu Trp Tyr Glu Asp Lys Arg Ile Asn Arg
 65                  70                  75                  80

Thr Tyr Gly Cys Tyr Gly Val Asp Ser Ser Ile Met Arg Leu Met Ser
                 85                  90                  95

Asp Asp Ser Arg Phe Pro Glu Val Lys Glu Leu Met Glu Ser Gln
            100                 105                 110

<210> SEQ ID NO 29
<211> LENGTH: 111
<212> TYPE: PRT
<213> ORGANISM: Neisseria meningitidis

<400> SEQUENCE: 29

Ser Val Ser Arg Ala Ala Val Leu Ser Gly Val Gly Lys Leu Ala Arg
 1               5                  10                  15

Leu Gly Ala Lys Leu Ser Thr Arg Ala Val Pro Tyr Val Gly Thr Ala
                20                  25                  30

Leu Leu Ala His Asp Val Tyr Glu Thr Phe Lys Glu Asp Ile Gln Ala
            35                  40                  45

Gln Gly Tyr Gln Tyr Asp Pro Glu Thr Asp Lys Phe Val Lys Gly Tyr
    50                  55                  60

Glu Tyr Ser Asn Cys Leu Trp Tyr Glu Asp Lys Arg Ile Asn Arg
 65                  70                  75                  80

Thr Tyr Gly Cys Tyr Gly Val Asp Ser Ser Ile Met Arg Leu Met Ser
                 85                  90                  95

Asp Asp Ser Arg Phe Pro Glu Val Lys Glu Leu Met Glu Ser Gln
            100                 105                 110

<210> SEQ ID NO 30
<211> LENGTH: 111
<212> TYPE: PRT
<213> ORGANISM: Neisseria meningitidis

<400> SEQUENCE: 30

Ser Val Ser Arg Ala Gly Val Leu Ala Gly Val Gly Lys Leu Ala Arg
 1               5                  10                  15
```

Leu Gly Ala Lys Leu Ser Thr Arg Ala Val Pro Tyr Val Gly Thr Ala
                20                  25                  30

Leu Leu Ala His Asp Val Tyr Glu Thr Phe Lys Glu Asp Ile Gln Ala
            35                  40                  45

Gln Gly Tyr Gln Tyr Asp Pro Glu Thr Asp Lys Phe Val Lys Gly Tyr
50                  55                  60

Glu Tyr Ser Asn Cys Leu Trp Tyr Glu Asp Lys Arg Arg Ile Asn Arg
65                  70                  75                  80

Thr Tyr Gly Cys Tyr Gly Val Asp Ser Ser Ile Met Arg Leu Met Ser
                85                  90                  95

Asp Asp Ser Arg Phe Pro Glu Val Lys Glu Leu Met Glu Ser Gln
                100                 105                 110

<210> SEQ ID NO 31
<211> LENGTH: 111
<212> TYPE: PRT
<213> ORGANISM: Neisseria gonorrheae

<400> SEQUENCE: 31

Ser Val Ser Arg Ala Gly Val Leu Ser Gly Val Gly Lys Leu Val Arg
1               5                   10                  15

Gln Gly Ala Lys Phe Gly Thr Arg Ala Val Pro Tyr Val Gly Thr Ala
                20                  25                  30

Leu Leu Ala His Asp Val Tyr Glu Thr Phe Lys Glu Asp Ile Gln Ala
            35                  40                  45

Arg Gly Cys Arg Tyr Asp Pro Glu Thr Asp Lys Phe Val Lys Gly Tyr
50                  55                  60

Glu Tyr Ala Asn Cys Leu Trp Tyr Glu Asp Glu Arg Arg Ile Asn Arg
65                  70                  75                  80

Thr Tyr Gly Cys Tyr Gly Val Asp Ser Ser Ile Met Arg Leu Met Pro
                85                  90                  95

Asp Arg Ser Arg Phe Pro Glu Val Lys Gln Leu Met Glu Ser Gln
                100                 105                 110

<210> SEQ ID NO 32
<211> LENGTH: 111
<212> TYPE: PRT
<213> ORGANISM: Neisseria gonorrheae

<400> SEQUENCE: 32

Ser Val Ser Arg Ala Gly Val Leu Ser Gly Val Gly Lys Leu Val Arg
1               5                   10                  15

Gln Gly Ala Lys Phe Gly Thr Arg Ala Val Pro Tyr Val Gly Thr Ala
                20                  25                  30

Leu Leu Ala His Asp Val Tyr Glu Thr Phe Lys Glu Asp Ile Gln Ala
            35                  40                  45

Arg Gly Cys Arg Tyr Asp Pro Glu Thr Asp Lys Phe Val Lys Gly Tyr
50                  55                  60

Glu Tyr Ala Asn Cys Leu Trp Tyr Glu Asp Glu Arg Arg Ile Asn Arg
65                  70                  75                  80

Thr Tyr Gly Cys Tyr Gly Val Asp Ser Ser Ile Met Arg Leu Met Pro
                85                  90                  95

Asp Arg Ser Arg Phe Pro Glu Val Lys Gln Leu Met Glu Ser Gln
                100                 105                 110

<210> SEQ ID NO 33
<211> LENGTH: 111

```
<212> TYPE: PRT
<213> ORGANISM: Neisseria gonorrheae

<400> SEQUENCE: 33

Ser Val Ser Arg Ala Gly Val Leu Ser Gly Val Gly Lys Leu Val Arg
 1               5                  10                  15

Gln Gly Ala Lys Phe Gly Thr Arg Ala Val Pro Tyr Val Gly Thr Ala
             20                  25                  30

Leu Leu Ala His Asp Val Tyr Glu Thr Phe Lys Glu Asp Ile Gln Ala
         35                  40                  45

Arg Gly Cys Arg Tyr Asp Pro Glu Thr Asp Lys Phe Val Lys Gly Tyr
     50                  55                  60

Glu Tyr Ala Asn Cys Leu Trp Tyr Glu Asp Glu Arg Arg Ile Asn Arg
 65                  70                  75                  80

Thr Tyr Gly Cys Tyr Gly Val Asp Ser Ser Ile Met Arg Leu Met Pro
                 85                  90                  95

Asp Arg Ser Arg Phe Pro Glu Val Lys Gln Leu Met Glu Ser Gln
            100                 105                 110

<210> SEQ ID NO 34
<211> LENGTH: 110
<212> TYPE: PRT
<213> ORGANISM: Neisseria meningitidis

<400> SEQUENCE: 34

Ser Val Ser Arg Ala Gly Val Leu Ala Gly Val Gly Ala Leu Val Arg
 1               5                  10                  15

Gln Gly Ala Lys Leu Gly Lys Arg Ala Val Pro Tyr Val Gly Thr Ala
             20                  25                  30

Leu Leu Ala Tyr Asp Ile Tyr Glu Thr Phe Lys Asp Glu Ile Lys Glu
         35                  40                  45

Gln Gly Tyr Gln Tyr Asp Pro Glu Thr Asp Lys Phe Val Lys Gly Tyr
     50                  55                  60

Glu Tyr Ser Asn Cys Ile Trp Glu His Ala Glu Asn Gly Ile Lys Thr
 65                  70                  75                  80

Tyr Gly Cys Tyr Gly Val Asp Ser Ser Ile Met Arg Leu Met Ser Asp
                 85                  90                  95

Tyr Ser Arg Phe Pro Glu Val Lys Leu Met Glu His Gln
            100                 105                 110

<210> SEQ ID NO 35
<211> LENGTH: 80
<212> TYPE: PRT
<213> ORGANISM: Neisseria meningitidis

<400> SEQUENCE: 35

Tyr Lys Glu Glu Met Asp Ala Lys Lys Leu Glu Glu Ile Leu Ser Leu
 1               5                  10                  15

Lys Val Asp Ala Asn Pro Asp Lys Tyr Ile Lys Ala Thr Gly Tyr Pro
             20                  25                  30

Gly Tyr Ser Glu Lys Val Glu Val Ala Pro Gly Thr Lys Val Asn Met
         35                  40                  45

Gly Pro Val Thr Asp Arg Asn Gly Asn Pro Val Gln Val Val Ala Thr
     50                  55                  60

Phe Gly Arg Asp Ser Gln Gly Asn Thr Thr Val Asp Val Gln Val Ile
 65                  70                  75                  80

<210> SEQ ID NO 36
```

```
<211> LENGTH: 80
<212> TYPE: PRT
<213> ORGANISM: Neisseria meningitidis

<400> SEQUENCE: 36

Tyr Lys Glu Glu Met Asp Ala Lys Lys Leu Glu Glu Ile Leu Ser Leu
1               5                   10                  15

Lys Val Asp Ala Asn Pro Asp Lys Tyr Ile Lys Ala Thr Gly Tyr Pro
                20                  25                  30

Gly Tyr Ser Glu Lys Val Glu Val Ala Pro Gly Thr Lys Val Asn Met
            35                  40                  45

Gly Pro Val Thr Asp Arg Asn Gly Asn Pro Val Gln Val Val Ala Thr
        50                  55                  60

Phe Gly Arg Asp Ser Gln Gly Asn Thr Thr Val Asp Val Gln Val Ile
65                  70                  75                  80

<210> SEQ ID NO 37
<211> LENGTH: 80
<212> TYPE: PRT
<213> ORGANISM: Neisseria meningitidis

<400> SEQUENCE: 37

Tyr Lys Glu Glu Met Asp Ala Lys Lys Leu Glu Glu Ile Leu Ser Leu
1               5                   10                  15

Lys Val Asp Ala Asn Pro Asp Lys Tyr Ile Lys Ala Thr Gly Tyr Pro
                20                  25                  30

Gly Tyr Ser Glu Lys Val Glu Val Ala Pro Gly Thr Lys Val Asn Met
            35                  40                  45

Gly Pro Val Thr Asp Arg Asn Gly Asn Pro Val Gln Val Val Ala Thr
        50                  55                  60

Phe Gly Arg Asp Ser Gln Gly Asn Thr Thr Val Asp Val Gln Val Ile
65                  70                  75                  80

<210> SEQ ID NO 38
<211> LENGTH: 80
<212> TYPE: PRT
<213> ORGANISM: Neisseria meningitidis

<400> SEQUENCE: 38

Tyr Lys Glu Glu Met Asp Ala Lys Lys Leu Glu Glu Ile Leu Ser Leu
1               5                   10                  15

Lys Val Asp Ala Asn Pro Asp Lys Tyr Ile Lys Ala Thr Gly Tyr Pro
                20                  25                  30

Gly Tyr Ser Glu Lys Val Glu Val Ala Pro Gly Thr Lys Val Asn Met
            35                  40                  45

Gly Pro Val Thr Asp Arg Asn Gly Asn Pro Val Gln Val Val Ala Thr
        50                  55                  60

Phe Gly Arg Asp Ser Gln Gly Asn Thr Thr Val Asp Val Gln Val Ile
65                  70                  75                  80

<210> SEQ ID NO 39
<211> LENGTH: 80
<212> TYPE: PRT
<213> ORGANISM: Neisseria meningitidis

<400> SEQUENCE: 39

Tyr Lys Glu Glu Met Asp Ala Lys Lys Leu Glu Glu Ile Leu Ser Leu
1               5                   10                  15

Lys Val Asp Ala Asn Pro Asp Lys Tyr Ile Lys Ala Thr Gly Tyr Pro
                20                  25                  30
```

Gly Tyr Ser Glu Lys Val Glu Val Ala Pro Gly Thr Lys Val Asn Met
            35                  40                  45

Gly Pro Val Thr Asp Arg Asn Gly Asn Pro Val Gln Val Val Ala Thr
    50                  55                  60

Phe Gly Arg Asp Ser Gln Gly Asn Thr Thr Val Asp Val Gln Val Ile
65                  70                  75                  80

<210> SEQ ID NO 40
<211> LENGTH: 80
<212> TYPE: PRT
<213> ORGANISM: Neisseria meningitidis

<400> SEQUENCE: 40

Tyr Lys Glu Glu Met Asp Ala Lys Lys Leu Glu Glu Ile Leu Ser Leu
1               5                   10                  15

Lys Val Asp Ala Asn Pro Asp Lys Tyr Ile Lys Ala Thr Gly Tyr Pro
            20                  25                  30

Gly Tyr Ser Glu Lys Val Glu Val Ala Pro Gly Thr Lys Val Asn Met
            35                  40                  45

Gly Pro Val Thr Asp Arg Asn Gly Asn Pro Val Gln Val Val Ala Thr
    50                  55                  60

Phe Gly Arg Asp Ser Gln Gly Asn Thr Thr Val Asp Val Gln Val Ile
65                  70                  75                  80

<210> SEQ ID NO 41
<211> LENGTH: 80
<212> TYPE: PRT
<213> ORGANISM: Neisseria meningitidis

<400> SEQUENCE: 41

Tyr Lys Glu Glu Met Asp Ala Lys Lys Leu Glu Glu Ile Leu Ser Leu
1               5                   10                  15

Lys Val Asp Ala Asn Pro Asp Lys Tyr Ile Lys Ala Thr Gly Tyr Pro
            20                  25                  30

Gly Tyr Ser Glu Lys Val Glu Val Ala Pro Gly Thr Lys Val Asn Met
            35                  40                  45

Gly Pro Val Thr Asp Arg Asn Gly Asn Pro Val Gln Val Val Ala Thr
    50                  55                  60

Phe Gly Arg Asp Ser Gln Gly Asn Thr Thr Val Asp Val Gln Val Ile
65                  70                  75                  80

<210> SEQ ID NO 42
<211> LENGTH: 80
<212> TYPE: PRT
<213> ORGANISM: Neisseria meningitidis

<400> SEQUENCE: 42

Tyr Lys Glu Glu Met Asp Ala Lys Lys Leu Glu Glu Ile Leu Ser Leu
1               5                   10                  15

Lys Val Asp Ala Asn Pro Asp Lys Tyr Ile Lys Ala Thr Gly Tyr Pro
            20                  25                  30

Gly Tyr Ser Glu Lys Val Glu Val Ala Pro Gly Thr Lys Val Asn Met
            35                  40                  45

Gly Pro Val Thr Asp Arg Asn Gly Asn Pro Val Gln Val Val Ala Thr
    50                  55                  60

Phe Gly Arg Asp Ser Gln Gly Asn Thr Thr Val Asp Val Gln Val Ile
65                  70                  75                  80

```
<210> SEQ ID NO 43
<211> LENGTH: 80
<212> TYPE: PRT
<213> ORGANISM: Neisseria gonorrheae

<400> SEQUENCE: 43

Tyr Lys Glu Glu Met Asp Ala Lys Lys Pro Glu Glu Ile Leu Ser Leu
 1               5                  10                  15

Lys Val Asp Ala Asp Pro Asp Lys Tyr Ile Glu Ala Thr Gly Tyr Pro
                20                  25                  30

Gly Tyr Ser Glu Lys Val Glu Val Ala Pro Gly Thr Lys Val Asn Met
            35                  40                  45

Gly Pro Val Thr Asp Arg Asn Gly Asn Pro Val Gln Val Ala Ala Thr
        50                  55                  60

Phe Gly Arg Asp Ala Gln Gly Asn Thr Thr Ala Asp Val Gln Val Ile
65                  70                  75                  80

<210> SEQ ID NO 44
<211> LENGTH: 80
<212> TYPE: PRT
<213> ORGANISM: Neisseria gonorrheae

<400> SEQUENCE: 44

Tyr Lys Glu Glu Met Asp Ala Lys Lys Pro Glu Glu Ile Leu Ser Leu
 1               5                  10                  15

Lys Val Asp Ala Asp Pro Asp Lys Tyr Ile Glu Ala Thr Gly Tyr Pro
                20                  25                  30

Gly Tyr Ser Glu Lys Val Glu Val Ala Pro Gly Thr Lys Val Asn Met
            35                  40                  45

Gly Pro Val Thr Asp Arg Asn Gly Asn Pro Val Gln Val Ala Ala Thr
        50                  55                  60

Phe Gly Arg Asp Ala Gln Gly Asn Thr Thr Ala Asp Val Gln Val Ile
65                  70                  75                  80

<210> SEQ ID NO 45
<211> LENGTH: 80
<212> TYPE: PRT
<213> ORGANISM: Neisseria gonorrheae

<400> SEQUENCE: 45

Tyr Lys Glu Glu Met Asp Ala Lys Lys Pro Glu Glu Ile Leu Ser Leu
 1               5                  10                  15

Lys Val Asp Ala Asp Pro Asp Lys Tyr Ile Glu Ala Thr Gly Tyr Pro
                20                  25                  30

Gly Tyr Ser Glu Lys Val Glu Val Ala Pro Gly Thr Lys Val Asn Met
            35                  40                  45

Gly Pro Val Thr Asp Arg Asn Gly Asn Pro Val Gln Val Ala Ala Thr
        50                  55                  60

Phe Gly Arg Asp Ala Gln Gly Asn Thr Thr Ala Asp Val Gln Val Ile
65                  70                  75                  80

<210> SEQ ID NO 46
<211> LENGTH: 80
<212> TYPE: PRT
<213> ORGANISM: Neisseria meningitidis

<400> SEQUENCE: 46

Tyr Lys Glu Glu Met Asp Ala Lys Lys Leu Glu Glu Ile Leu Ala Leu
 1               5                  10                  15

Lys Val Asp Ala Asn Pro Asp Lys Tyr Ile Gln Ala Thr Gly Tyr Pro
```

```
                20                  25                  30
Gly Tyr Ser Glu Lys Val Glu Val Ala Pro Gly Thr Lys Val Asn Met
             35                  40                  45

Gly Pro Val Thr Asp Arg Asn Gly Asn Pro Val Gln Val Val Ala Thr
         50                  55                  60

Phe Gly Arg Asp Ser Gln Gly Asn Thr Thr Val Asp Val Gln Val Ile
 65                  70                  75                  80

<210> SEQ ID NO 47
<211> LENGTH: 253
<212> TYPE: PRT
<213> ORGANISM: Neisseria meningitidis

<400> SEQUENCE: 47

Ser Val Ser Arg Ala Gly Val Leu Ala Gly Val Gly Lys Leu Ala Arg
 1               5                  10                  15

Leu Gly Ala Lys Leu Ser Thr Arg Ala Val Pro Tyr Val Gly Thr Ala
             20                  25                  30

Leu Leu Ala His Asp Val Tyr Glu Thr Phe Lys Glu Asp Ile Gln Ala
         35                  40                  45

Gln Gly Tyr Gln Tyr Asp Pro Glu Thr Asp Lys Phe Val Lys Gly Tyr
     50                  55                  60

Glu Tyr Ser Asn Cys Leu Trp Tyr Glu Asp Lys Arg Ile Asn Arg
 65                  70                  75                  80

Thr Tyr Gly Cys Tyr Gly Val Asp Ser Ser Ile Met Arg Leu Met Ser
             85                  90                  95

Asp Asp Ser Arg Phe Pro Glu Val Lys Glu Leu Met Glu Ser Gln Met
         100                 105                 110

Tyr Arg Leu Ala Arg Pro Phe Trp Asn Trp His Lys Glu Glu Leu Asn
     115                 120                 125

Lys Leu Ser Ser Leu Asp Trp Asn Asn Phe Val Leu Asn Ser Cys Thr
130                 135                 140

Phe Asp Trp Asn Gly Gly Asp Cys Val Val Asn Lys Gly Asp Asp Phe
145                 150                 155                 160

Arg Asn Gly Ala Asp Phe Ser Leu Ile Arg Asn Ser Lys Tyr Lys Glu
                165                 170                 175

Glu Met Asp Ala Lys Lys Leu Glu Glu Ile Leu Ser Leu Lys Val Asp
            180                 185                 190

Ala Asn Pro Asp Lys Tyr Ile Lys Ala Thr Gly Tyr Pro Gly Tyr Ser
        195                 200                 205

Glu Lys Val Glu Val Ala Pro Gly Thr Lys Val Asn Met Gly Pro Val
    210                 215                 220

Thr Asp Arg Asn Gly Asn Pro Val Gln Val Val Ala Thr Phe Gly Arg
225                 230                 235                 240

Asp Ser Gln Gly Asn Thr Thr Val Asp Val Gln Val Ile
                245                 250

<210> SEQ ID NO 48
<211> LENGTH: 254
<212> TYPE: PRT
<213> ORGANISM: Neisseria meningitidis

<400> SEQUENCE: 48

Ser Val Ser Arg Ala Ala Val Leu Ser Gly Val Gly Lys Leu Ala Arg
 1               5                  10                  15

Leu Gly Ala Lys Leu Ser Thr Arg Ala Val Pro Tyr Val Gly Thr Ala
             20                  25                  30
```

```
Leu Leu Ala His Asp Val Tyr Glu Thr Phe Lys Glu Asp Ile Gln Ala
            35                  40                  45

Gln Gly Tyr Gln Tyr Asp Pro Glu Thr Asp Lys Phe Val Lys Gly Tyr
        50                  55                  60

Glu Tyr Ser Asn Cys Leu Trp Tyr Glu Asp Lys Arg Arg Ile Asn Arg
 65                  70                  75                  80

Thr Tyr Gly Cys Tyr Gly Val Asp Ser Ser Ile Met Arg Leu Met Ser
                85                  90                  95

Asp Asp Ser Arg Phe Pro Glu Val Lys Glu Leu Met Glu Ser Gln Met
            100                 105                 110

Tyr Arg Leu Ala Arg Pro Phe Trp Asn Trp His Lys Glu Glu Leu Asn
        115                 120                 125

Lys Leu Ser Ser Leu Asp Trp Asn Asn Phe Val Leu Asn Arg Cys Thr
130                 135                 140

Phe Asn Trp Asn Gly Gly Asp Cys Leu Val Asn Lys Gly Asp Asp Phe
145                 150                 155                 160

Arg Asn Gly Ala Asp Phe Ser Leu Ile Arg Asn Ser Lys Tyr Lys Glu
                165                 170                 175

Glu Met Asp Ala Lys Lys Leu Glu Glu Ile Leu Ser Leu Lys Val Asp
            180                 185                 190

Ala Asn Pro Asp Lys Tyr Ile Lys Ala Thr Gly Tyr Pro Gly Tyr Ser
        195                 200                 205

Glu Lys Val Glu Val Ala Pro Gly Thr Lys Val Asn Met Gly Pro Val
    210                 215                 220

Thr Asp Arg Asn Gly Asn Pro Val Gln Val Val Ala Thr Phe Gly Arg
225                 230                 235                 240

Asp Ser Gln Gly Asn Thr Thr Val Asp Val Gln Val Ile Pro
                245                 250

<210> SEQ ID NO 49
<211> LENGTH: 21
<212> TYPE: DNA
<213> ORGANISM: Artificial Sequence
<220> FEATURE:
<223> OTHER INFORMATION: Synthetic primer

<400> SEQUENCE: 49
catggatcca tcagtttccc g                                             21

<210> SEQ ID NO 50
<211> LENGTH: 23
<212> TYPE: DNA
<213> ORGANISM: Artificial Sequence
<220> FEATURE:
<223> OTHER INFORMATION: Synthetic primer

<400> SEQUENCE: 50
cataagcttt gcttccgcgc ttc                                           23

<210> SEQ ID NO 51
<211> LENGTH: 33
<212> TYPE: DNA
<213> ORGANISM: Artificial Sequence
<220> FEATURE:
<223> OTHER INFORMATION: Synthetic primer

<400> SEQUENCE: 51
catggatcca tcagtttccc gcgccgccgt ctt                                33
```

```
<210> SEQ ID NO 52
<211> LENGTH: 28
<212> TYPE: DNA
<213> ORGANISM: Artificial Sequence
<220> FEATURE:
<223> OTHER INFORMATION: Synthetic primer

<400> SEQUENCE: 52
cataagcttg ttctcaaagc tgaacgcg                                    28

<210> SEQ ID NO 53
<211> LENGTH: 21
<212> TYPE: DNA
<213> ORGANISM: Artificial Sequence
<220> FEATURE:
<223> OTHER INFORMATION: Synthetic primer

<400> SEQUENCE: 53
gccgccgtct tgtcaggagt c                                           21

<210> SEQ ID NO 54
<211> LENGTH: 21
<212> TYPE: DNA
<213> ORGANISM: Artificial Sequence
<220> FEATURE:
<223> OTHER INFORMATION: Synthetic primer

<400> SEQUENCE: 54
atcaagcaca gtcactgtga a                                           21

<210> SEQ ID NO 55
<211> LENGTH: 25
<212> TYPE: DNA
<213> ORGANISM: Artificial Sequence
<220> FEATURE:
<223> OTHER INFORMATION: Synthetic primer

<400> SEQUENCE: 55
agcatatgtt ggggatgttt tcggt                                       25

<210> SEQ ID NO 56
<211> LENGTH: 28
<212> TYPE: DNA
<213> ORGANISM: Artificial Sequence
<220> FEATURE:
<223> OTHER INFORMATION: Synthetic primer

<400> SEQUENCE: 56
agaagcttga cttcacgaga tactgtgc                                    28

<210> SEQ ID NO 57
<211> LENGTH: 28
<212> TYPE: DNA
<213> ORGANISM: Artificial Sequence
<220> FEATURE:
<223> OTHER INFORMATION: Synthetic primer

<400> SEQUENCE: 57
acggatcctt ggggatgttt tcggttaa                                    28

<210> SEQ ID NO 58
<211> LENGTH: 28
<212> TYPE: DNA
<213> ORGANISM: Artificial Sequence
<220> FEATURE:
<223> OTHER INFORMATION: Synthetic primer

<400> SEQUENCE: 58
```
agaagcttct agacttcacg agatactg         28

<210> SEQ ID NO 59
<211> LENGTH: 26
<212> TYPE: DNA
<213> ORGANISM: Artificial Sequence
<220> FEATURE:
<223> OTHER INFORMATION: Synthetic primer

<400> SEQUENCE: 59
catggatcca tcagtatccc gcgccg         26

<210> SEQ ID NO 60
<211> LENGTH: 25
<212> TYPE: DNA
<213> ORGANISM: Artificial Sequence
<220> FEATURE:
<223> OTHER INFORMATION: Synthetic primer

<400> SEQUENCE: 60
cataagcttt gcttctgcgc ttccg         25

<210> SEQ ID NO 61
<211> LENGTH: 26
<212> TYPE: DNA
<213> ORGANISM: Artificial Sequence
<220> FEATURE:
<223> OTHER INFORMATION: Synthetic primer

<400> SEQUENCE: 61
catggatcca tcagtttccc gcgccg         26

<210> SEQ ID NO 62
<211> LENGTH: 23
<212> TYPE: DNA
<213> ORGANISM: Artificial Sequence
<220> FEATURE:
<223> OTHER INFORMATION: Synthetic primer

<400> SEQUENCE: 62
cataagcttt gcttccgcgc ttc         23

<210> SEQ ID NO 63
<211> LENGTH: 5
<212> TYPE: PRT
<213> ORGANISM: Artificial Sequence
<220> FEATURE:
<223> OTHER INFORMATION: Synthetic peptide

<400> SEQUENCE: 63

Gly Ser Gly Gly Ser
 1               5

<210> SEQ ID NO 64
<211> LENGTH: 4
<212> TYPE: PRT
<213> ORGANISM: Artificial Sequence
<220> FEATURE:
<223> OTHER INFORMATION: Synthetic peptide

<400> SEQUENCE: 64

Gly Gly Gly Ser
 1

<210> SEQ ID NO 65
<211> LENGTH: 4

```
<212> TYPE: PRT
<213> ORGANISM: Artificial Sequence
<220> FEATURE:
<223> OTHER INFORMATION: Synthetic peptide

<400> SEQUENCE: 65

Gly Gly Ser Gly
 1

<210> SEQ ID NO 66
<211> LENGTH: 5
<212> TYPE: PRT
<213> ORGANISM: Artificial Sequence
<220> FEATURE:
<223> OTHER INFORMATION: Synthetic peptide

<400> SEQUENCE: 66

Gly Gly Ser Gly Gly
 1               5

<210> SEQ ID NO 67
<211> LENGTH: 5
<212> TYPE: PRT
<213> ORGANISM: Artificial Sequence
<220> FEATURE:
<223> OTHER INFORMATION: Synthetic peptide

<400> SEQUENCE: 67

Gly Ser Gly Ser Gly
 1               5

<210> SEQ ID NO 68
<211> LENGTH: 5
<212> TYPE: PRT
<213> ORGANISM: Artificial Sequence
<220> FEATURE:
<223> OTHER INFORMATION: Synthetic peptide

<400> SEQUENCE: 68

Gly Ser Gly Gly Gly
 1               5

<210> SEQ ID NO 69
<211> LENGTH: 5
<212> TYPE: PRT
<213> ORGANISM: Artificial Sequence
<220> FEATURE:
<223> OTHER INFORMATION: Synthetic peptide

<400> SEQUENCE: 69

Gly Gly Gly Ser Gly
 1               5

<210> SEQ ID NO 70
<211> LENGTH: 5
<212> TYPE: PRT
<213> ORGANISM: Artificial Sequence
<220> FEATURE:
<223> OTHER INFORMATION: Synthetic peptide

<400> SEQUENCE: 70

Gly Ser Ser Ser Gly
 1               5
```